US006217867B1

(12) United States Patent
Ildstad

(10) Patent No.: US 6,217,867 B1
(45) Date of Patent: Apr. 17, 2001

(54) NON-LETHAL METHODS FOR CONDITIONING A RECIPIENT FOR BONE MARROW TRANSPLANTATION

(75) Inventor: Suzanne T. Ildstad, Wynewood, PA (US)

(73) Assignee: University of Pittsburgh, Pittsburgh, PA (US)

(*) Notice: Subject to any disclaimer, the term of this patent is extended or adjusted under 35 U.S.C. 154(b) by 0 days.

(21) Appl. No.: 09/177,704

(22) Filed: Oct. 22, 1998

Related U.S. Application Data

(60) Continuation-in-part of application No. 08/785,070, filed on Jan. 17, 1997, now Pat. No. 5,876,692, which is a division of application No. 08/337,785, filed on Nov. 14, 1994, now Pat. No. 5,635,156, which is a continuation-in-part of application No. 08/120,256, filed on Sep. 13, 1993, now Pat. No. 5,514,364.

(60) Provisional application No. 60/073,764, filed on Feb. 5, 1998.

(51) Int. Cl.[7] .......................... A61K 39/395; A61K 31/00

(52) U.S. Cl. .................... 424/144.1; 424/1.49; 424/1.53; 424/153.1; 424/141.1; 424/154.1; 424/93.1

(58) Field of Search .................................. 424/1.49, 1.53, 424/153.1, 144.1, 154.1, 141.1, 93.1

(56) References Cited

U.S. PATENT DOCUMENTS

| | | |
|---|---|---|
| 4,500,637 | 2/1985 | Neville, Jr. et al. . |
| 4,998,931 | 3/1991 | Slichter et al. . |
| 5,178,858 | 1/1993 | Reichert et al. . |
| 5,187,266 | 2/1993 | Farquhar et al. . |
| 5,273,738 | 12/1993 | Matthews et al. . |
| 5,374,658 | 12/1994 | Lau . |
| 5,504,092 | 4/1996 | Nilsson et al. . |
| 5,514,364 | 5/1996 | Ildstad . |
| 5,635,156 | 6/1997 | Ildstad . |
| 5,635,364 | 6/1997 | Clark et al. . |
| 5,876,708 | * 3/1999 | Sachs ................................ 424/93.1 |

OTHER PUBLICATIONS

Aguila, H. et al., 1997, "From stem cells to lymphocytes: biology and transplantation", Imm. Rev. 157:13–39.

Antin et al., 1991, "Selective depletion of bone marrow T lymphocytes with anti–CD5 monoclonal antibodies: effective prophylaxis for graft–versus–host disease in patients with hematologic malignancies", Blood 78(8):2139–2149.

Auchincloss and Sachs, 1983, "Mechanisms of tolerance in murine radiation bone marrow chimeras", Transplan. 36:436.

Benett, M. et al., 1987, "Biology and genetics of hybrid resistance", Adv. Immunol. 41:333.

Blom et al., 1996, "Induction of specific tolerance through mixed hematopoietic chimerism prevents chronic renal allograft rejection in a rat model", Surgery 120:213–220.

(List continued on next page.)

*Primary Examiner*—Diana Dudash
*Assistant Examiner*—Shahnam Sharareh
(74) *Attorney, Agent, or Firm*—Pennie & Edmonds LLP

(57) ABSTRACT

The present invention relates to non-lethal methods of conditioning a recipient for bone marrow transplantation. In particular, it relates to the use of nonlethal doses of total body irradiation, total lymphoid irradiation, cell type-specific or cell marker-specific antibodies, especially antibodies directed to bone marrow stromal cell markers, NK cells, or the CD8 cell marker, cytotoxic drugs, or a combination thereof. The methods of the invention have a wide range of applications, including, but not limited to, the conditioning of an individual for hematopoietic reconstitution by bone marrow transplantation for the treatment of hematologic malignancies, hematologic disorders, autoimmunity, infectious diseases such as acquired immunodeficiency syndrome, and the engraftment of bone marrow cells to induce tolerance for solid organ, tissue and cellular transplantation.

9 Claims, 52 Drawing Sheets

OTHER PUBLICATIONS

Figure 1:
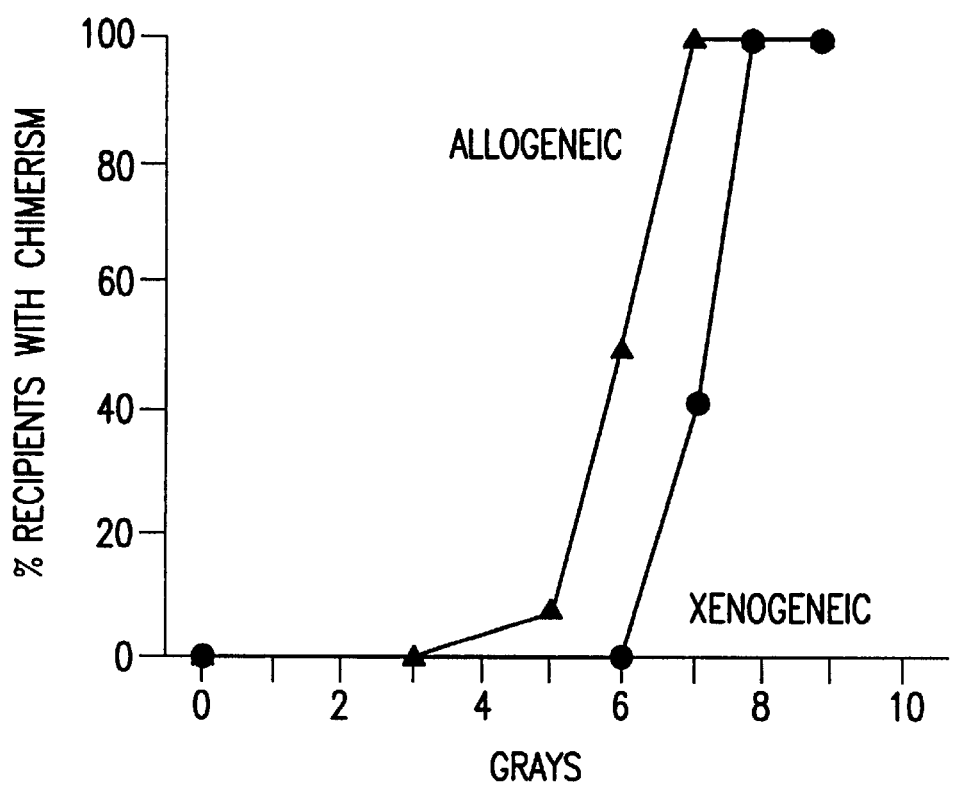

Brecher et al., 1982, "Special proliferative sites are not needed for seeding and proliferation of transfused bone marrow cells in normal syngeneic mice", PNAS USA 79:5085–5087.

Cobbold et al., 1986, "Monoclonal antibodies for the prevention of graft–versus–host disease and marrow graft rejection", Transplantation 42:239.

Cobbold et al., 1992, "Reprogramming the immune system for peripheral tolerance with CD4 and CD8 monoclonal antibodies", Immunol. Rev. 129:165–201.

Cobbold et al., 1990, "Reprogramming the immune system for tolerance with monoclonal antibodies", Seminars in Immunol. 2:377–387.

Cobbold et al., 1986, "Monoclonal antibodies to promote marrow engraftment and tissue graft tolerance", Nature 323:164–166.

Cobbold et al., 1990, "The induction of skin graft tolerance in major histocompatibility complex–mismatched or primed recipients: primed T cells can be tolerized in the periphery with anti–CD4 and anti–CD8 antibodies", Eur. J. Immunol. 20:2747–2755.

Cohen et al., 1992, "A modified transfusion program for prevention of stroke in sickle cell disease", Blood 76(7):1657–1661.

Colson et al., 1996, "Durable mixed allogenic chimerism and tolerance by a nonlethal radiation–based cytoreductive approach", J. Immunol. 157:2820–2829.

Copelan and Deeg, 1992, "Conditioning for allogeneic marrow transplantation in patients with lymphohematopoietic malignancies without the use of total body irradiation", Blood 80(7):1648.

Dorshkind, 1990, "Regulation of hemopoiesis by bone marrow stromal cells and their products", Annu. Rev. Immunol. 8:111–137.

Down et al., 1991, "Synergeneic and allogeneic bone marrow engraftment after total body irradiation: dependence on dose, dose rate, and fractionation", Blood 77(3):661–669.

Engh et al., 1996, "Role of natural killer cells and classical (RT1.A) vs nonclassical (RT1.C) class I molecules in acute bone marrow allograft rejection in lethally irradiated rats", Trans. Proc. 28:3265.

Exner et al., 1997, "In vivo depletion of host $CD4^+$ and $CD8^+$ cells permits engraftment of bone marrow stem cells and tolerance induction with minimal conditioning", Surgery 122:221–227.

Forsythe, 1994, "ATG–a polyclonal sledgehammer", Transplan. Immunol. 2:148.

Fung, J. et al., 1997, "Clinical trials and projected future of liver xenotransplantation", World J. Surg. 21(9):956–961.

Gershwin et al., 1974, "Cyclophosphamide: use in practice", Annals Int. Med. 80:531.

Gassman et al., 1986, "Immune reactivity after high–dose irradiation", Transplant. 41(3):380–384.

Graw et al., 1972, "Bone marrow transplantation from HL–A–matched doners to patients with acute leukemia", Transplantation 14:79.

Greenberger, 1991, "The hematopoietic microenvironment", Crit. Rev. Oncology/Hematology 11:65–84.

Haas et al., 1985, "Prolonging the immunosuppressive effects of lymphoid irradiation by suppression of T cell recovery prior to organ transplantation", Trans. Proc. 17(1):1294–1298.

Hoffman et al., 1989, "Induction of stable chimerism and elimination of graft–versus–host disease by depletion of T lymphocytes from bone marrow using immunomagnetic beads", Surgery 106:354–363.

Ildstad et al., 1986, "Effect of selective T cell depletion of host and/or donor bone marrow on lymphopoietic repopulation, tolerance, and graft–vs–host disease in mixed allogenic chimeras (B10+B10.D2→B10)", J. Immunol. 136:28–33.

Ildstad et al., 1986, "Alloresistence to engraftment of allogeneic donor bone marrow is mediated by an $Lyt-2^+$ T cell in mixed allogeneic reconstitution", J. Exp. Med. 163:1343–1348.

Ildstad and Sachs, 1984, "Reconstitution with syngeneic plus allogeneic or xenogeneic bone marrow leads to specific acceptance of allografts or xenografts", Nature 307:168.

Ildstad et al., 1985, "Characterization of mixed allogenic chimeras", J. Exp. Med. 162:231–244.

Ildstad et al., 1991, "Cross–species bone marrow transplantion: evidence for tolerance induction, stem cell engraftment, and maturation of T lymphocytes in a Xenogeneic stromal environment (rat → mouse)", J. Exp. Med. 174:467–478.

Jacobsen et al., 1992, "Highly restricted expression of a stromal cell determinant in mouse bone marrow in vivo", J. Exp. Med. 176:927–935.

Jandl et al., 1961, "Red cell filtration and the pathogenesis of certain hemolytic anemias", Blood 18(2):133–148.

Kodish et al., 1991, Bone marrow transplantation for sickle cell disease N. Engl. J. Med. 325(19):1349–1353.

Markus et al., 1993, "Induction of donor–specific transplantation tolerance to skin and cardiac allografts using mixed chimersim in (A + B → A) in rats", Cell Transplan. 2:345.

Mayumi and Good, 1989, "The necessity of both allogeneic antigens and stem cells for cyclophosphamide–induced skin allograft tolerance in mice", Immunobiol. 178:287–304.

Mayumi et al., 1986, "Drug–induced tolerance to allografts in mice", Transplantation 42(4):417.

Mayumi et al., 1987, "Drug–induced tolerance to allografts in mice", Transplantation 44(2):286–290.

Mayumi and Good, 1989, "Long–lasting skin allograft tolerance in adult mice induced across fully allogenic (multimajor H–2 plus multiminor histocompatibility) antigen barriers by a tolerance–inducing method using cyclophosphamide", J. Exp. Med. 169:213–238.

McCarthy et al., 1987, "Immunological competence and host–specific tolerance of antibody–facilitated bone marrow chimeras", Transplantation 44:97–105.

McCarthy et al., 1985, "Characterization of host lymphoid cells in antibody–facilitated bone marrow chimeras", Transplantation 40(1):12–17.

Monaco, 1991, Studies in rodents on the use of polyclonal antilymphocyte serum and donor–specific bone marow to induce specific unresponsiveness to skin allografts', Trans. Proc. 23(4):2061–2067.

Monaco et al., 1966, "Studies on heterologous anti–lymphocyte serum in mice. III. Immunologic tolerance and chimerism produced across the H–2 locus with adult thymectomy and anti–lymphocyte serum", Ann. NY Acad. Sci 129:190–209.

Murphy, W. J. et al., 1990, "An absence of T cells in murine bone marrow allografts leads to an increased susceptibility to rejection by natural killer cells and T cells", J. Immunol. 144:3305–3311.

Nakamura et al., 1990, "Graft rejection by cytolytic T cells", Transplant. 49(2):453–458.

Orloff et al., 1995, "Prevention of chronic rejection and graft arteriosclerosis by tolerance induction", Transplantation 59:282.

Pierce et al., 1989, "Effects of THY–1+ cell depletion on the capacity of donor lymphoid cells to induce tolerance across an entire MHC disparity in sublethally irradiated adult hosts", Transplant. 48(2):289–296.

Pierce et al., 1985, "The role of donor lymphoid cells in the transfer of allograft tolerance", Transplant. 40(6):702–707.

Qin et al., 1989, "Induction of classical transplantation tolerance in the adult", J. Exp. Med. 169:779–794.

Qin et al., 1990, "Induction of tolerance in peripheral T cells with monoclonal antibodies", Eur. J. Immunol. 20:2737–2745.

Rolstad and Benestad, 1984, "The 'natural resistance' to bone marrow allografts in normal and athymic nude rats rapid cytotoxic reactions both in vivo and in vitro", Eur. J. Immunol. 14:793–799.

Sharabi et al., 1990, "Specific tolerance induction across a xenogeneic barrier: production of mixed rat/mouse lympho-hematopoietic chimeras using a nonlethal preparative regimen", J. Exp. Med. 172(1):195–202.

Sharabi et al., 1989, "Mixed chimerism and permanent specific transplantation tolerance induced by a nonlethal preparative regimen", J. Exp. Med. 169:493–502.

Shirota and Tavassoli, 1991, "Cyclophosphamide–induced alterations of bone marrow endothelium: implications in homing of narrow cells after transplantation", Exp. Hematol. 19:369.

Simmons and Torok–Storb, 1991, "Identification of stromal cell precursors in human bone marrow by a novel monoclonal antibody, STRO–1", Blood 78:55–62.

Singer et al., 1981, "Self recognition in allogeneic radiation bone marrow chimeras", J. Exp. Med. 1–3:1286–1301.

Slavin et al., 1978, "Transplantation tolerance in adult rats using total lymphoid irradiation: permanent survival of skin, heart, and marrow allografts", J. Exp. Med. 147(3):700–707.

Slavin et al., 1978, "Transplantation of allogeneic bone marrow without graft–versus–host disease using total lymphoid irradiation", J. Exp. Med. 147(4):963–972.

Solderling et al., 1985, "A correlation between conditioning and engraftment in recipients of MHC–mismatched T cell–depleted murine bone marrow transplants", J. Immunol. 135(2):941–946.

Starzl, 1993, "Baboon–to–human liver transplantation", Lancet 341:65–71.

Stephenson, 1995, "Xenotransplantation workshop ponders science, safety of animal tissue grafts", JAMA 274(4):285–288.

Stewart et al., 1993, "Lomg–term engraftment of normal and post–5–fluorouracil murine marrow into normal nonmyeloablated mice", Blood 81:2566–2571.

Storb et al., 1997, "Stable mixed hematopoietic chimerism in DLA–identical littermate dogs given sublethal total body irradiation before and pharmacological immunosuppression after marrow transplantation", Blood 89(8):3048–3054.

Sykes et al., 1997, "Induction of high levels of allogeneic hematopoietic reconstitution and donor–specific tolerance without myelosuppressive conditioning", Nat. Med. 3:783–787.

Sykes et al., 1988, "Mixed allogeneic chimerism as an approach to transplantation tolerance", Immunol. Today 9:23–27.

Tomita et al., 1994, "Myelosuppressive conditioning is required to achieve engraftment of pluripotent stem cells contained in moderate doses of synergeneic bone marrow", Blood 83:939–948.

Vaage et al., 1991, "Allospecific recognition of hemic cells in vitro by natural killer cells from athymic rats: evidence that allodeterminants coded for by single major histocompatibility complex haplotypes are recognized", Eur. J. Immunol. 21:2167–2175.

Vallera and Blazer, 1989, "T cell depletion for graft–versus–host–disease prophylaxis", Transplantation 47:751–760.

Vitetta and Uhr, 1985, "Immunotoxins", Annu. Rev. Immunol. 3:197–212.

Wolf, P. et al., 1997, "The pig as a model in liver xenotransplantation", Vet. Res. 1997, 28(3):217–222.

Wood et al., 1971, "Use of homozygous allogeneic bone marrow for induction of tolerance with antilymphocyte serum: dose and timing", Trans. Proc. 3(1):676.

Wood and Monaco, 1977, "The effect of timing of skin grafts on subsequent survival in ALS–treated, marrow–infused mice", Transplantation 23:78–86.

Tomita et al. Transplantation, 61 (3) 477–485, 1996.*

* cited by examiner

NON-LETHAL METHODS FOR CONDITIONING A RECIPIENT FOR BONE MARROW TRANSPLANTATION

The present application claims priority to U.S. Provisional Patent Application Ser. No. 60/073,764, filed Feb. 5, 1998, and is a continuation-in-part of U.S. patent application Ser. No. 08/785,070, filed Jan. 17, 1997, now U.S. Pat. No. 5,876,692 which is a Divisional of U.S. patent application Ser. No. 08/337,785, filed Nov. 14, 1994, now U.S. Pat. No. 5,635,156, issued Jun. 3, 1997, which is a continuation-in-part of application Ser. No. 08/120,256 filed Sep. 13, 1993, now U.S. Pat. No. 5,514,364, issued May 7, 1996, all of which are incorporated by reference herein in their entirety.

1. INTRODUCTION

The present invention relates to non-lethal methods of conditioning a recipient for bone marrow transplantation. In particular, it relates to the use of nonlethal doses of total body irradiation, total lymphoid irradiation, cell type-specific or cell marker-specific antibodies, especially antibodies directed to NK cells, bone marrow stromal cell markers, or the CD8 cell marker, cytotoxic drugs, or a combination thereof. The methods of the invention have a wide range of applications, including, but not limited to, the conditioning of an individual for hematopoietic reconstitution by bone marrow transplantation for the treatment of hematologic malignancies, hematologic disorders, autoimmunity, infectious diseases such as acquired immunodeficiency syndrome, and the engraftment of bone marrow cells to induce tolerance for solid organ, tissue and cellular transplantation.

2. BACKGROUND OF THE INVENTION

A major goal in solid organ transplantation is the permanent engraftment of the donor organ without a graft rejection immune response generated by the recipient, while preserving the immunocompetence of the recipient against other foreign antigens. Typically, in order to prevent host rejection responses, nonspecific immunosuppressive agents such as cyclosporine, methotrexate, steroids and FK506 are used. These agents must be administered on a daily basis and if stopped, graft rejection usually results. However, a major problem in using nonspecific immunosuppressive agents is that they function by suppressing all aspects of the immune response, thereby greatly increasing a recipient's susceptibility to infections and other diseases, including cancer.

Furthermore, despite the use of immunosuppressive agents, graft rejection still remains a major source of morbidity and mortality in human organ transplantation. Most human transplants fail within 10 years without permanent graft acceptance. Only 50% of heart transplants survive 5 years and 20% of kidney transplants survive 10 years. (See Opelz et al., 1981, Lancet 1:1223; Gjertson, 1992, UCLA Tissue Typing Laboratory, p. 225; Powles, 1980, *Lancet*, p. 327; Ramsay, 1982, *New Engl. J. Med.*, p. 392). It would therefore be a major advance if tolerance to the donor cells can be induced in the recipient.

The only known clinical condition in which complete systemic donor-specific transplantation tolerance occurs is when chimerism is created through bone marrow transplantation. (See Qin et al., 1989, *J Exp Med.* 169:779; Sykes et al., 1988, *Immunol. Today* 9:23; Sharabi et al., 1989, *J. Exp. Med.* 169:493). This has been achieved in neonatal and adult animal models as well as in humans by total lymphoid irradiation of a recipient followed by bone marrow transplantation with donor cells. The success rate of allogeneic bone marrow transplantation is, in large part, dependent on the ability to closely match the major histocompatibility complex (MHC) of the donor cells with that of the recipient cells to minimize the antigenic differences between the donor and the recipient, thereby reducing the frequency of host-versus-graft responses and graft-versus-host disease (GVHD). In fact, MHC matching is essential, only one or two antigen mismatch is acceptable because GVHD is very severe in cases of greater disparities. In addition, it also requires the appropriate conditioning of the recipient by lethal doses of total body irradiation (TBI).

The MHC is a gene complex that encodes a large array of individually unique glycoproteins expressed on the surface of both donor and host cells that are the major targets of transplantation rejection immune responses. In the human, the MHC is referred to as HLA. When HLA identity is achieved by matching a patient with a family member such as a sibling, the probability of a successful outcome is relatively high, although GVHD is still not completely eliminated. However, when allogeneic bone marrow transplantation is performed between two MHC-mismatched individuals of the same species, common complications involve failure of engraftment, poor immunocompetence and a high incidence of GVHD. Unfortunately, only about 20% of all potential candidates for bone marrow transplantation have a suitable family member match.

The field of bone marrow transplantation was developed originally to treat bone marrow-derived cancers. It is believed by those skilled in the art even today that lethal conditioning of a human recipient is required to achieve successful engraftment of donor bone marrow cells in the recipient. In fact, prior to the present invention, current conventional bone marrow transplantation has exclusively relied upon lethal conditioning approaches to achieve donor bone marrow engraftment. The requirement for lethal irradiation of the host which renders it totally immunoincompetent poses a significant limitation to the potential clinical application of bone marrow transplantation to a variety of disease conditions, including solid organ or cellular transplantation, sickle cell anemia, thalassemia and aplastic anemia.

The risk inherent in tolerance-inducing conditioning approaches must be low when less toxic means of treating rejection are available or in cases of morbid, but relatively benign conditions. In addition to solid organ transplantation, hematologic disorders, including aplastic anemia, severe combined immunodeficiency (SCID) states, thalassemia, diabetes and other autoimmune disease states, sickle cell anemia, and some enzyme deficiency states, may all significantly benefit from a nonlethal preparative regimen which would allow partial engraftment of allogeneic or even xenogeneic bone marrow to create a mixed host/donor chimeric state with preservation of immunocompetence and resistance to GVHD. For example, it is known that only approximately 40% of normal erythrocytes are required to prevent an acute sickle cell crisis (Jandl et al., 1961, *Blood* 18(2):133; Cohen et al., 1984, *Blood* 76(7):1657), making sickle cell disease a prime candidate for an approach to achieve mixed multilineage chimerism. Although the morbidity and mortality associated with the conventional full cytoreduction currently utilized for allogeneic bone marrow transplantation cannot be justified for relatively benign disorders, the induction of multilineage chimerism by a less aggressive regimen certainly remains a viable option. Moreover, the use of bone marrow from an HIV-resistant species offers a potential therapeutic strategy for the treatment of acquired immunodeficiency syndrome (AIDS) if bone marrow from a closely related species will also engraft under similar non-lethal conditions, thereby producing new hematopoietic cells such as T cells which are resistant to infection by the AIDS virus.

A number of sublethal conditioning approaches in an attempt to achieve engraftment of allogeneic bone marrow stem cells with less aggressive cytoreduction have been reported in rodent models (Mayumi and Good, 1989, *J Exp Med* 169:213; Slavin et al., 1978, *J Exp Med* 147(3):700; McCarthy et al., 1985, *Transplantation* 40(1):12; Sharabi et al., 1990, *J Exp Med* 172(l):195; Monaco et al., 1966, *Ann NY Acad Sci* 129:190). However, reliable and stable donor cell engraftment as evidence of multilineage chimerism was not demonstrated, and long-term tolerance has remained a question in many of these models (Sharabi and Sachs, 1989, *J. Exp. Med.* 169:493; Cobbold et al., 1992, *Immunol. Rev.* 129:165; Qin et al., 1990, *Eur. J. Immunol.* 20:2737). Moreover, reproducible engraftment has not been achieved, especially when multimajor and multiminor antigenic disparities existed.

Permanent tolerance to donor antigens has been documented in H-2 (MHC) identical or congenic strains with minimal therapy and/or transplantation of donor skin drafts or splenocytes alone (Qin et al., 1990, *Eur J Immunol* 20:2737). However, similar attempts to achieve engraftment and tolerance in MHC-mismatched combinations have not enjoyed the same success. In most models, only transient donor-specific tolerance has been achieved (Mayumi et al., 1987, *Transplantation* 44(2):286; Mayumi et al., 1986, *Transplantation* 42(4):417; Cobbold et al., 1990, *Eur J Immunol* 20:2747; Cobbold et al., 1990, *Seminars in Immunology* 2:377).

Early work by Wood and Monaco attempted to induce tolerance using bone marrow plus anti-lymphocyte serum (ALS) in partial MHC-matched donor-recipient combinations (Wood et al., 1971, *Trans Proc* 3(l):676; Wood and Monaco, 1977, *Transplantation* (Baltimore) 23:78). Even in this semi-allogeneic system, $F_1$ splenocytes were required to facilitate the induction of tolerance, and thymectomy was required for stable long-term tolerance. The additional requirement for splenocytes and thymectomy made potential clinical applicability of such an approach unlikely. However, these studies identified two key factors required for the induction of tolerance: an antigenic source of tolerogen, which is not only involved in tolerance induction, but must also be present at least periodically for permanent antigen-specific tolerance, and a method to tolerize, or prevent activation of new T cells from the thymus, i.e. thymectomy, or intrathymic clonal deletion.

Attempts to induce tolerance to allogeneic bone marrow donor cells using combinations of depleting and non-depleting anti-CD4 and CD8 monoclonal antibodies (mAb) resulted in only transient tolerance to MHC-compatible combinations (Cobbold et al., 1992, *Immunol Rev* 129:165; Qin et al., 1990, *Eur J Immunol* 20:2737). 6Gy of TBI was required to obtain stable engraftment and tolerance when MHC-disparate bone marrow was utilized (Cobbold et a.l., 1986, *Transplantation* 42:239). Sharabi and Sachs attributed the failure of anti-CD4/CD8 mAb therapy alone to the inability of mAb to deplete T cells from the thymus, since persistent cells coated with mAb could be identified in this location (Sharabi and Sachs, 1989, *J Exp Med* 169:493). However, subsequent attempts to induce tolerance by the addition of 7Gy of selective thymic irradiation prior to donor bone marrow transplantation also failed. Engraftment was only achieved with the addition of 3Gy of recipient TBI.

Therefore, there remains a need for non-lethal methods of conditioning a recipient for allogeneic bone marrow transplantation that would result in stable mixed multilineage allogeneic chimerism and long-term donor-specific tolerance.

3. SUMMARY OF THE IDTENTION

The present invention relates to non-lethal methods of conditioning a recipient for bone marrow transplantation. These methods include the use of low, non-lethal doses of irradiation, cell type-specific or marker-specific antibodies and active fragments thereof, cytotoxic drugs or a combination thereof.

The invention is based, in part, on the Applicant's discovery that treatment of normal mice with low, non-lethal doses of TBI, or with antibodies directed against the CD8 cell surface marker, permits the engraftment of allogeneic bone marrow cells in virtually all recipients. In addition, the dosage of TBI can be further reduced when used in combination with anti-lymphocyte globulin (ALG), anti-CD8 antibodies, anti-CD4 antibodies, an increased cell dose, or an alkylating agent such as cyclophosphamide (CyP). Similarly, a partially ablative regimen employing anti-natural killer cell ("NK") antibodies allows engraftment with low, non-lethal doses of TBI. The dosage of TBI can be reduced even more if it is used with both ALG and CyP, agents with different mechanisms of action and non-overlapping toxicities. The reconstituted animals exhibit stable mixed multilineage chimerism in their peripheral blood containing both donor and recipient cells of all lymphohematopoietic lineages, including T cells, B cells, NK cells, macrophages, erythrocytes and platelets. Furthermore, the mixed allogeneic chimeras display donor-specific tolerance to donor-type skin grafts, while they readily reject third-party skin grafts. Donor-specific tolerance is confirmed also by in vitro assays in which lymphocytes obtained from the chimeras are shown to have diminished proliferative and cytotoxic activities against allogeneic donor cells, but retain normal immune reactivity against third-party cells. All allogeneic chimeras conditioned by non-lethal means survive long-term, maintain stable chimerism and do not manifest symptoms of GVHD.

The working examples further demonstrate that total lymphoid irradiation (TLI), a less aggressive and cytoablative regimen than TBI, may also be used at non-lethal doses to condition non-human primates prior to allogeneic or xenogeneic bone marrow transplantation. TLI may be used most effectively with agents such as CyP, and/or ALG, upon optimizing engraftment with a strategy to minimize toxicity to the recipient.

The hematopoietic microenvironment plays a major role in the engraftment of hematopoietic stem cells.

In addition to being a source of growth factors and cellular interactions for the survival and renewal of stem cells, it may also provide physical space for these cells to reside. A number of cell types collectively referred to as stromal cells are found in the vicinity of the hematopoietic stem cells in the bone marrow microenvironment. These cells include both bone marrow-derived $CD45^+$ cells and non-bone marrow-derived $CD45^-$ cells, such as adventitial cells, reticular cells, endothelial cells and adipocytes.

Recently, the Applicant has identified another bone marrow-derived cell type known as hematopoietic facilitatory cells, which when co-administered with donor bone marrow cells enhance the ability of the donor cells to stably engraft in allogeneic and xenogeneic recipients. The facilitatory cells and the stromal cells occupy a substantial amount of space in a recipient's bone marrow microenvironment, which may present a barrier to donor cell engraftment. Hematopoietic stem cells bind to facilitatory cells in vitro and in vivo. Thus, the facilitatory cells may provide physical space or niche on which the stem cells survive and are nurtured. It is therefore desirable to develop conditioning regimens to specifically target and eliminate these and other stromal cell populations in order to provide the space necessary for the hematopoietic stem cells and the associated facilitatory cells in a donor cell preparation to engraft without the use of lethal irradiation.

A wide variety of uses are encompassed by the invention described herein, including, but not limited to, the conditioning of recipients by non-lethal methods for bone marrow transplantation in the treatment of diseases such as hematologic malignancies, infectious diseases such as AIDS, autoimmunity, enzyme deficiency states, anemias, thalassemias, sickle cell disease, and solid organ and cellular transplantation.

4. BRIEF DESCRIPTION OF THE DRAWINGS

FIG. 1 Percentage of animals which engrafted with allogeneic or xenogeneic bone marrow as a function of TBI dose. Lymphoid chimerism was assessed by flow cytometry 2 months post reconstitution. Donor chimerism as low as 0.5% can be detected using this method.

Data points represent results for 8 to 20 recipients pooled from 2 to 5 experiments.

Figure 2:
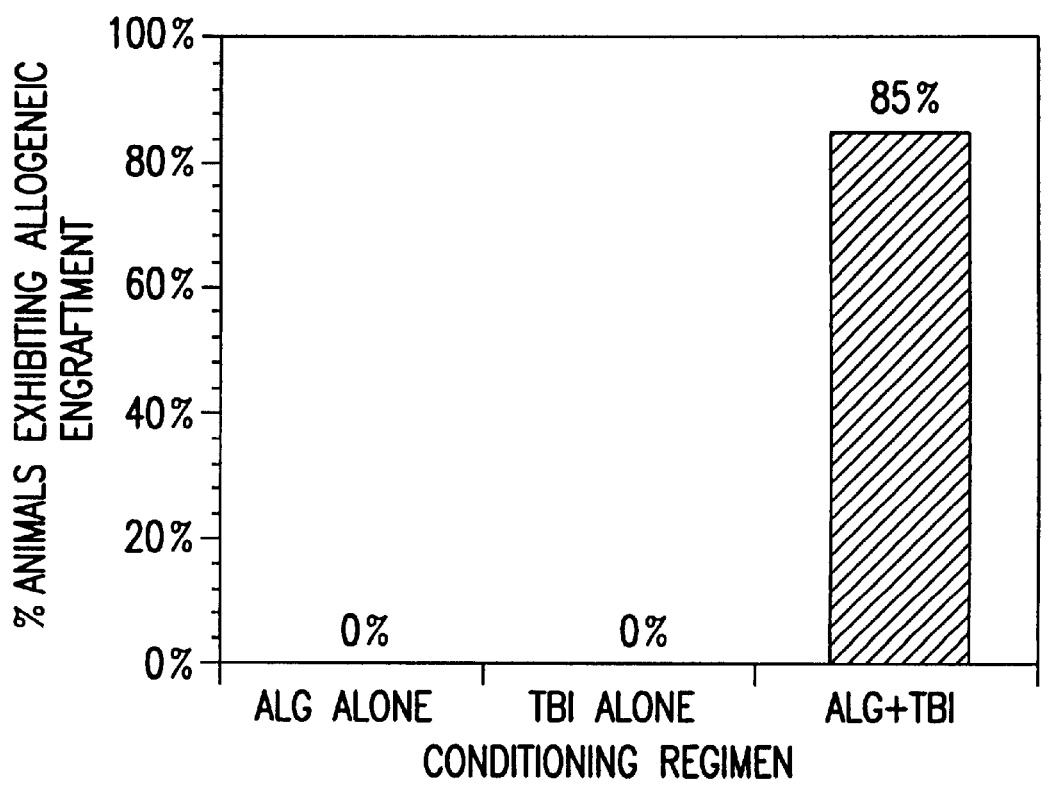

FIG. 2 Percent of animals with allogeneic engraftment in mice treated with one of three conditioning approaches prior to allogeneic bone marrow transplantation—ALG alone given three days prior to transplantation (n=4); 5Gy TBI alone given on the day of transplantation (n=6); or a combination of ALG and 5Gy TBI each as administered previously (n=16). Typing of peripheral blood lymphocytes ("PBL") obtained from treated animals 2 months post reconstitution (BALB/c→B10) was performed using anti Class I H-$2^b$-FITC and H-$2^d$-FITC mAb. Analysis was performed in the lymphoid gate and all values were normalized to 100%.

Figure 3:
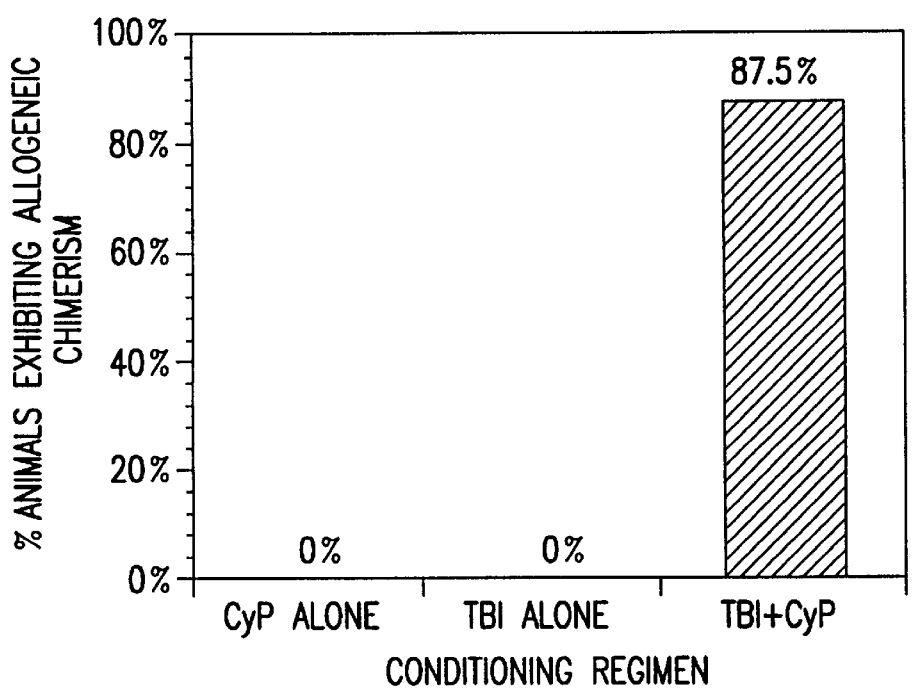

FIG. 3 Percent of animals with allogeneic chimerism in mice treated with one of three conditioning approaches—CyP alone given 2 days prior to bone marrow transplantation (n=5); 5Gy TBI alone on the day of transplantation (n=14); or 5Gy TBI given at the time of marrow transplantation followed 2 days later by CyP (n=8). PBL typing was performed by flow cytometry 2 months post reconstitution (B10.BR→B10 and BALB/c→B10).

Figure 4:
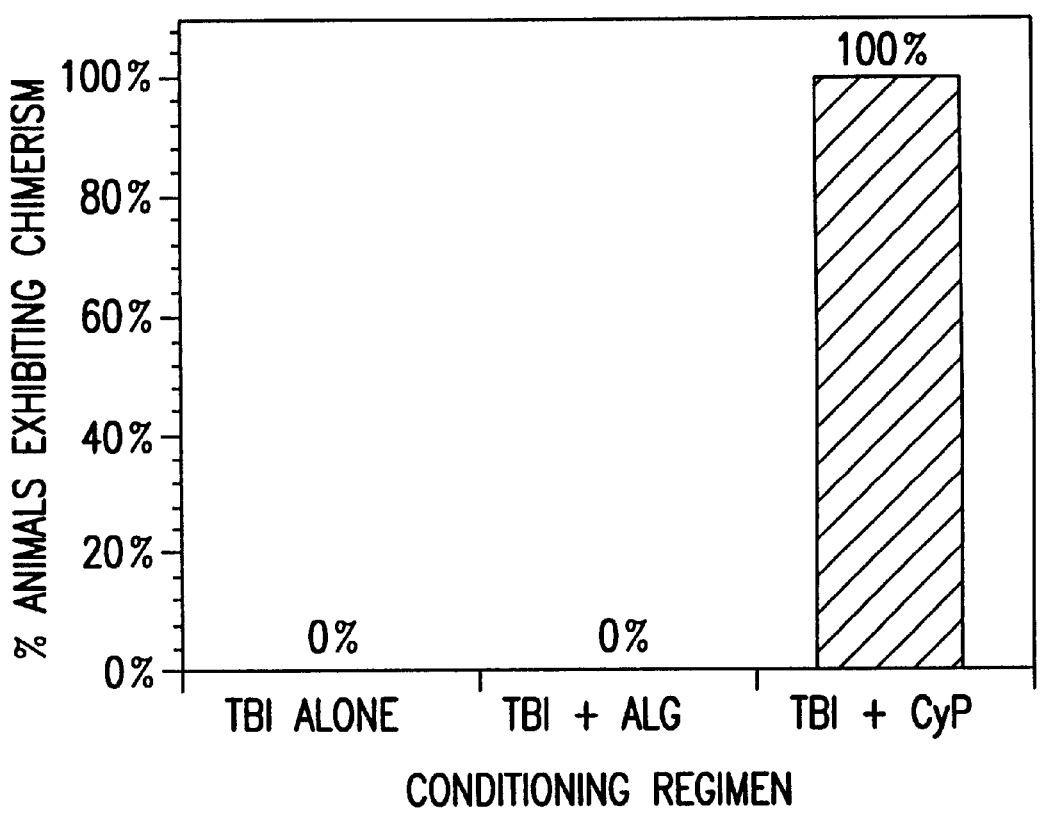

FIG. 4 Percent of mice which engrafted after conditioning with 5Gy TBI given one week prior to BALB/c allogeneic bone marrow transplantation. TBI was administered alone (n=4), followed by ALG given three days prior to bone marrow transplantation (n=4), or followed by CyP given over a four day course prior to transplantation (n=4). Percent of animals which engrafted is represented as a function of the recipient conditioning regimen. PBL typing by flow cytometry was performed to assess donor chimerism in treated animals 2 months after reconstitution. Results are from 1 of 4 representative experiments.

Figure 5:
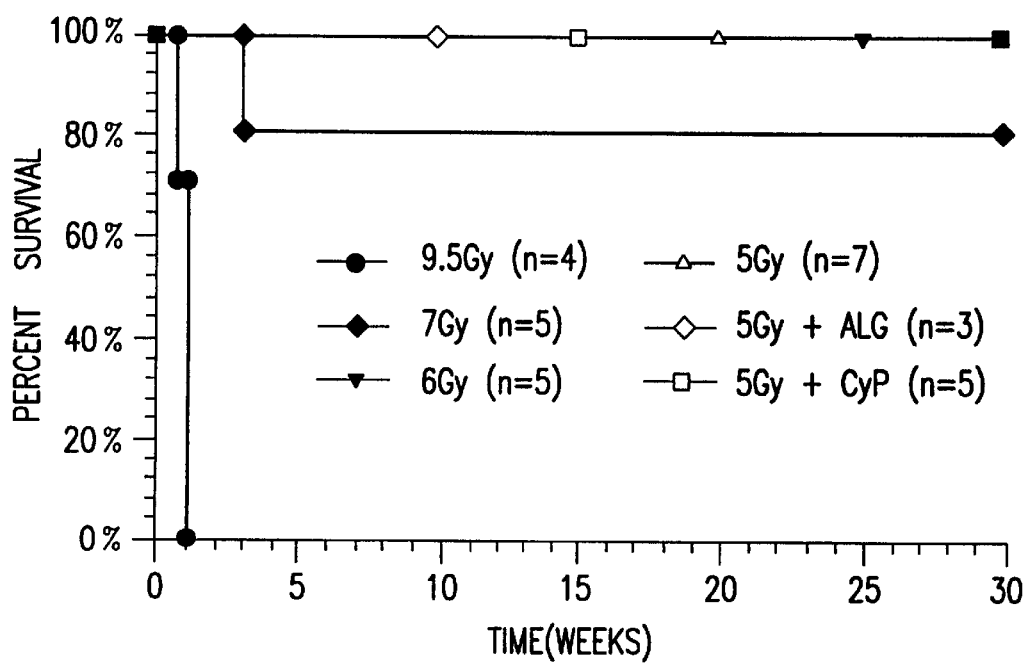

FIG. 5 Life-table survival of untransplanted control mice treated with various nonlethal conditioning regimens. Survival following treatment with 7Gy; 6Gy; 5Gy; 5Gy plus 7 μg/kg ALG i.v.; or 5Gy plus 200 mg/kg CyP i.p. as compared to conventional 9.5Gy lethal irradiation.

FIGS. 6A, 6B, 6C, 6D, 6E, 6F, 6G, 6H, 6I, 6J Two-color flow cytometric analysis for the proportion of allogeneic donor-derived lymphoid (T and B cell), NK, and myeloid (macrophage and granulocyte) lineages in a representative mixed allogeneic chimera prepared using a nonlethal conditioning regimen (BALB/c→B10). Splenic lymphoid tissue was analyzed 10–12 weeks following reconstitution.

Recipient (H-$2^b$) and donor-derived (H-$2^d$) cells of lymphoid and NK lineages were analyzed in the lymphoid gate using anti-H-$2^b$ and H-$2^d$ mAb directly conjugated to FITC or biotinylated and detected with a second streptavidin antibody conjugated to PE (SA-PE). The various subsets were analyzed using anti-T lymphocyte mAb (αβTCR-PE, CD4-FITC, CD8-PE), shown in FIGS. 6A, 6B, 6C, 6D, 6E, 6F, and anti-B lymphocyte (B220-FITC), and anti-natural killer cell (NK1.1-PE) uAb displayed in FIG. 6B. FITC and PE conjugated Leu4 were used as irrelevant controls for background staining for all flow cytometric analysis. The percentage of donor and recipient-derived cells within each lineage is expressed in the upper right hand corner of each respective plot. Results are normalized to 100%.

FIGS. 6K, 6L, 6M, 6N Two-color flow cytometric analysis for the proportion of allogeneic donor-derived lymphoid (T and B cell), NK, and myeloid (macrophage and granulocyte) lineages in a representative mixed allogeneic chimera prepared using a nonlethal conditioning regimen (BALB/c→B10). Splenic lymphoid tissue was analyzed 10–12 weeks following reconstitution. Further analysis of recipient and donor-derived myeloid lineages was performed in the myeloid gate using biotinylated anti-H-$2^b$ and H-$2^d$ mAb detected using SA-PE. Macrophages were analyzed using MAC-1 FITC and granulocytes were detected using GR-1 FITC. The percentage of donor and recipient-derived cells within each lineage is expressed in the upper right hand corner of each respective plot. Results are normalized 100%.

Figure 7:
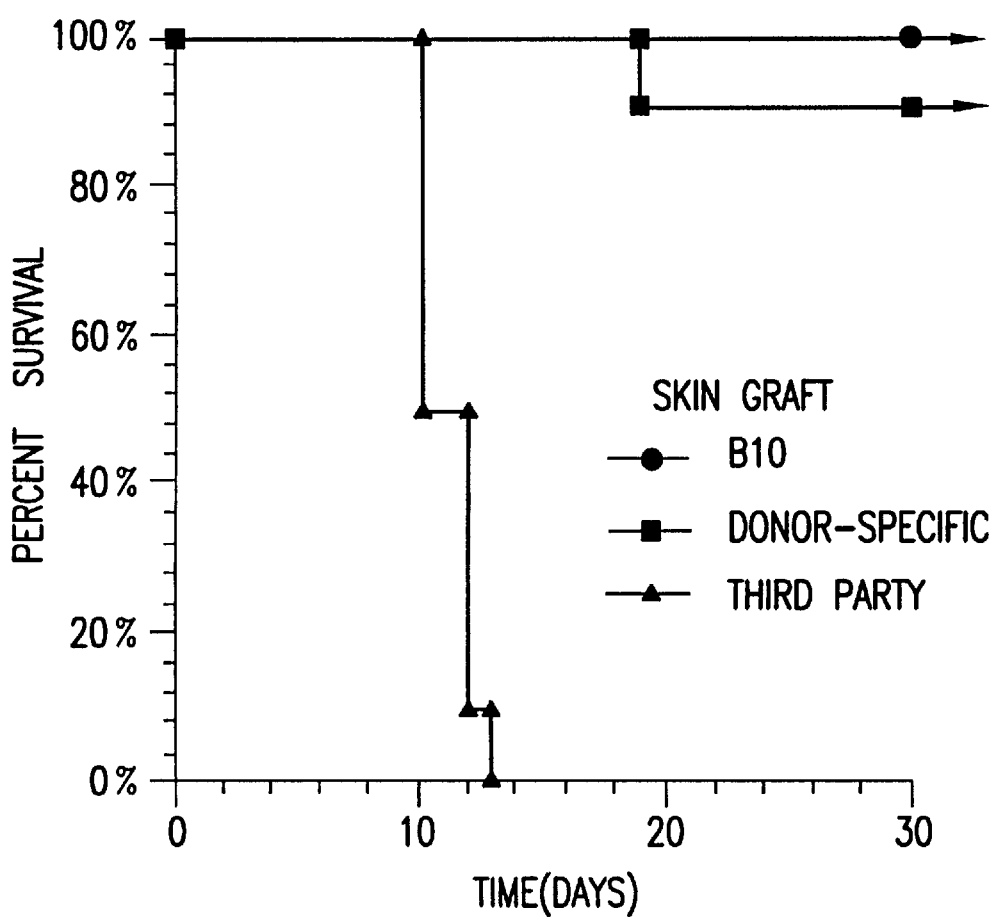

FIG. 7 Survival of full thickness tail skin grafts placed 1 to 7 months post reconstitution using two different donor strain combinations B10.BR (H-$2^k$) or BALB/c (H-$2^d$) Each animal (n=14) received three skin grafts: recipient-type (B10; H-$2^b$); donor-type (B10.BR; H-$2^k$, or BALB/c; H-$2^d$; and third party (DBA; H-$2^d$ or B10.BR; H-$2^k$). Survival was calculated by the life table method. Grafts were followed for a minimum of 35 days. Grafts were scored for evidence of rejection, which was considered complete when no viable residual could be detected.

Figure 8A:
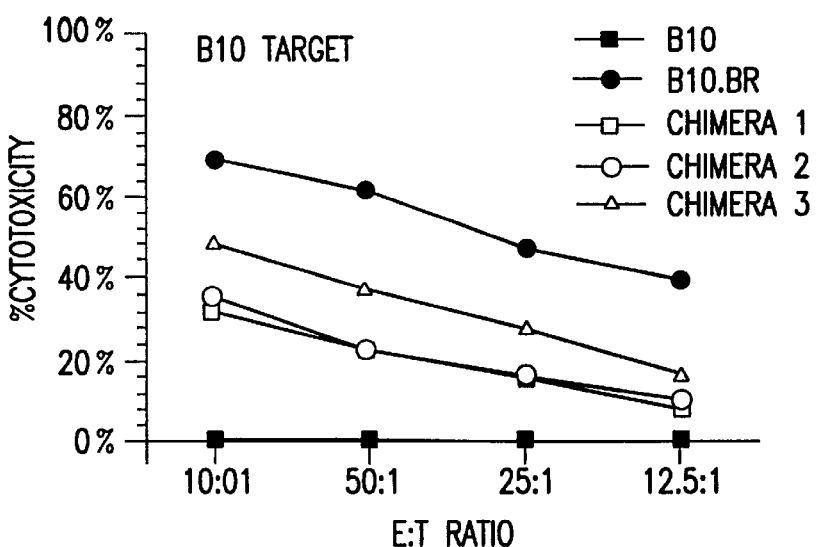
Figure 8B:
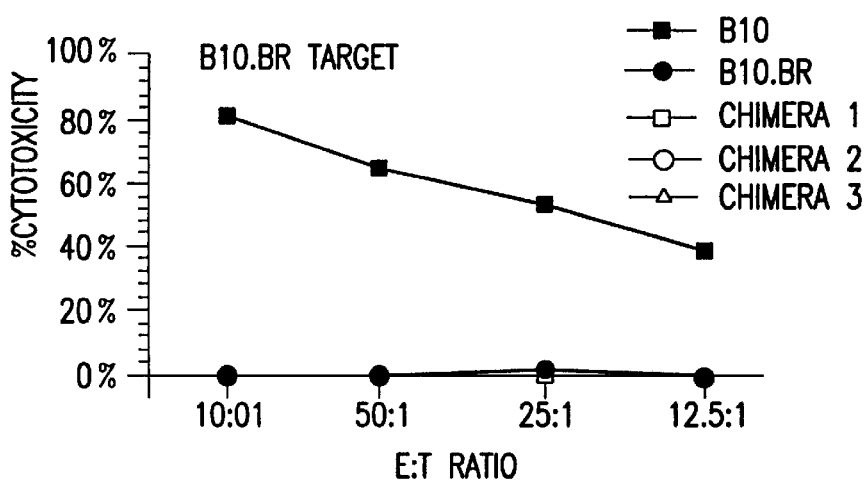
Figure 8C:
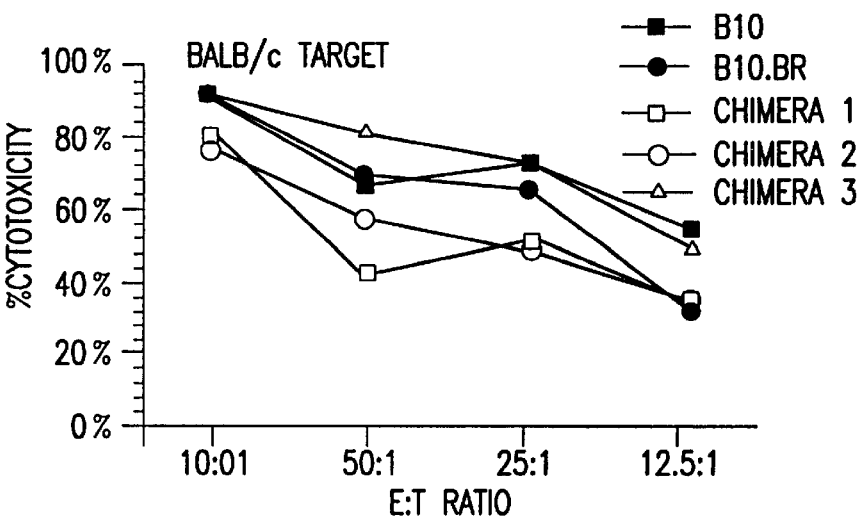

FIG. 8 Specific CTL lysis of $^{51}$Cr-labelled target in one-way CML towards recipient (B10), donor (B10.BR), and third-party (BALB/c) targets. Spontaneous release was <25% unless otherwise indicated. One of five representative experiments.

Figure 9:
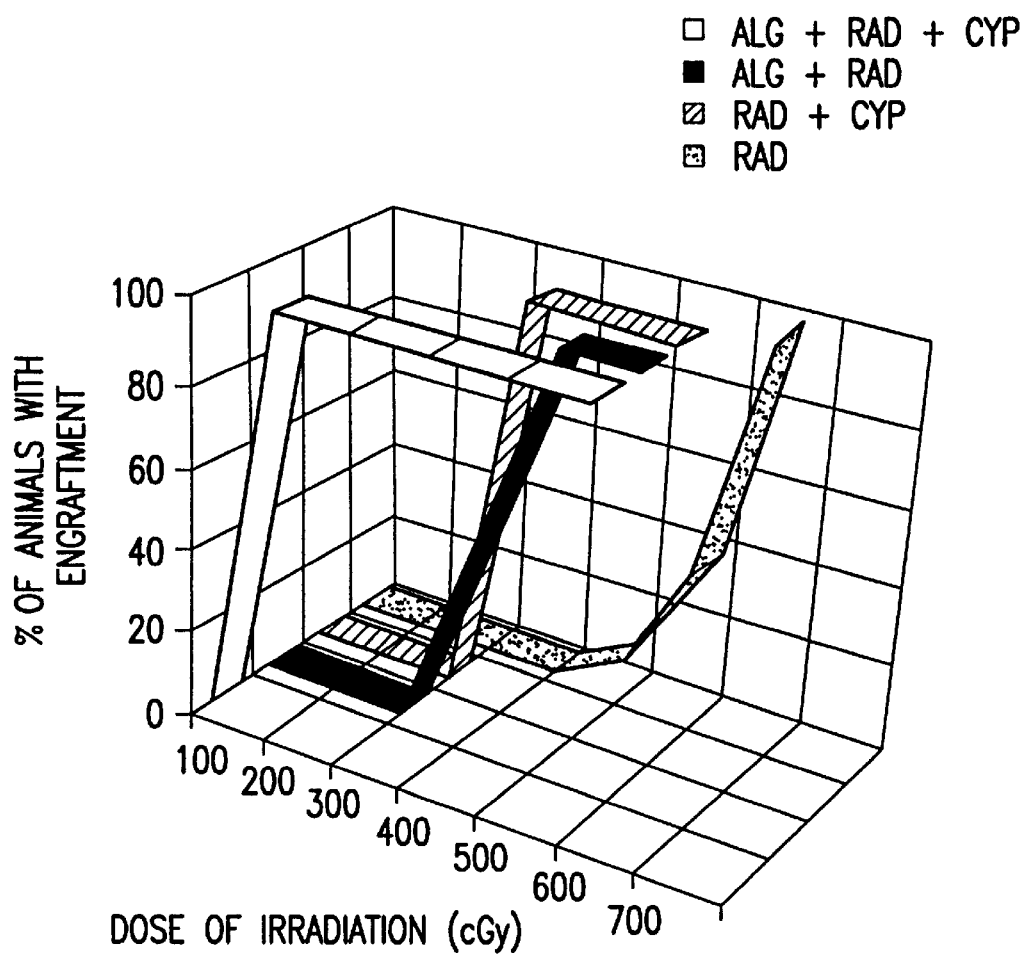

FIG. 9 Percentage of animals with allogeneic donor cell engraftment after treatment with various cytoablative agents.

Figure 10:
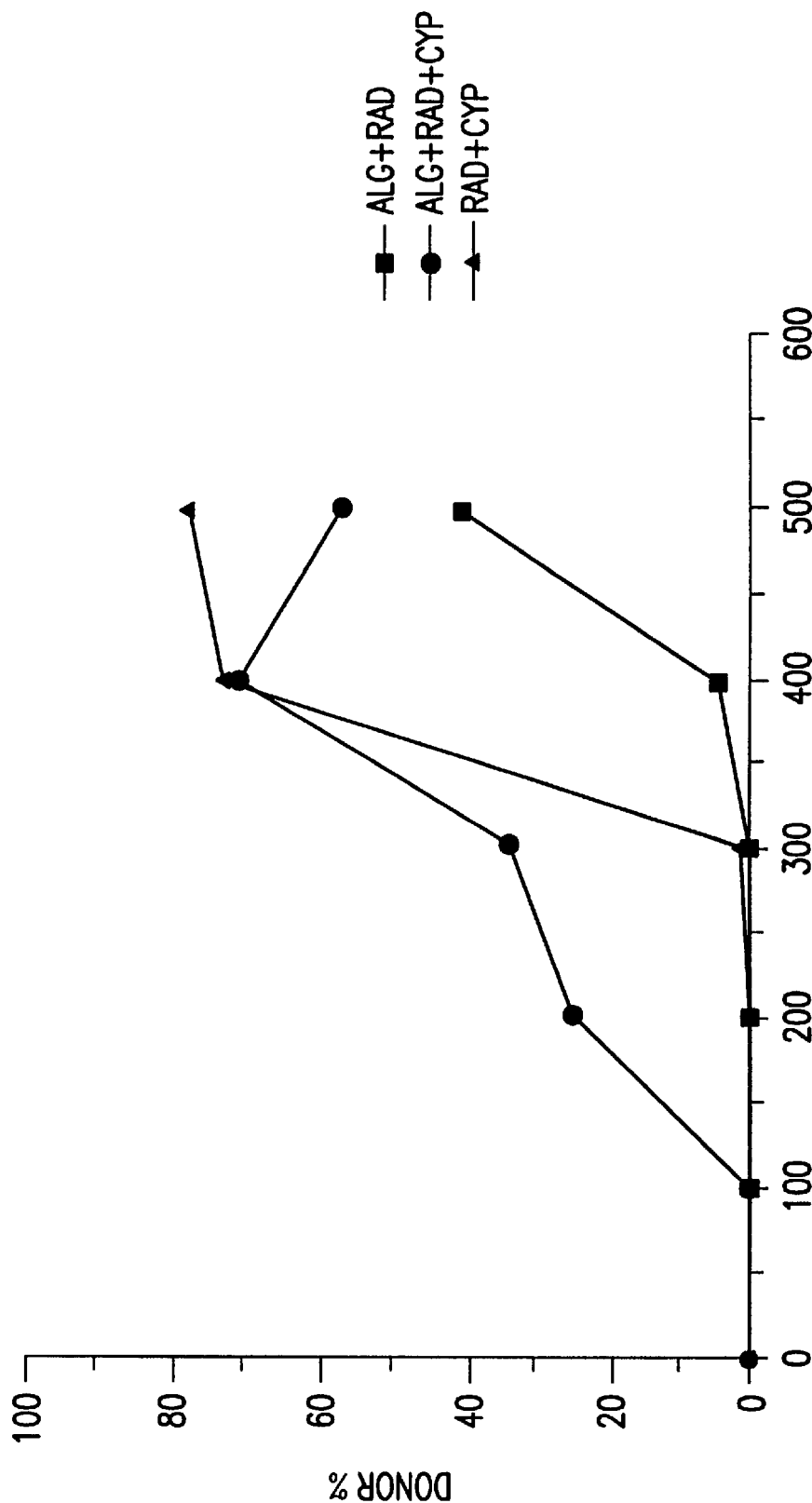

FIG. 10 Percentage of donor cell engraftment in mice engrafted with allogeneic bone marrow cells after treatment with CyP, ALG and various doses of TBI. B10 mice were transplanted with 15×10$^6$ B10.BR cells.

Figure 11:
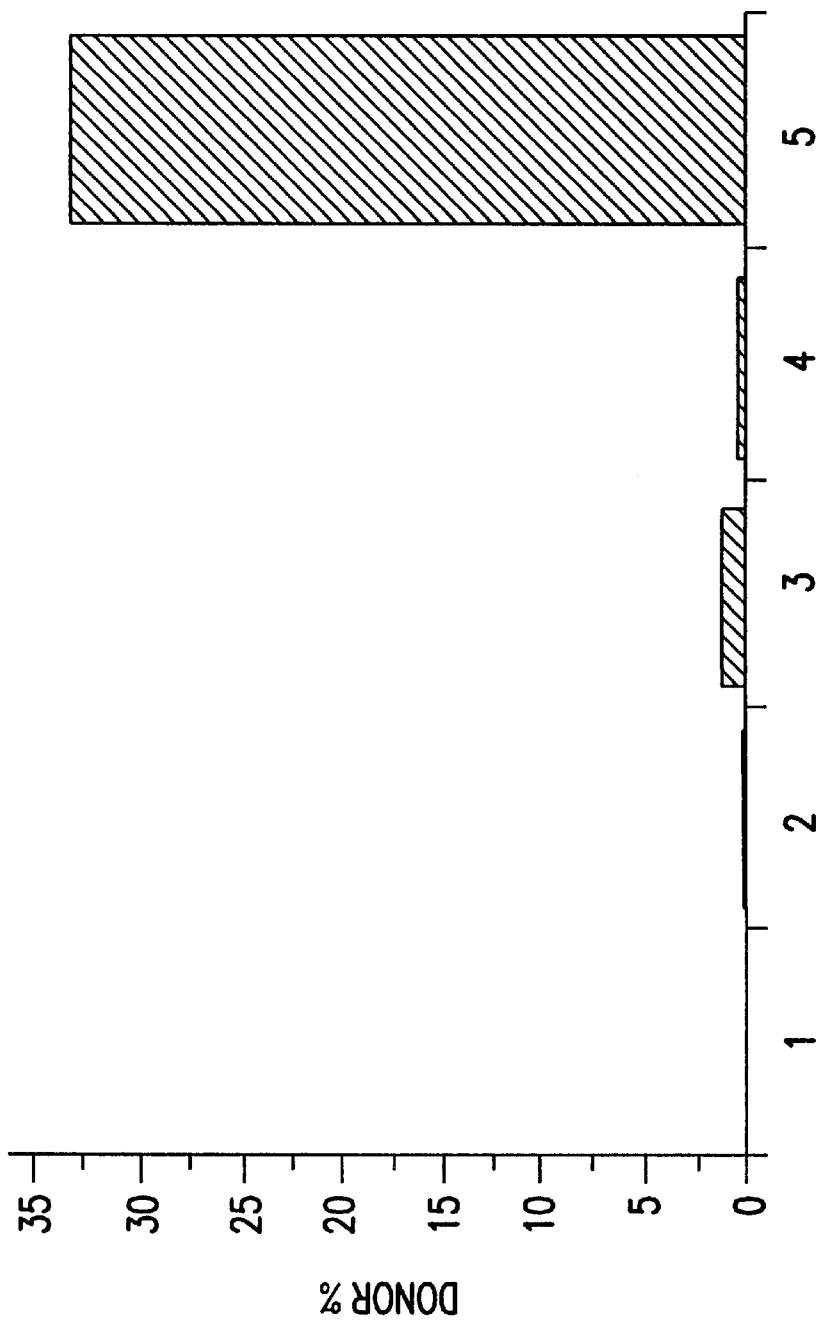
Figure 12A:
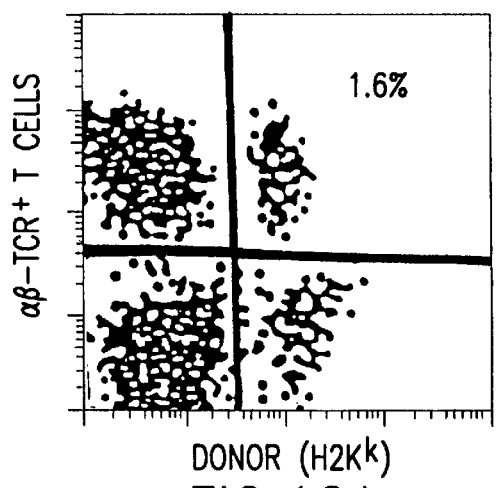
Figure 12B:
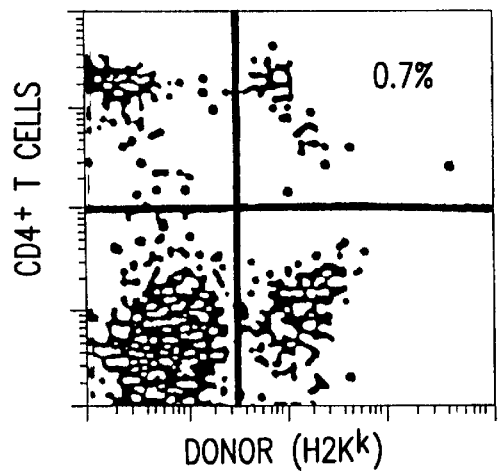
Figure 12C:
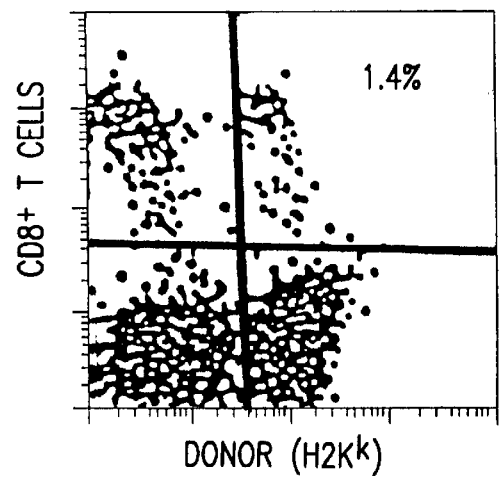
Figure 12D:
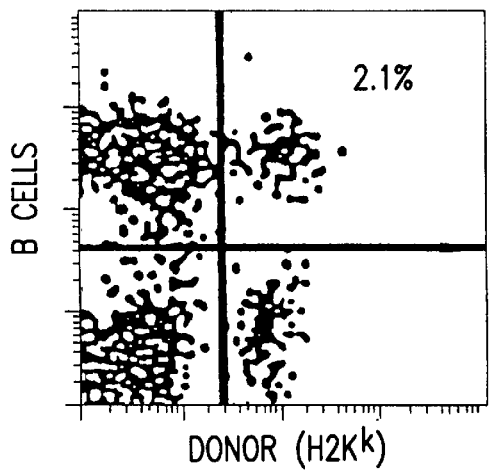
Figure 12E:
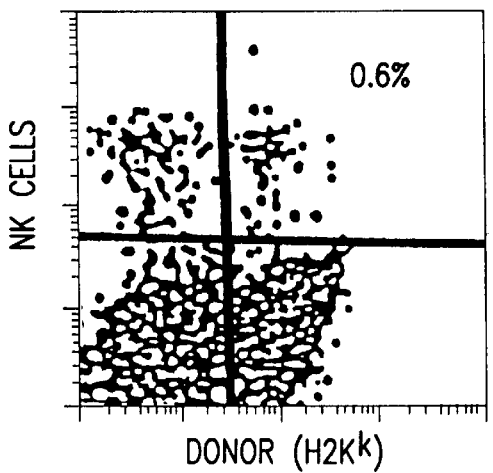
Figure 12F:
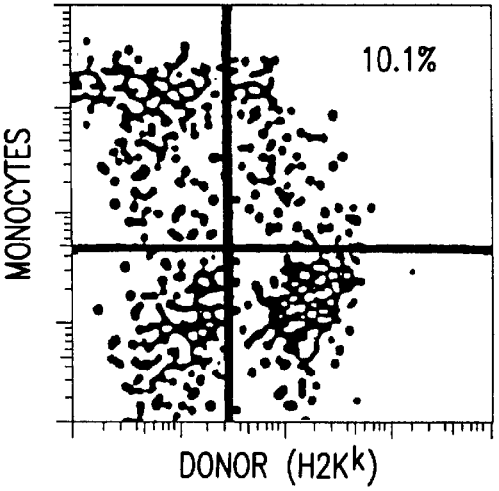
Figure 13A:
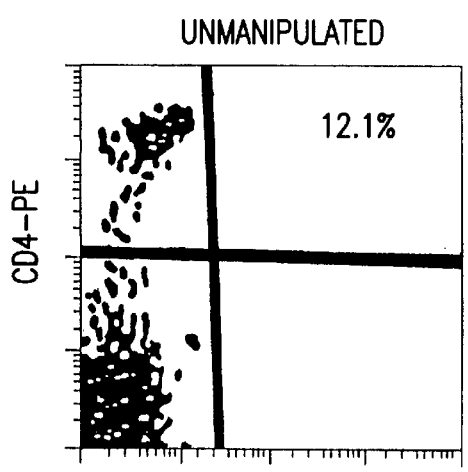
Figure 13B:
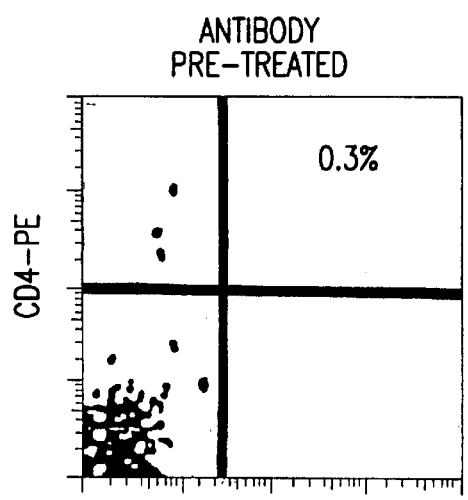
Figure 13C:
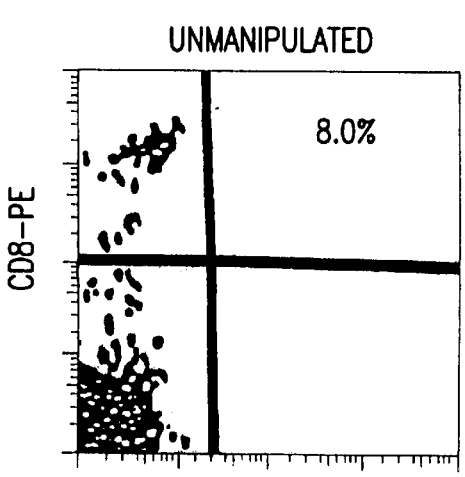
Figure 13D:
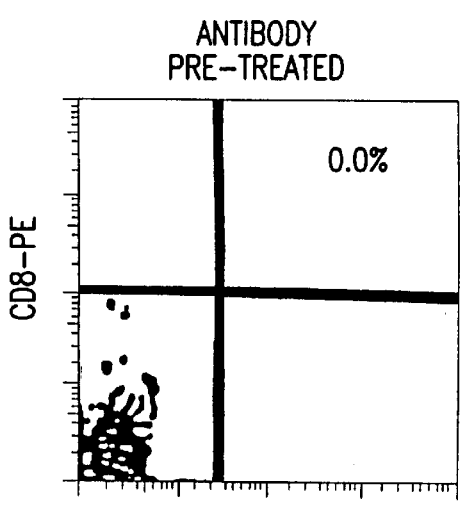

FIG. 11 Percentage of allogeneic donor cell engraftment in mice treated with: 1=3Gy TBI, 2=ALG (2 mg)+3Gy TBI, 3=3Gy TBI+CyP (200 mg/kg), 4=ALG (2 mg)+CyP (200 mg/kg), 5=ALG (2 mg)+3Gy TBI+CyP (200 mg/kg)

FIGS. 12 A–F Two-color staining for multilineage engraftment after CD4$^+$ and CD8$^+$ depletion pretreatment 4 months after bone marrow transplantation. The X axis shows staining with fluorescein-conjugated antibody against donor class I antigen (H2K$^k$). On the Y axis the staining for the different lineages with phycoerythrin-conjugated antibodies is shown (A: αβ TCR; B: CD4; C: CD8; D: NK1.1 (NK cells); E: B220 (B cells); F: MAC-1 (monocytes)). Percentages in right upper quadrants indicate donor-derived cells of each lineage in comparison with total cells in region analyzed.

FIGS. 13 A–D To confirm the adequacy of anti-CD4 and anti-CD8 pretreatment, PBLs were obtained from animals on day 3 after antibody pretreatment (day 0 for bone marrow transplantation) and stained with phycoerythrin-conjugated anti-CD4 and anti-CD8 antibodies. Percentage of CD4 (A, B) and CD8 (C, D) cells is shown for unmanipulated control (A, C) and representative depleted (B, D) animals. Percentages listed are cells staining positive of all cells in analyzed region (lymphoid gate).

Figure 14:
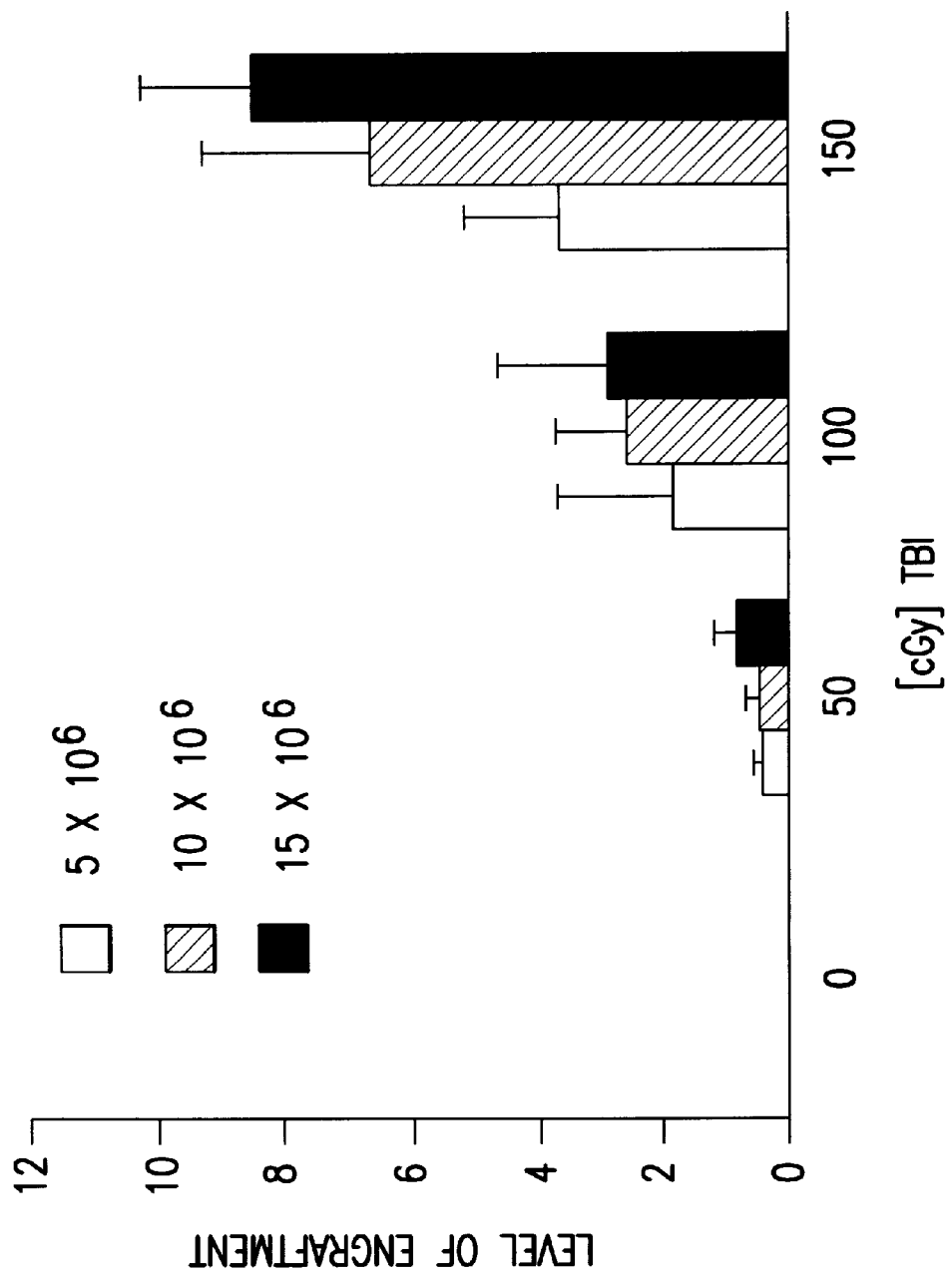

FIG. 14 Five, 10, or $15 \times 10^6$ untreated BM cells from 6.SJL-Ptprc$^3$Pep3b/Boy (Ly5a) donors (Ptprc$^a$) were transplanted to syngeneic C57BL/6J recipients (B6), conditioned with 0, 50, 100 or 150 cGy total body irradiation (TBI) (n=4 per group). The level of chimerism was determined 28 days after BMT. As expected, no engraftment occurred without irradiation. With 50 cGy irradiation 2 of 4 animals transplanted with 5 or $10 \times 10^6$ cells, respectively, engrafted at levels just at the threshold of sensitivity of flow cytometric analyses (0.4%). 100% of the animals conditioned with 50 cGy engrafted, when transplanted with $15 \times 10^6$ cells. At irradiation doses >50 cGy 100% of the animals engrafted, regardless of the cell dose, but the level of engraftment appeared to correlate with the donor cell dose.

Figure 15:
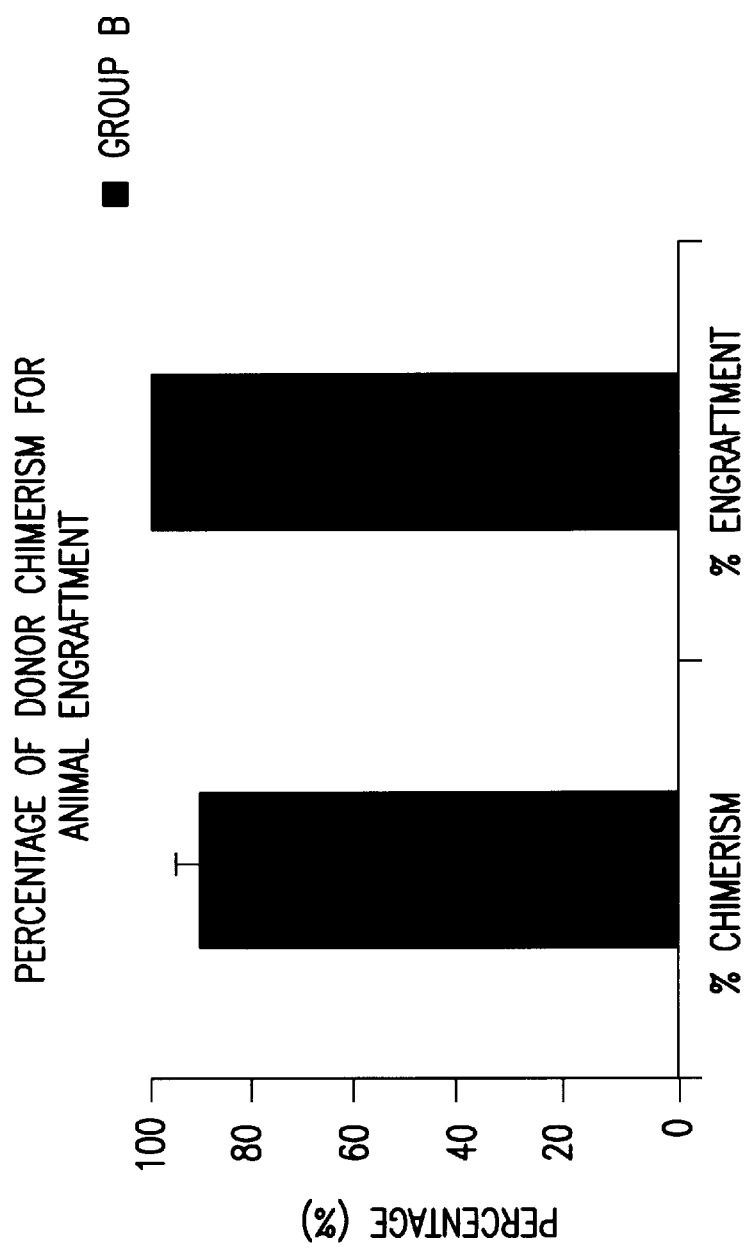

FIG. 15 NOD mice were treated with two different conditioning approaches and then transplanted with $60 \times 10^6$ unmodified B10.BR bone marrow cells: A) 600 cGy total body irradiation (TBI) alone; B) 600 cGy TBI followed by a single intraperitoneal injection of 50 mg/kg of Cyclophosphamide (CyP) two days after bone marrow transplantation. There was no engraftment with radiation alone (Group A n=10), while in group B there was 100% engraftment with a 91.5% donor chimerism.

Figure 16:
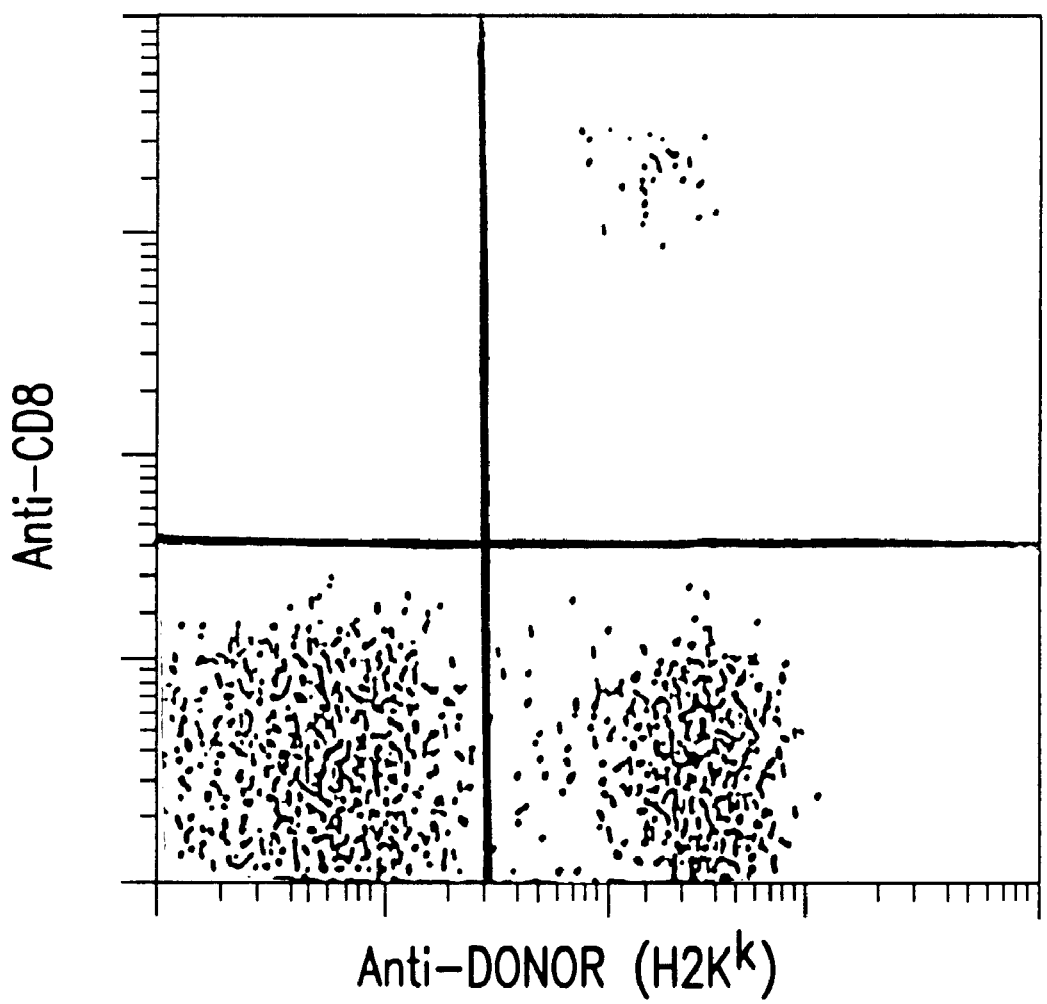
Figure 17A:
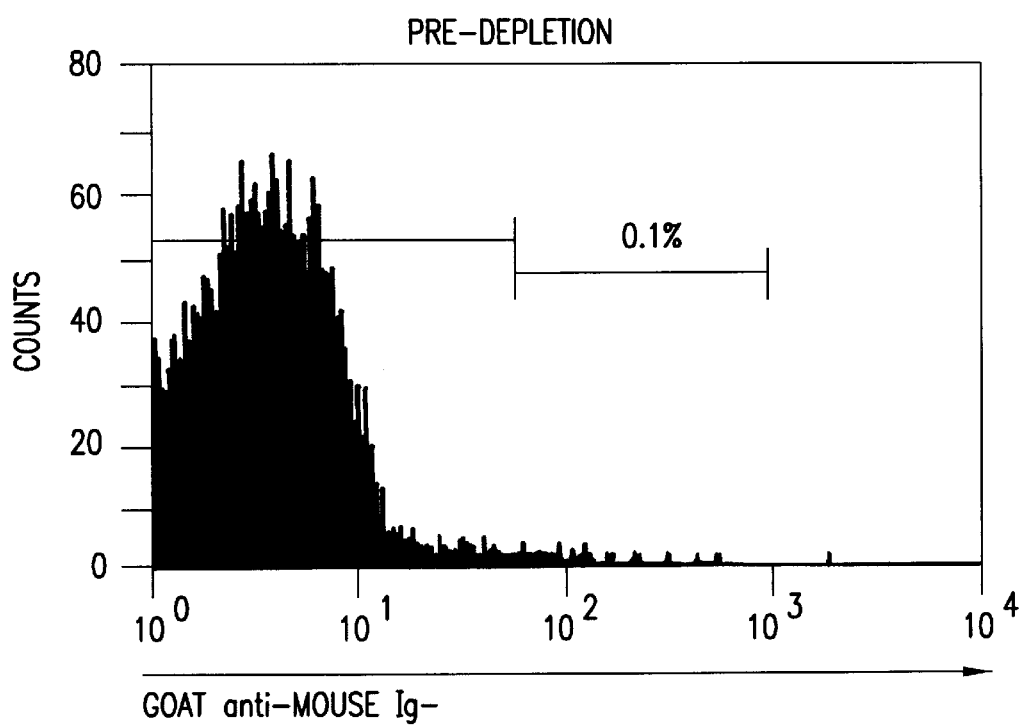
Figure 17B:
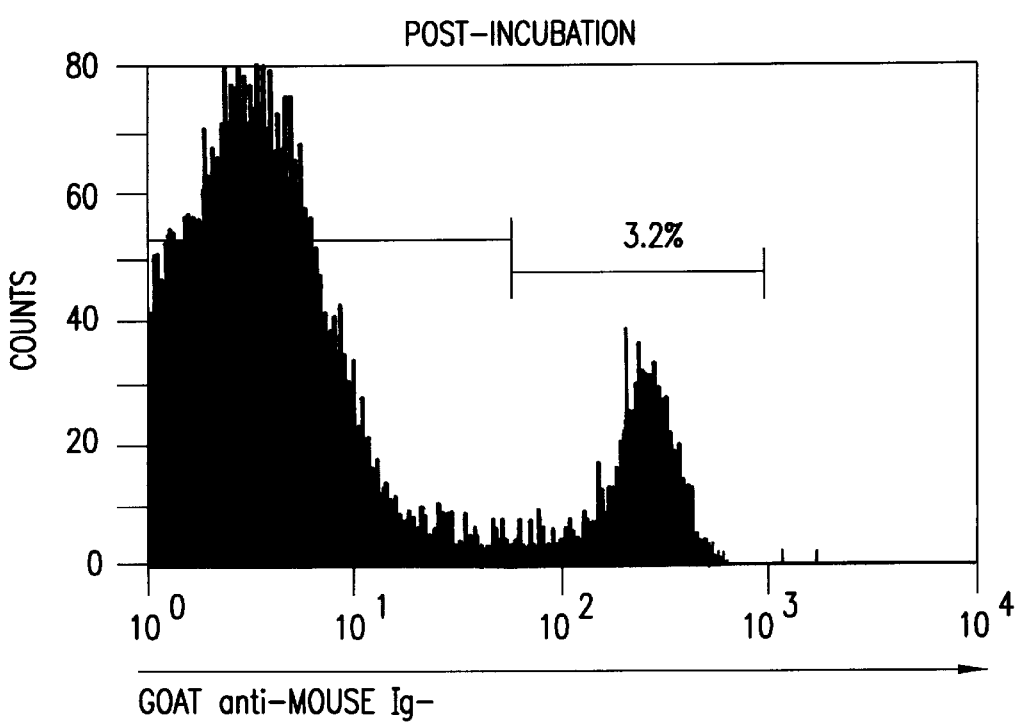
Figure 17C:
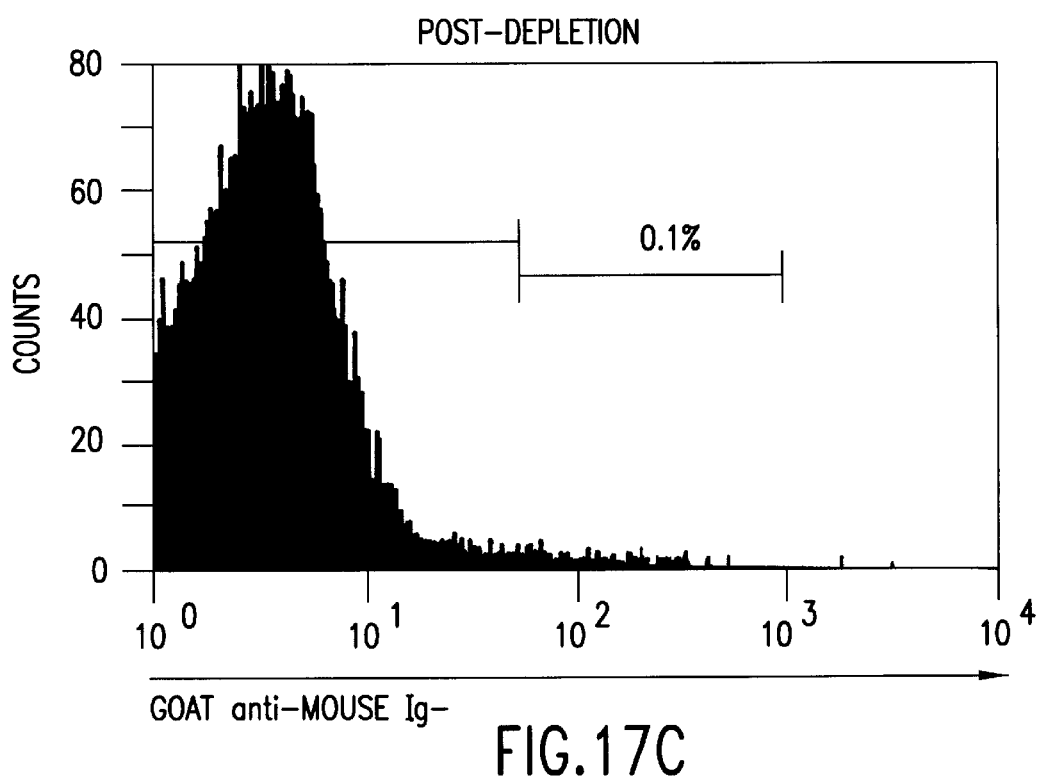
Figure 17D:
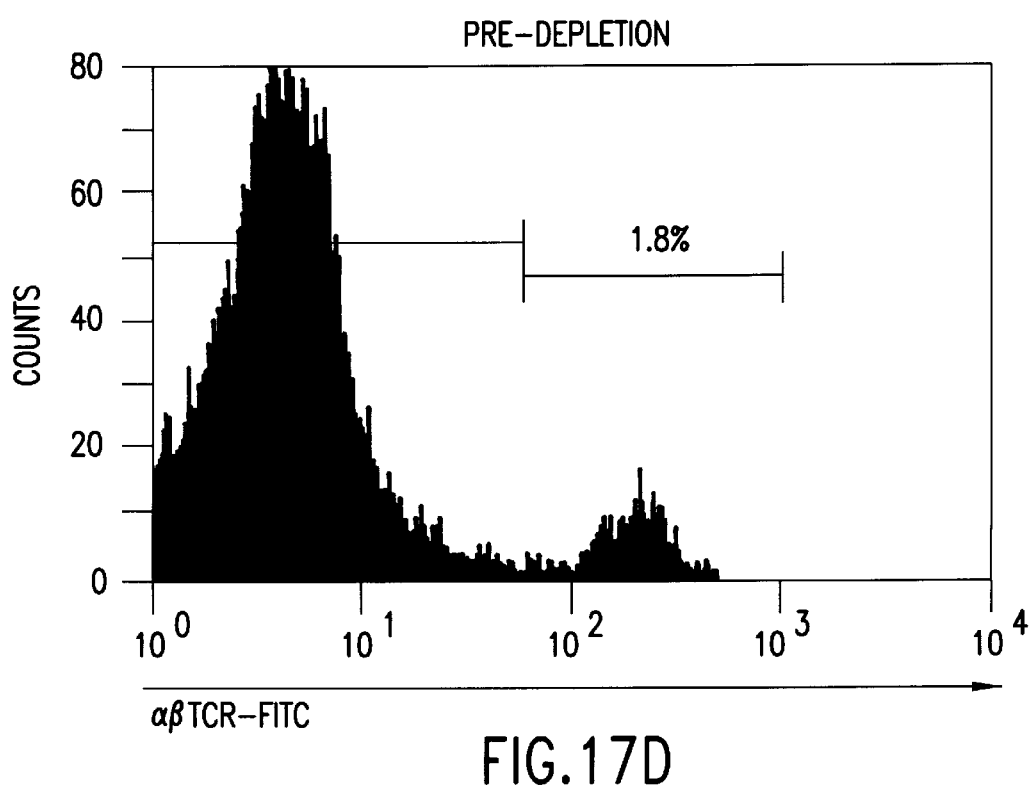
Figure 17E:
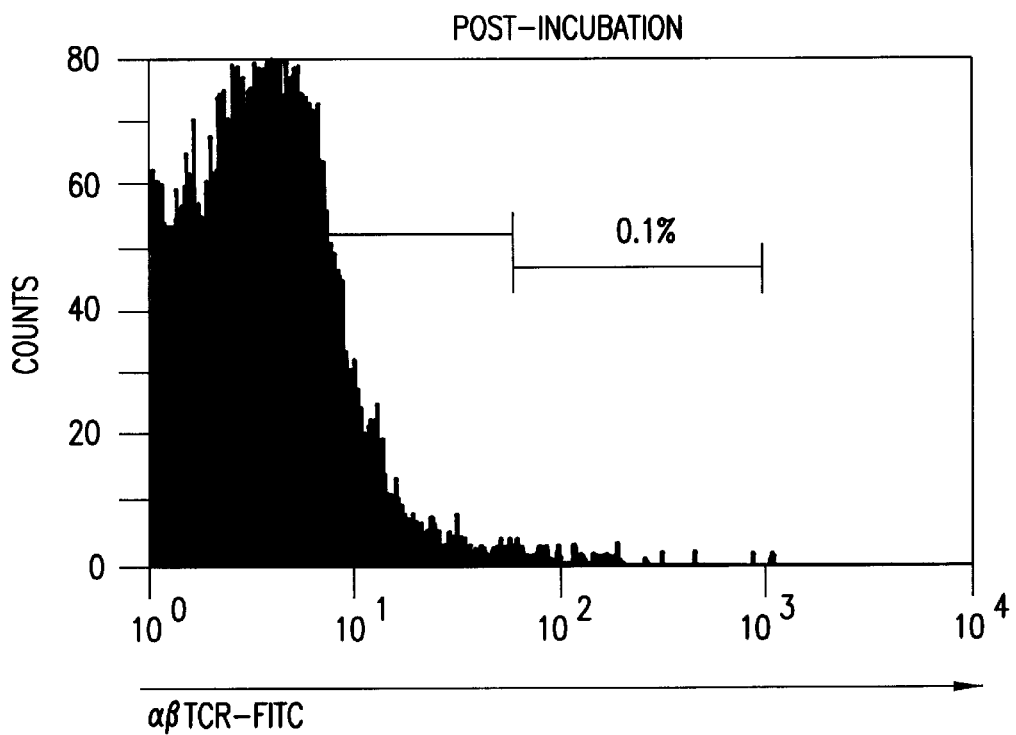
Figure 17F:
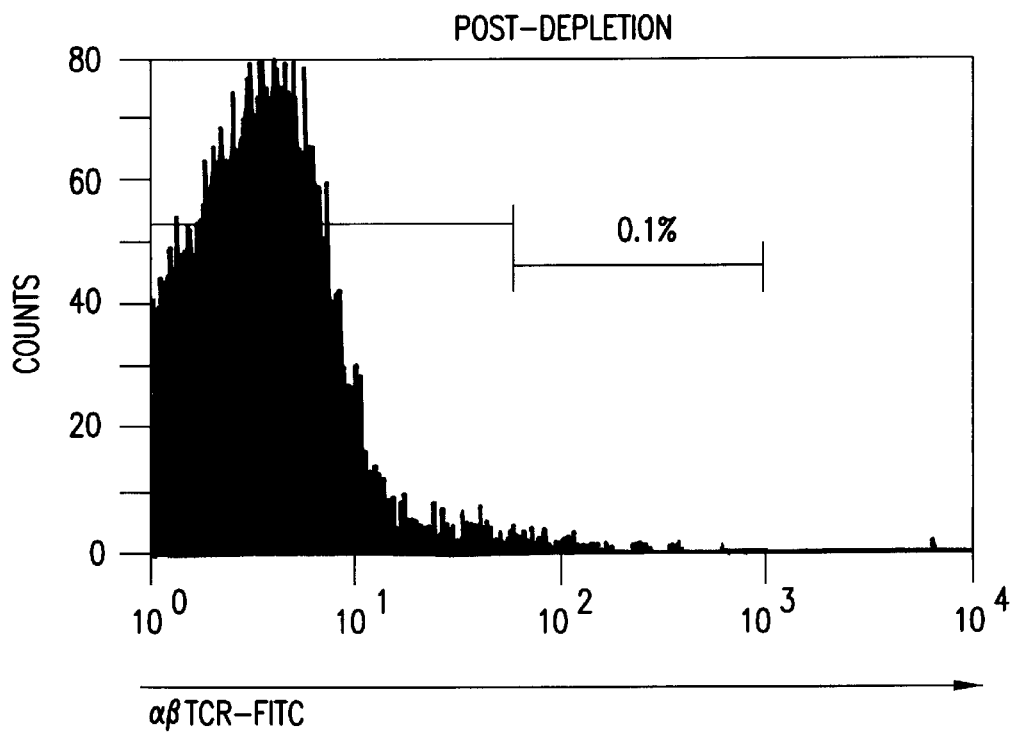
Figure 18A:
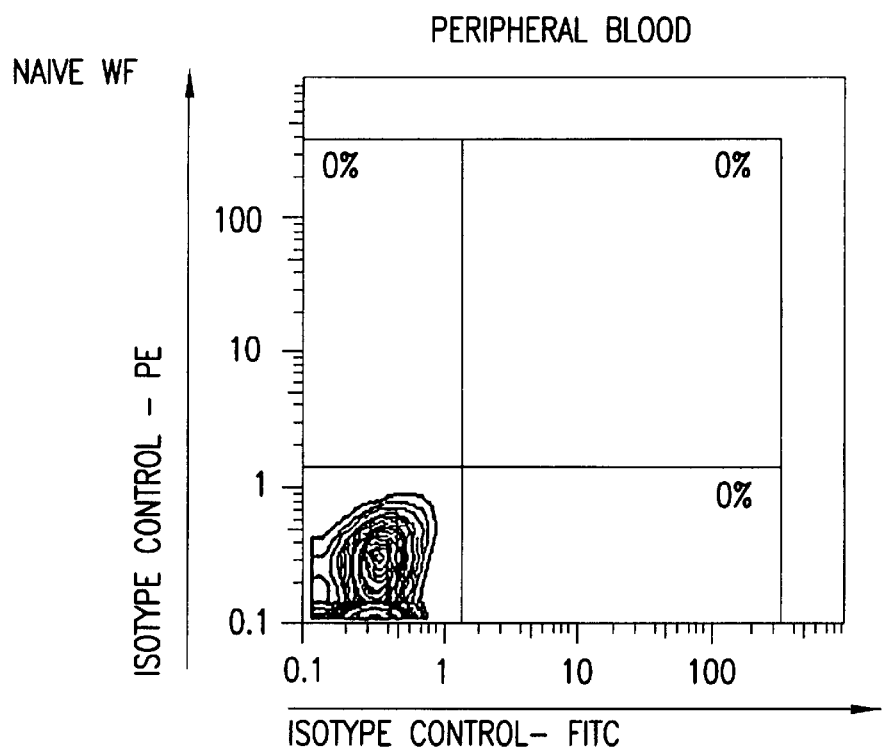
Figure 18B:
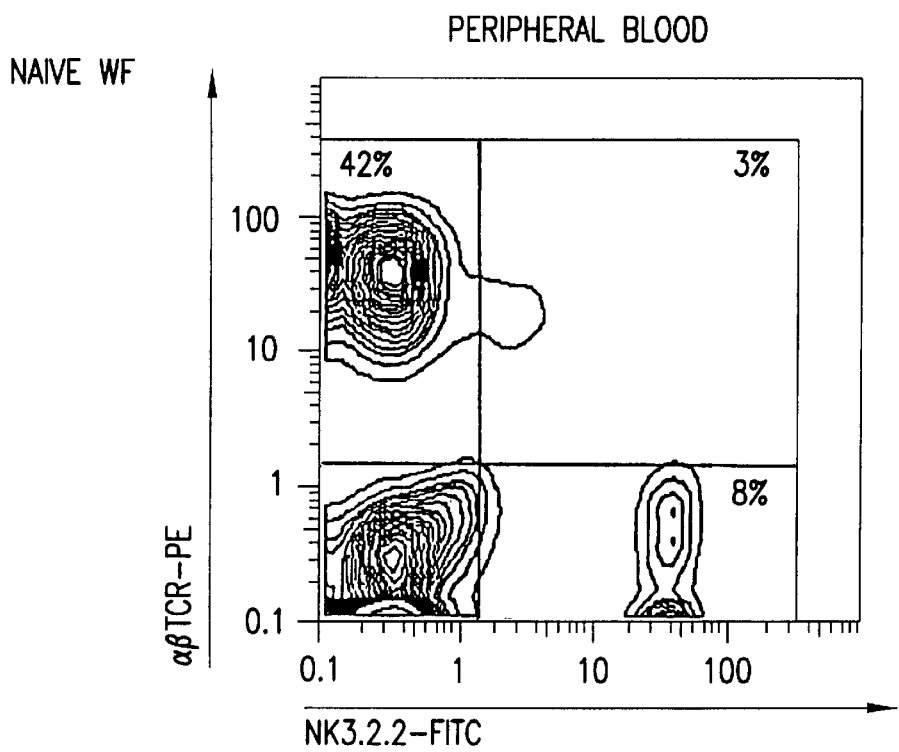
Figure 18C:
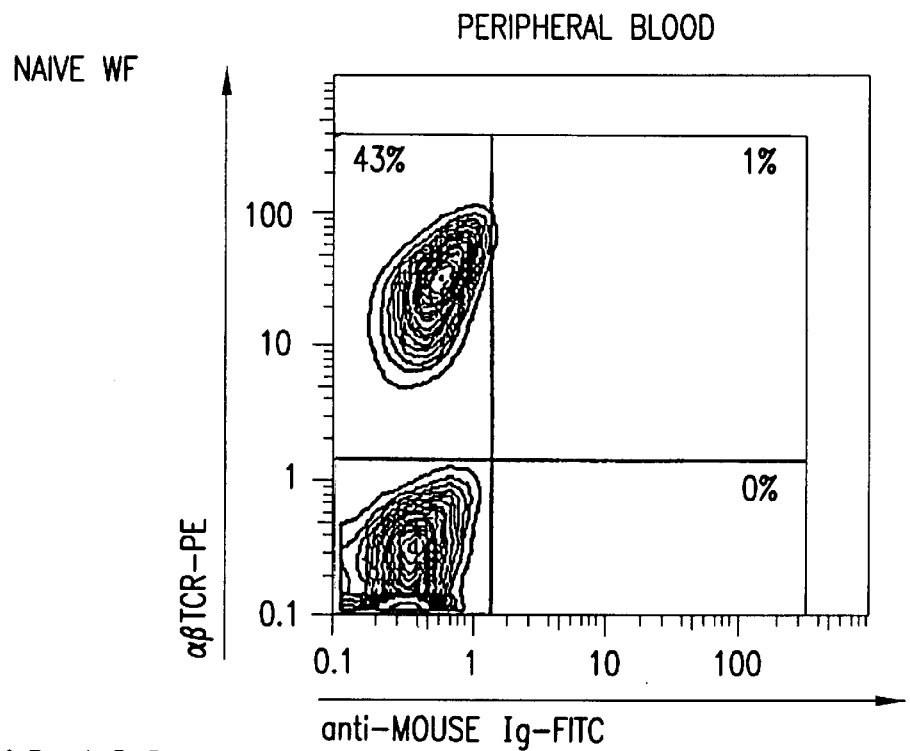
Figure 18D:
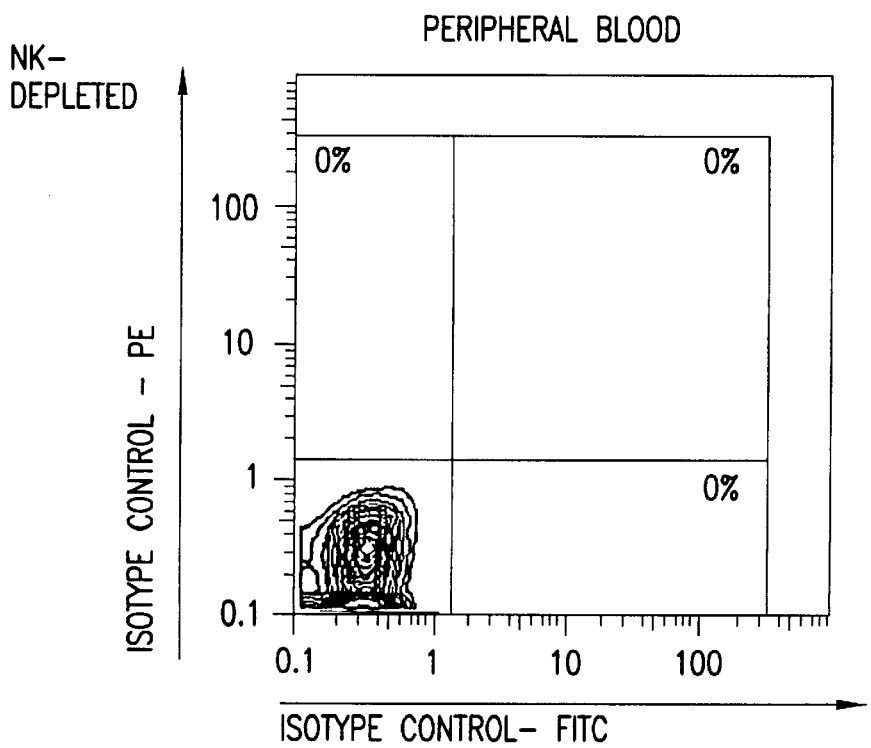
Figure 18E:
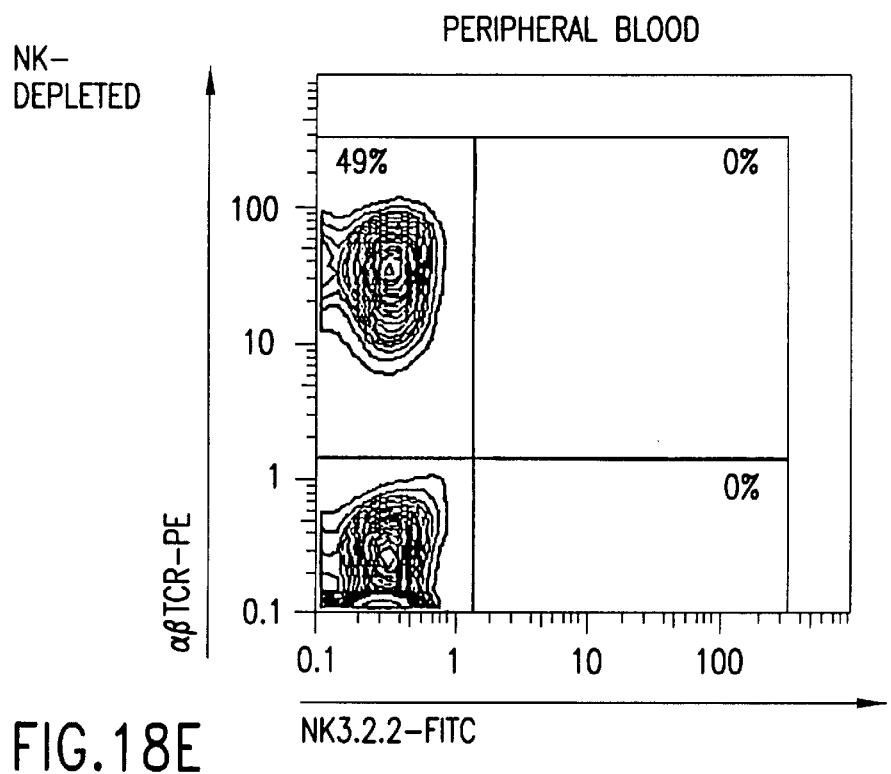
Figure 18F:
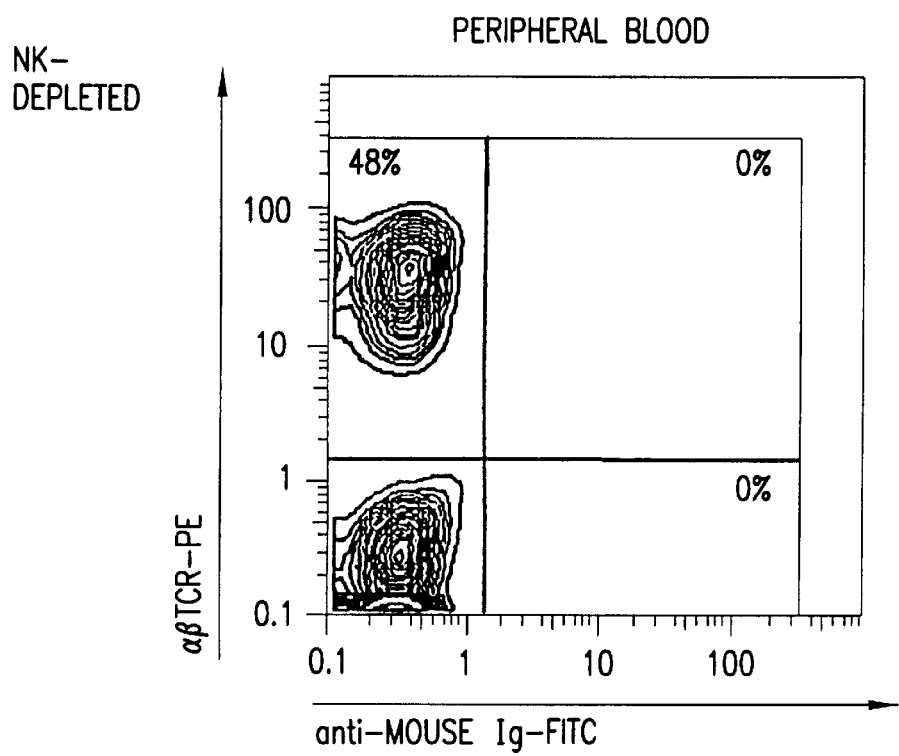
Figure 19A:
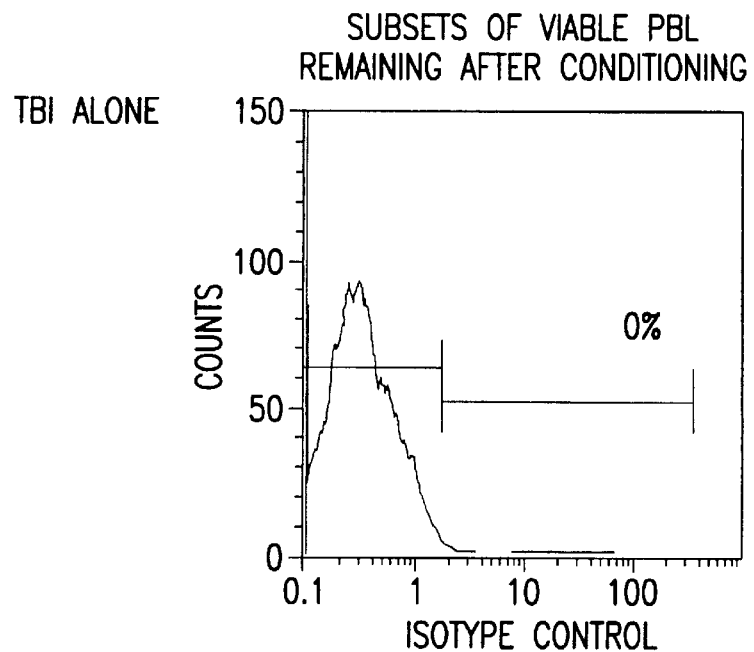
Figure 19B:
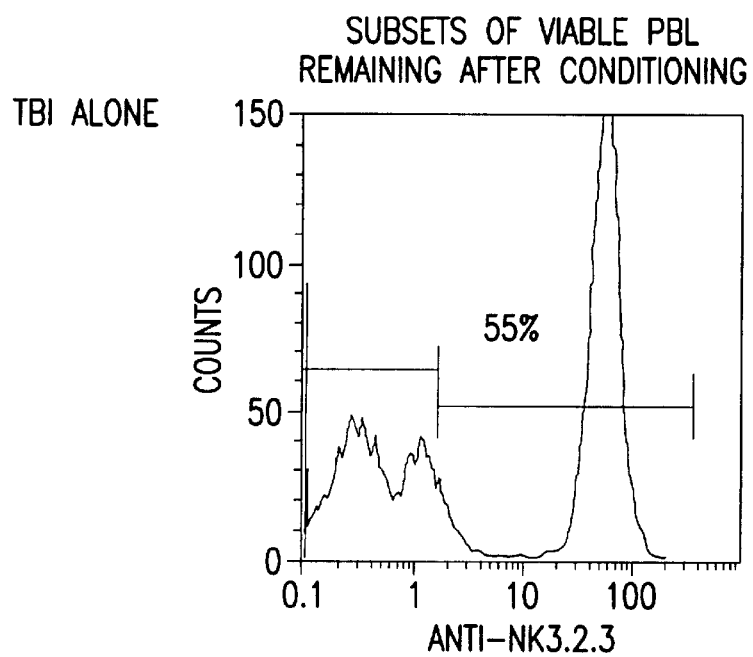
Figure 19C:
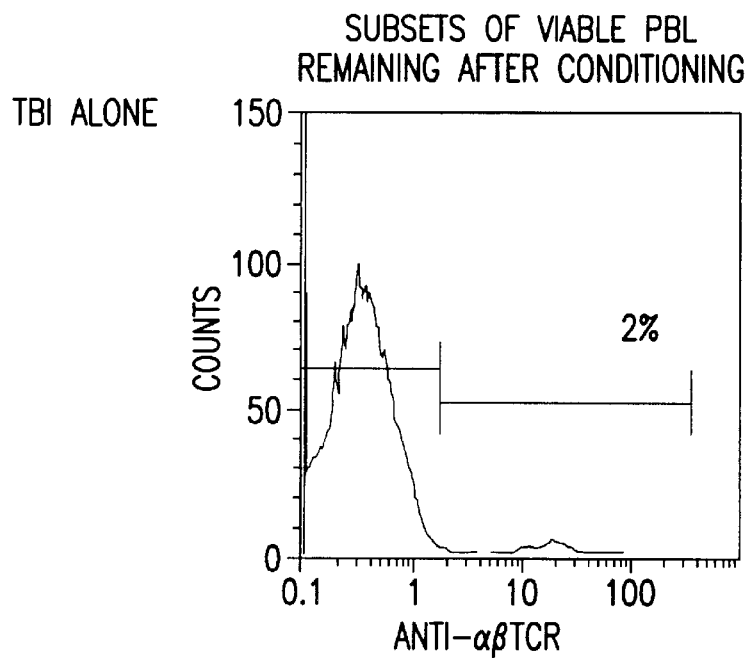
Figure 19D:
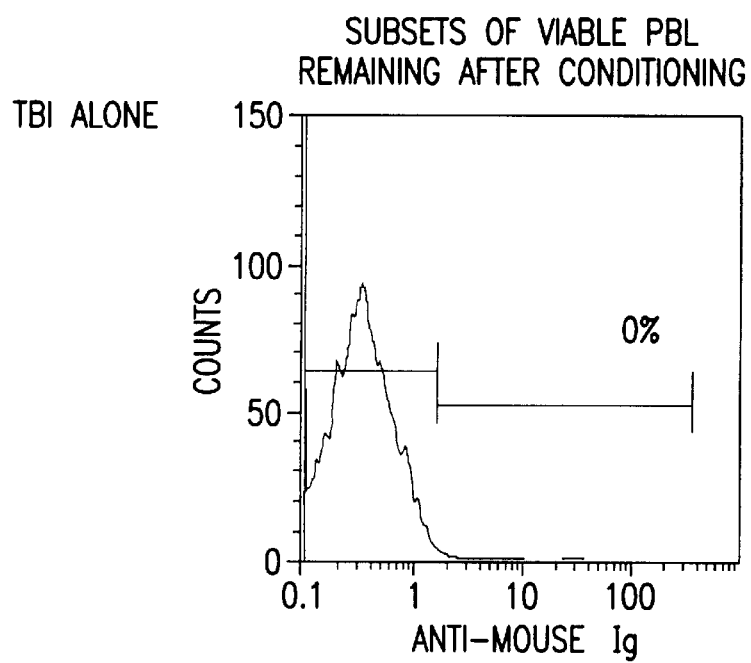
Figure 19E:
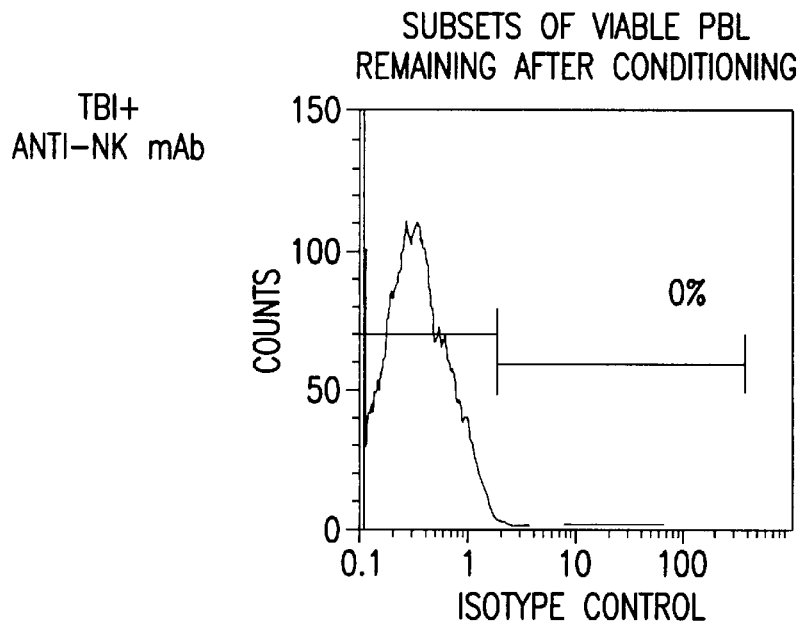
Figure 19F:
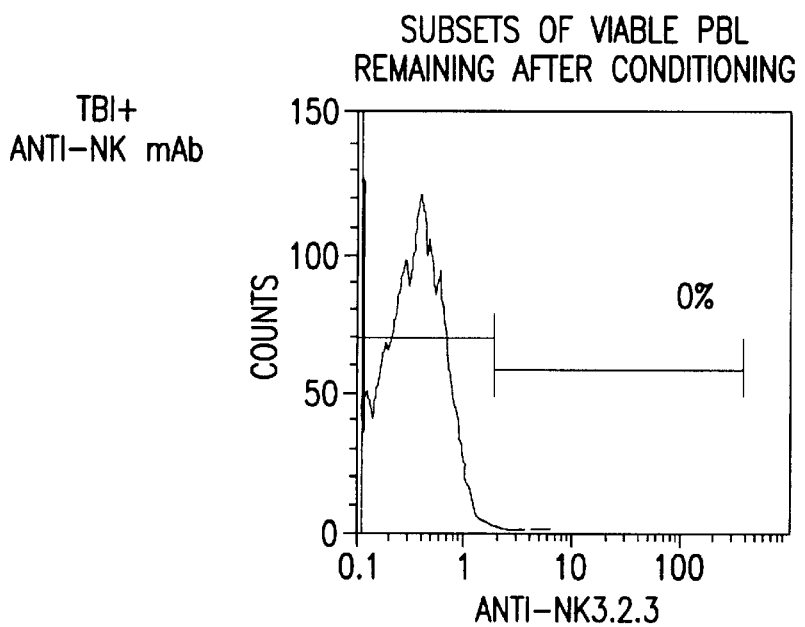
Figure 19G:
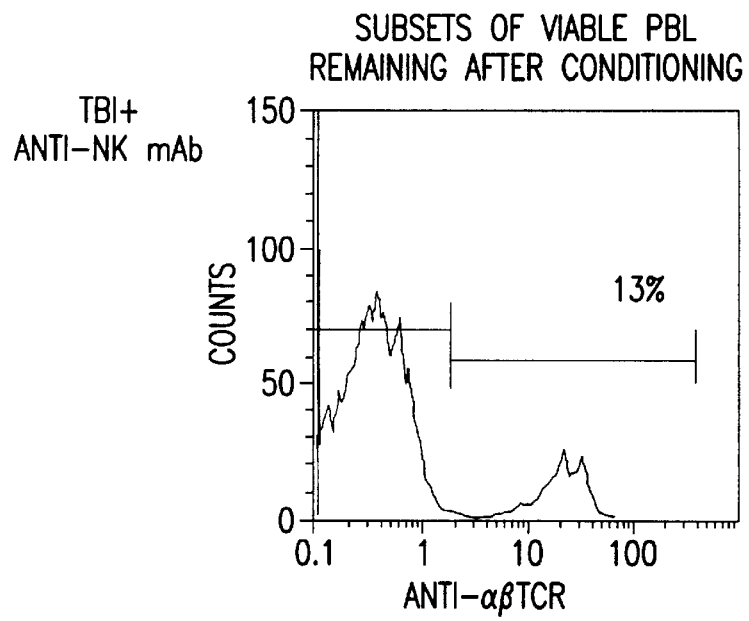
Figure 19H:
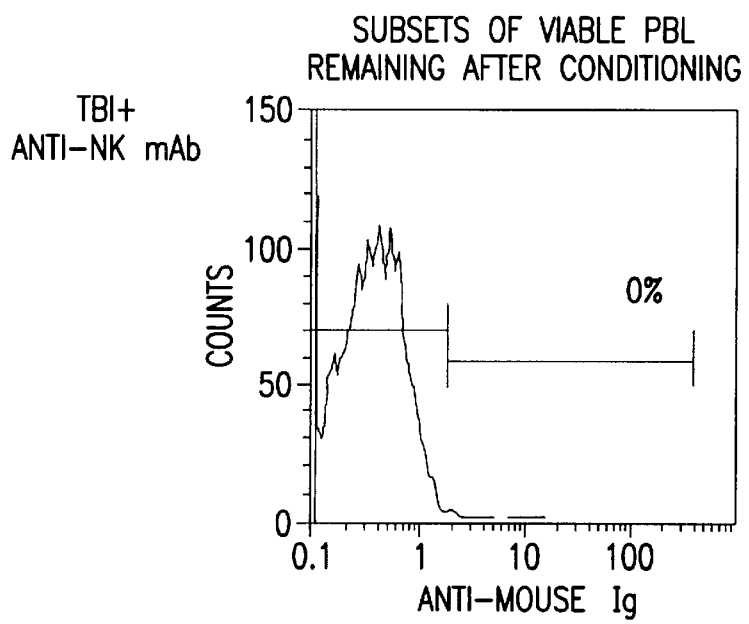
Figure 19I:
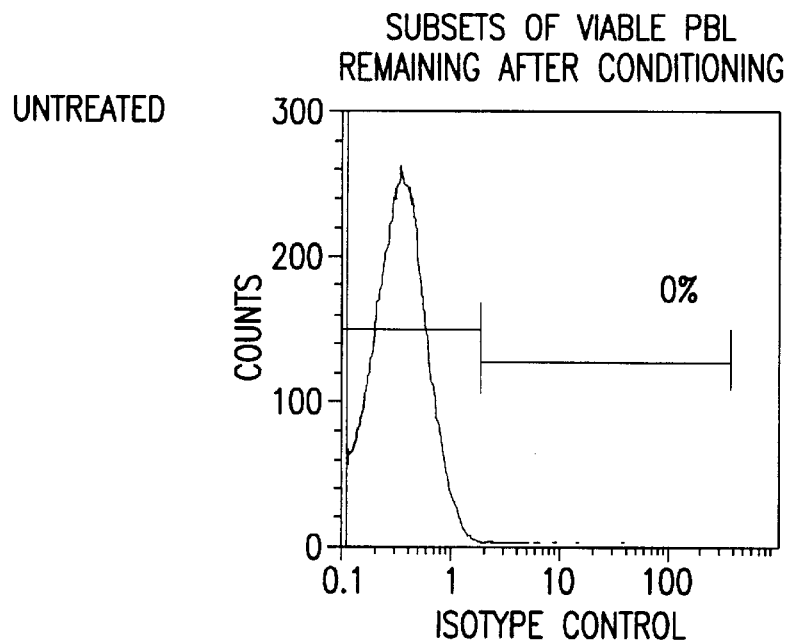
Figure 19J:
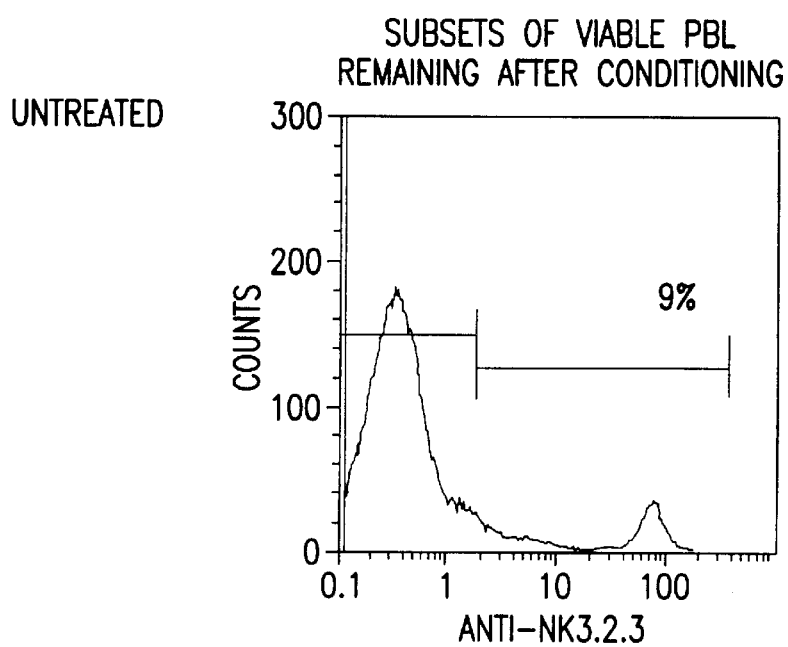
Figure 19K:
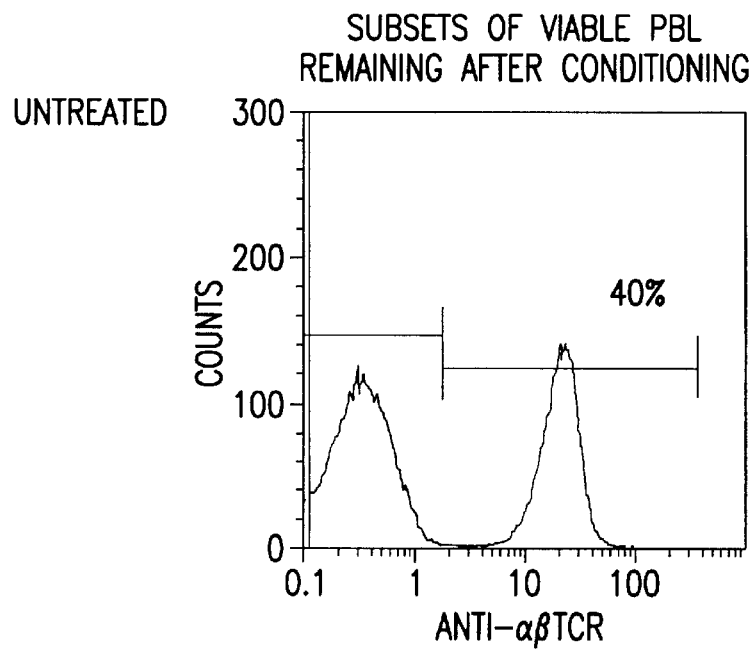
Figure 19L:
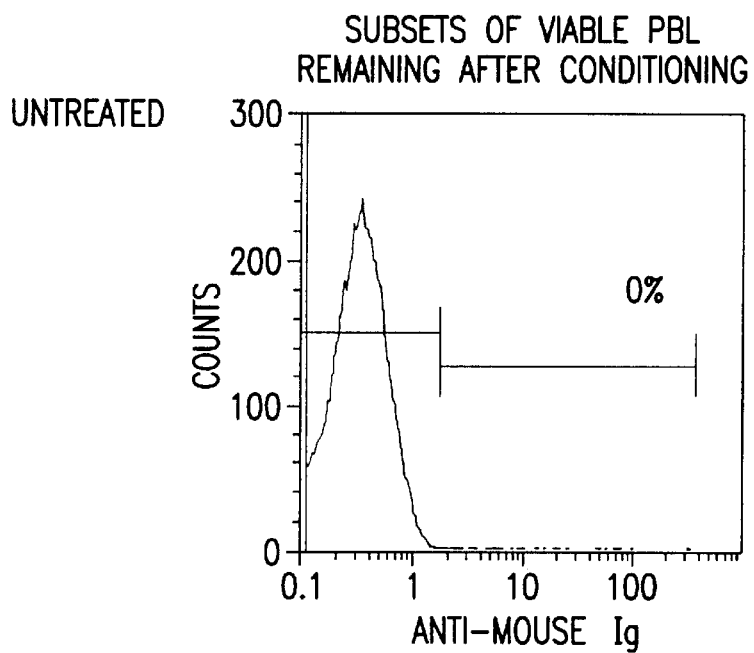
Figure 20A:
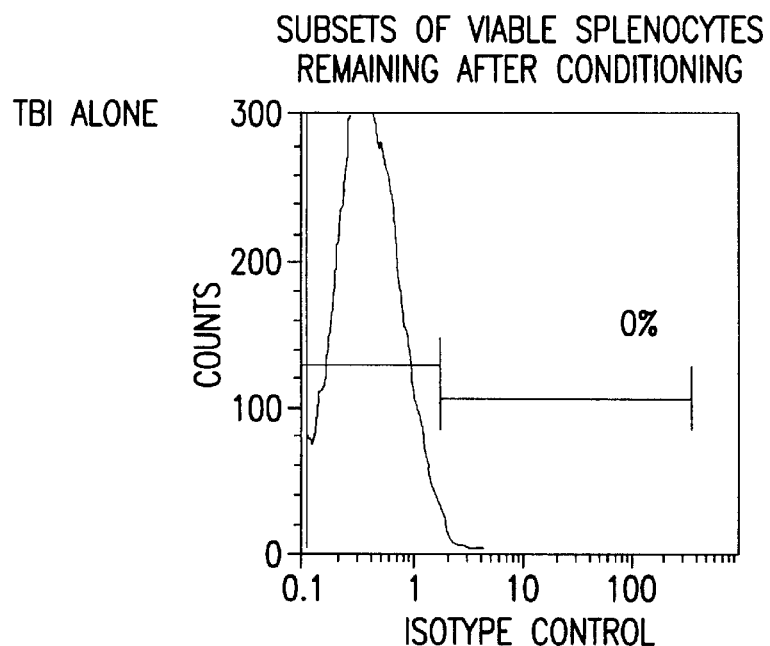
Figure 20B:
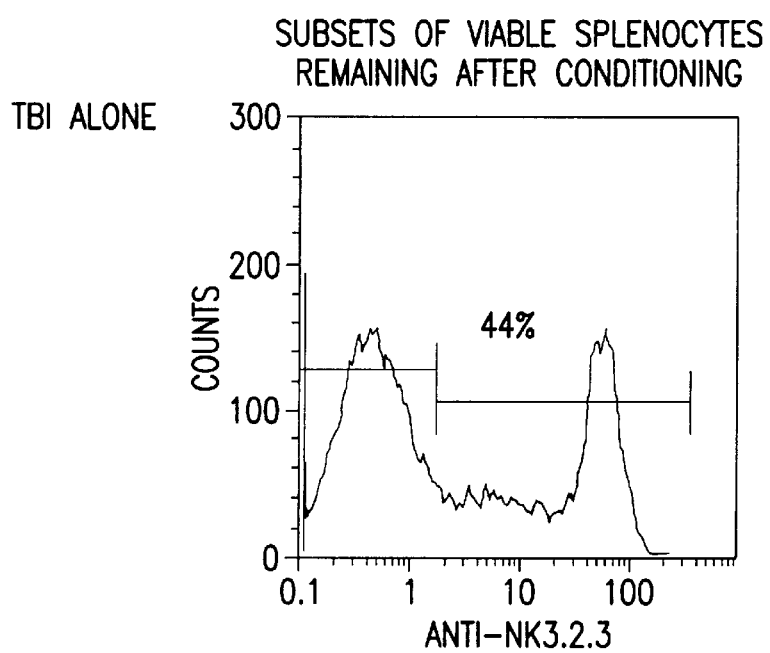
Figure 20C:
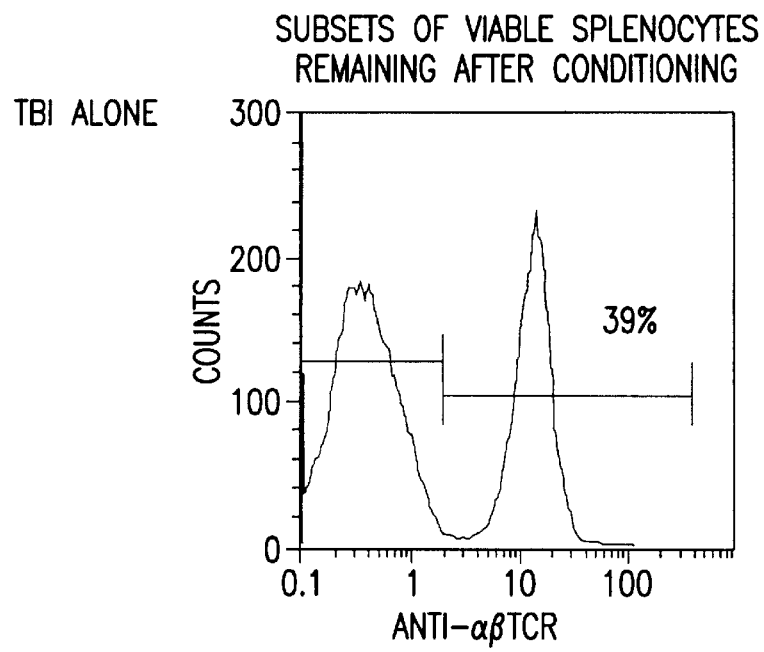
Figure 20D:
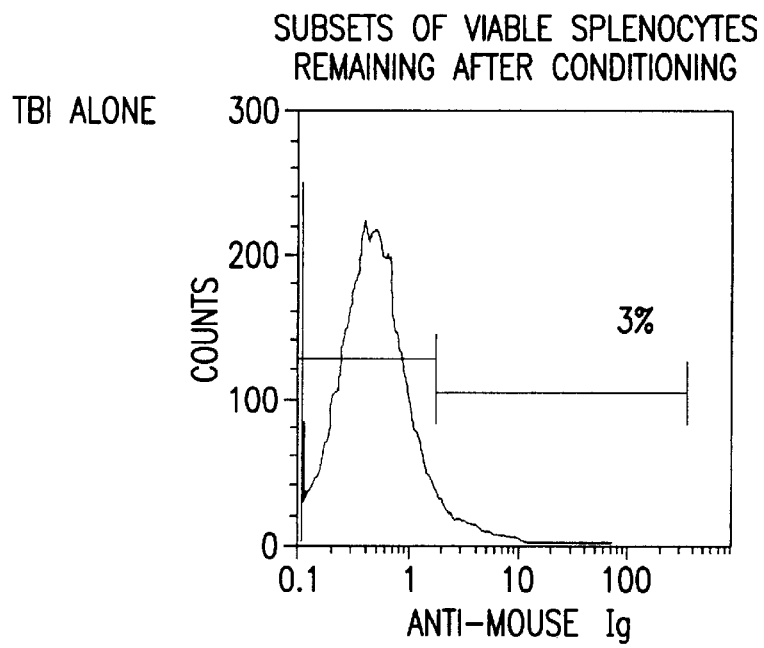
Figure 20E:
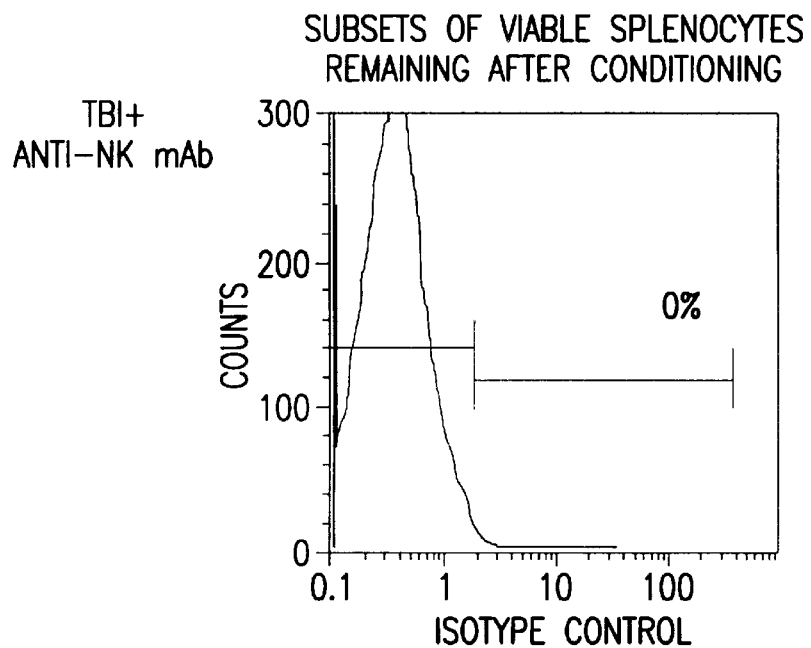
Figure 20F:
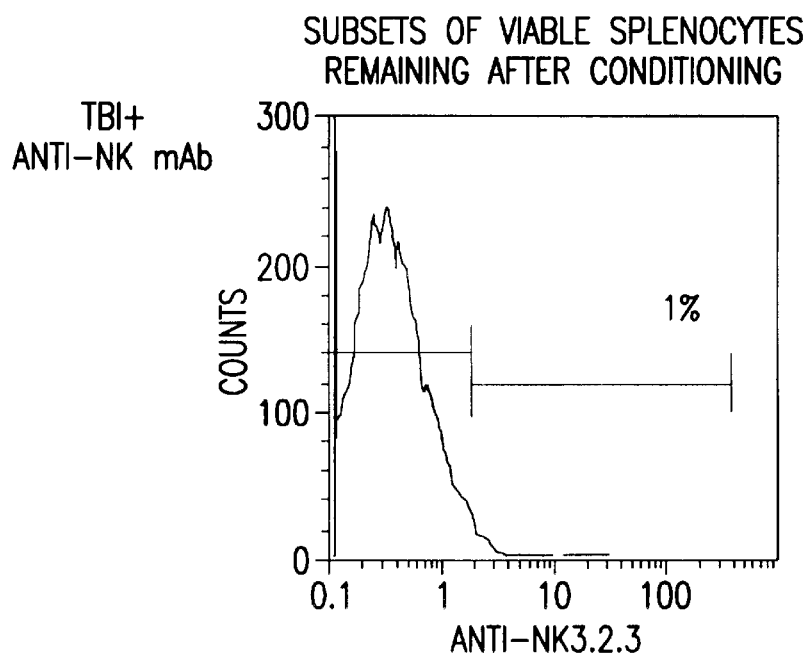
Figure 20G:
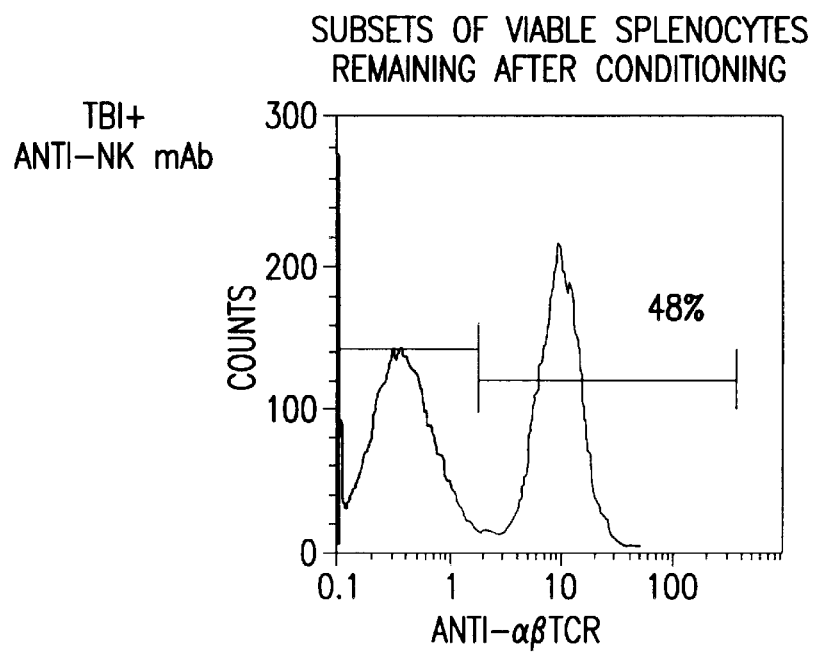
Figure 20H:
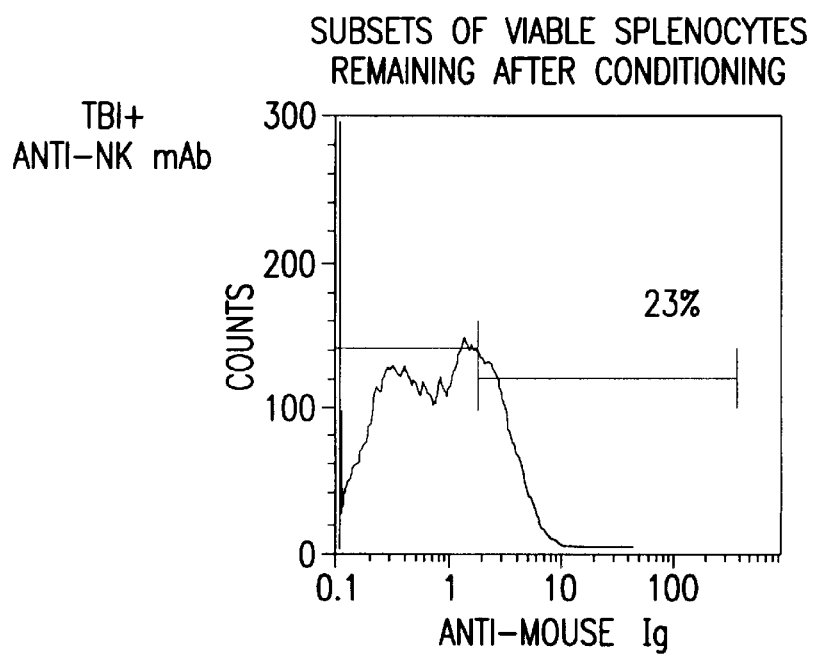
Figure 20I:
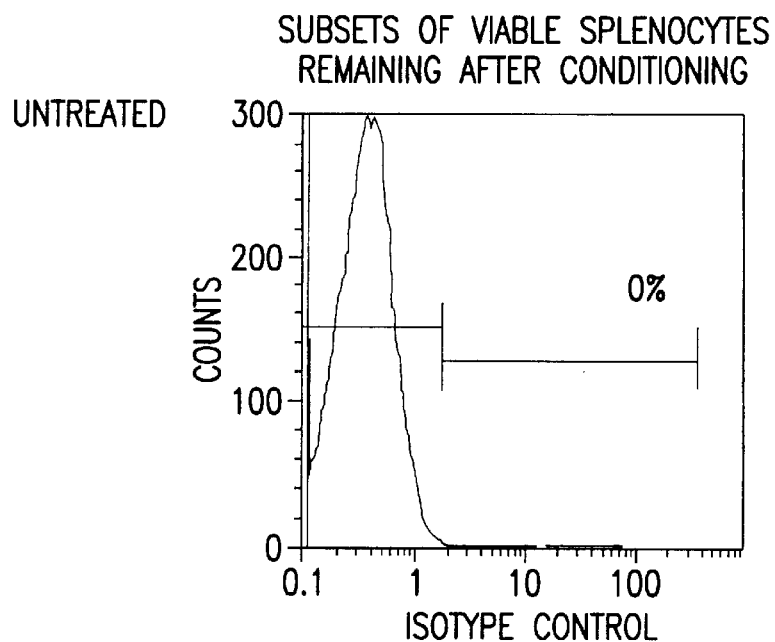
Figure 20J:
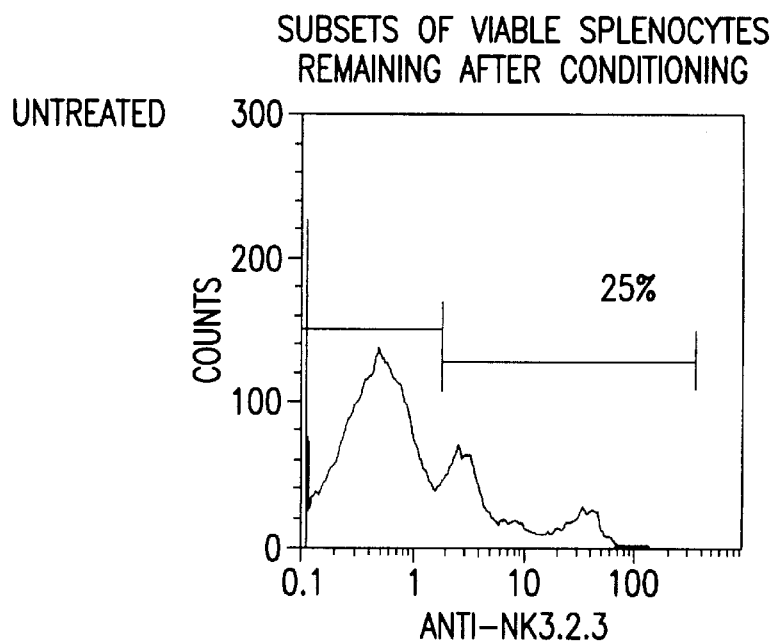
Figure 20K:
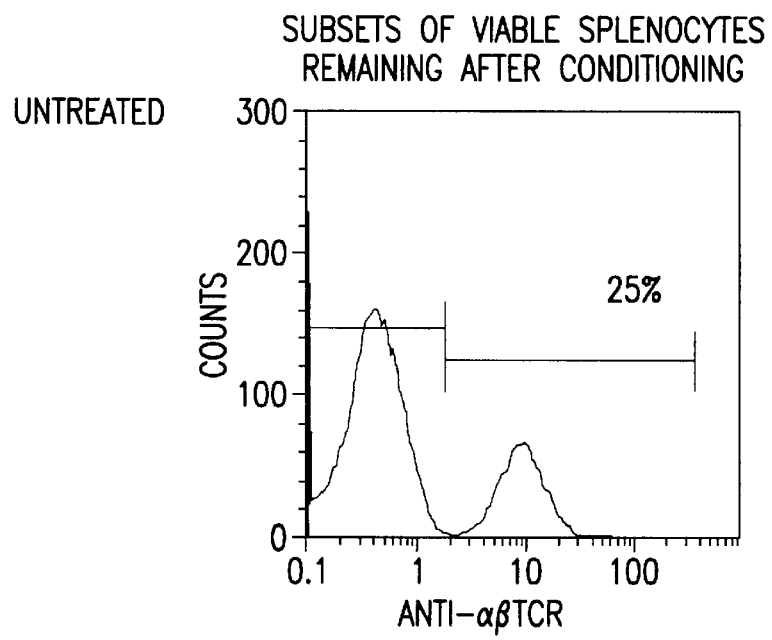
Figure 20L:
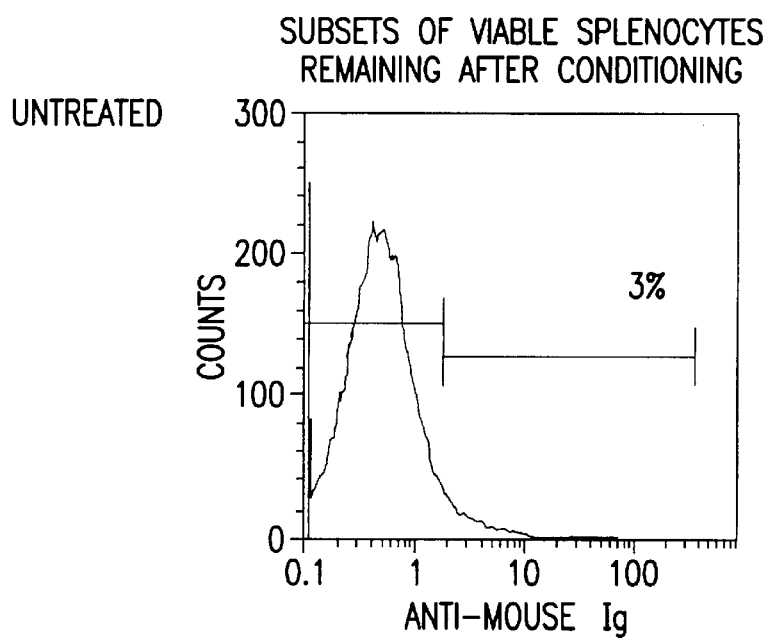
Figure 21A:
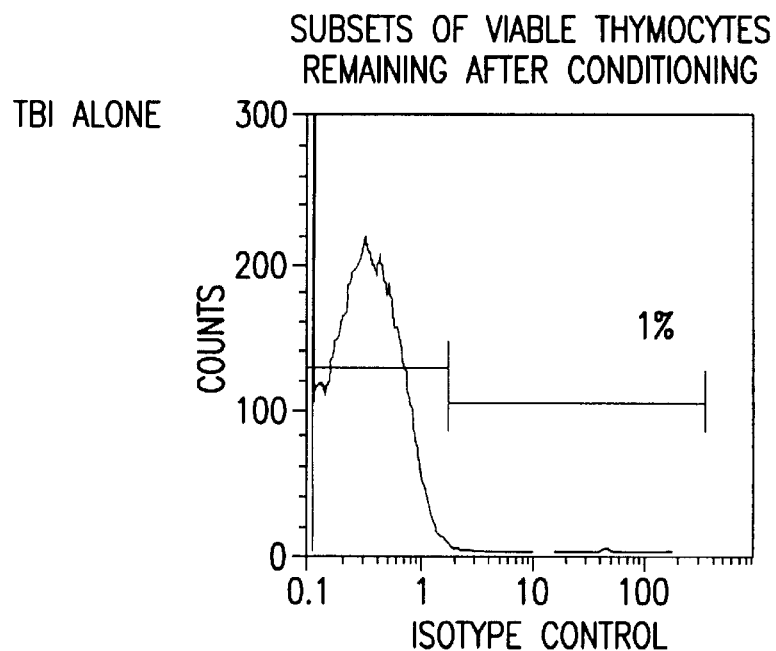
Figure 21B:
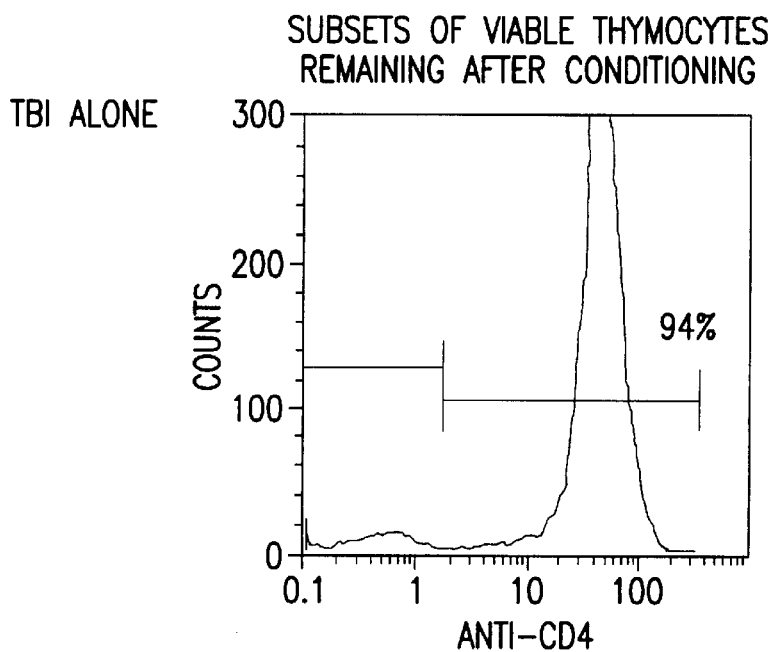
Figure 21C:
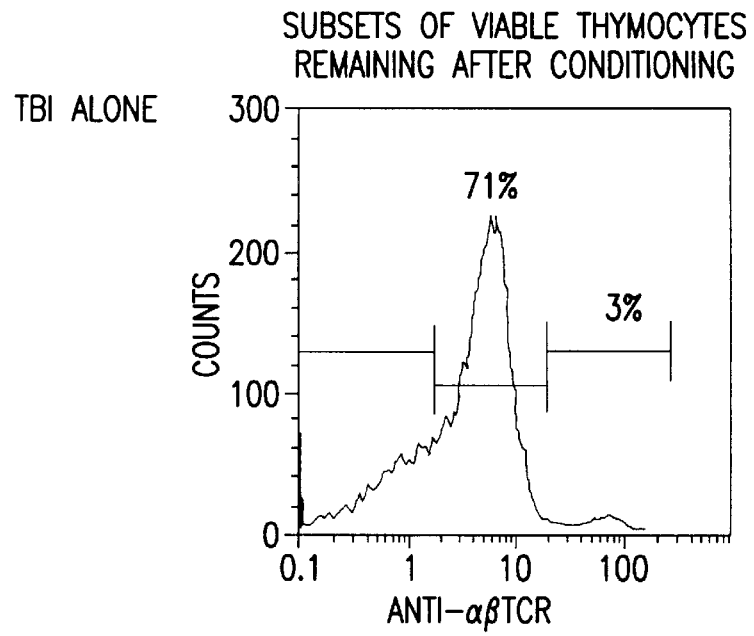
Figure 21D:
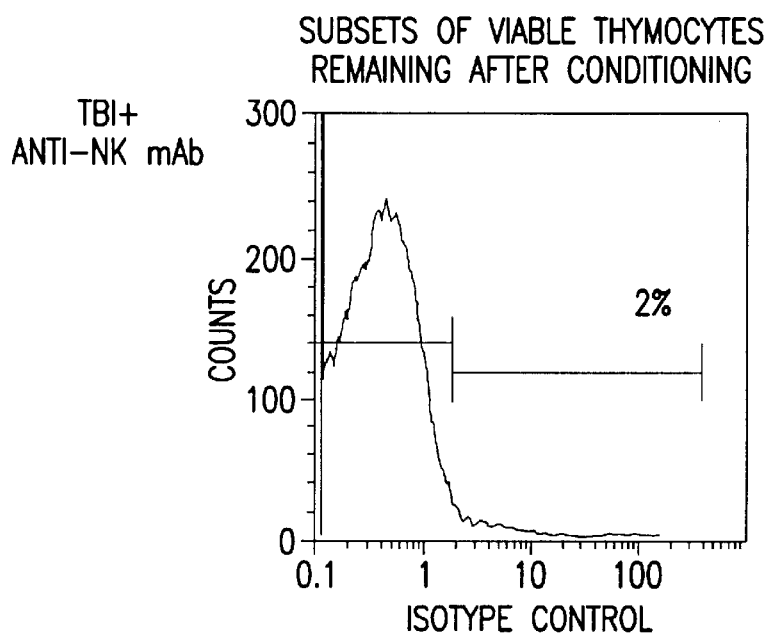
Figure 21E:
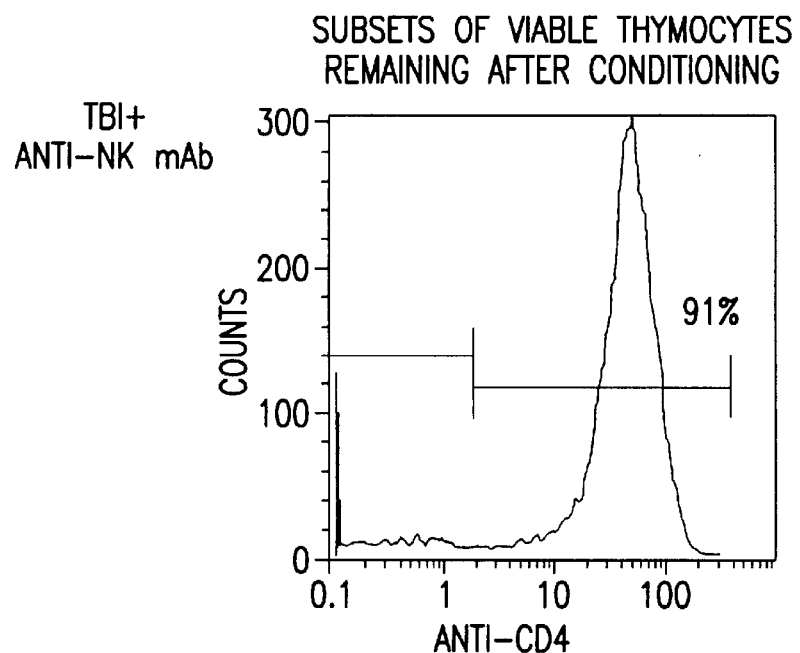
Figure 21F:
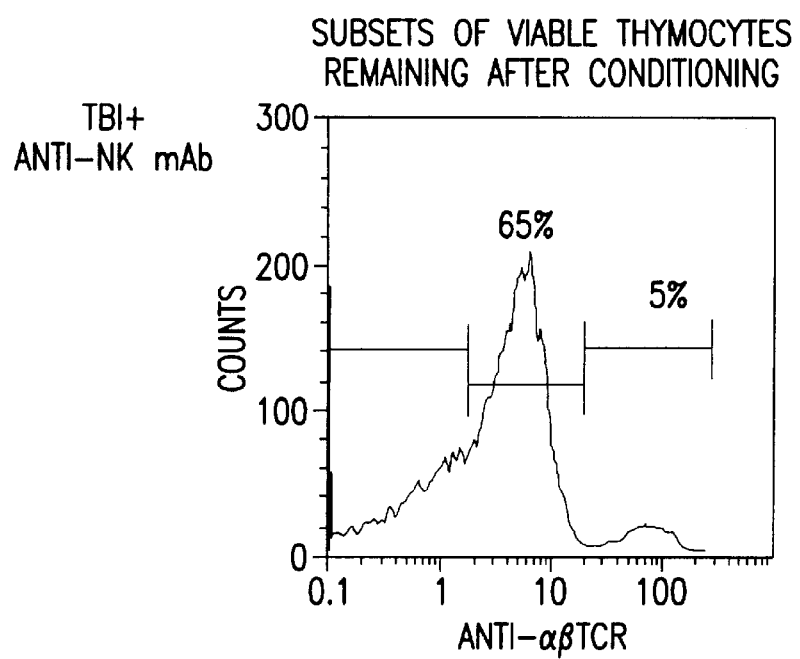
Figure 21G:
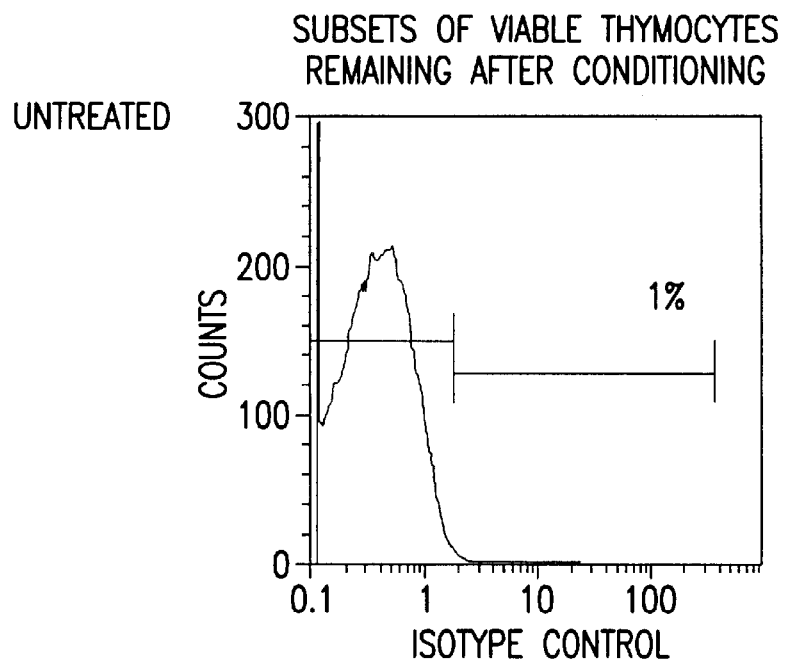
Figure 21H:
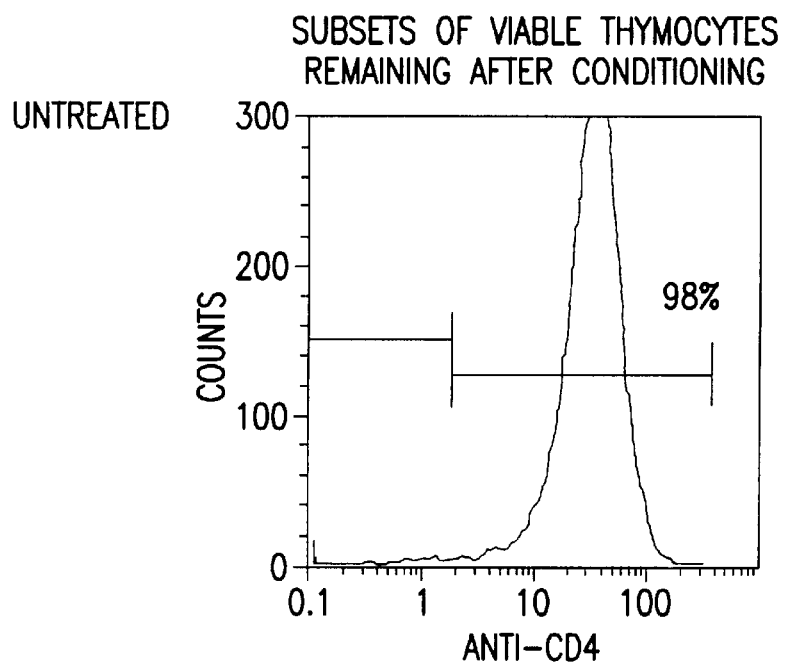
Figure 21I:
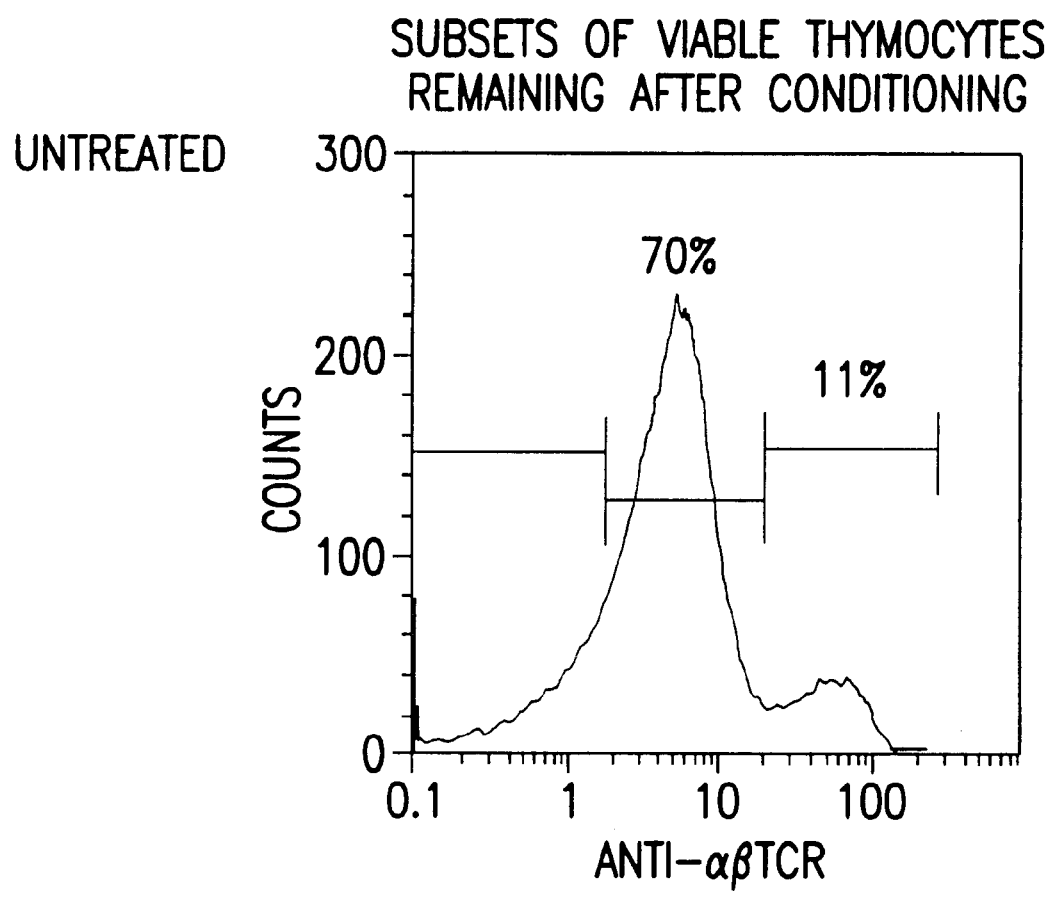

FIG. 16 C57BL/6-Cd4$^{Tm/mak}$ (CD4-KO) and C57BL/6-Cd8$^{Tm/mak}$ (CD8-KO) mice were conditioned with 300 cGy TBI, transplanted with $15 \times 10^6$ B10.BR/SnJ bone marrow cells, and received 200 mg/kg CyP 2 days after bone marrow transplantation (BMT). Chimerism was assessed by flow cytometry 28 days and 4 months after BMT with mAb against donor (H2K$^k$) and host (H2K$^b$) MHC class I antigens. All CD8-KO mice engrafted at this low level of irradiation (n=16). CD8-KO mice showed a clear population of CD8$^+$ cells of donor origin at 4 months post-BMT, while no CD8$^+$ cells of recipient origin were detectable.

FIG. 17 Flow cytometric analysis confirming efficacy of T cell depletion using anti-αβTCR mAb and immunomagnetic beads. (A) The percentage of αβTCR$^+$ T cells in untreated bone marrow was determined before depletion. (B) Labeling of the target cell population with purified anti-αβTCR mAb was assessed after incubation with secondary anti-mouse Ig-FITC mAb. (C) Efficacy of depletion of αβTCR$^+$ T cells was confirmed by staining of T cell depleted ("TCD") bone marrow cells with anti-αβTCR-FITC as well as FITC-labeled secondary mAb.

FIG. 18 In vivo depletion of NK cells assessed in the peripheral blood of Wistar Furth ("WF") rats by two-color-flow cytometry. WF rats received anti-NK mAb IP on days −3 and −2. PB from anti-NK mAb treated (n=6) and untreated (n=2) recipients was obtained on day 0 before TBI. (A-C) In naive WF rats 8% of PBL showed NK3.2.3$^{bright}$ staining while 3% presented a T/NK cell phenotype (NK3.2.3$^{dim}$/αβTCR+). (D-F) Complete depletion of NK cells was observed in PB after treatment with anti-NK mAb.

FIG. 19 Presence of viable T cells and NK cells in peripheral blood after conditioning with TBI alone or anti-NK mAb plus TBI was assessed by two-color-flow cytometry. (A) Peripheral blood was obtained from untransplanted WF rats on day +1 after conditioning with 900 cGy TBI alone on day 0 or (B) pretreatment with anti-NK mAb on days −3 and −2 plus 900 cGy TBI on day 0. (C) Untreated WF rats served as controls. PBL were stained with directly conjugated anti-NK or anti-αβTCR mAb. Cells were also stained with secondary anti-mouse mAb to detect cells coated with anti-NK mAb. Gating of PBL was performed based on forward and side scatter and dead cells were excluded by staining with propidium iodide (PI). Histograms show results from one representative animal of each group (n=4). The percentages of PI negative PBL are presented.

FIG. 20 Assessment of viability of T cells and NK cells in spleen of WF rats after conditioning with TBI alone or anti-NK mAb plus TBI. (A) Spleens were harvested from untransplanted WF rats on day +1 after conditioning with 900 cGy TBI alone on day 0 or (B) pretreatment with anti-NK mAb on days −3 and −2 followed by 900 cGy TBI on day 0. (C) Splenocytes from untreated WF rats served as controls. Splenocytes were stained with directly conjugated anti-NK, anti-apTCR or secondary anti-mouse Ig mAb. Cells were gated based on forward and side scatter and propidium iodide (PI) positive cells were excluded. Histograms show results from one representative animal of each group (n=4). The percentages of PI negative lymphocytes are presented.

FIG. 21 Flow cytometric analysis of thymocytes from untreated WF rats or after conditioning with TBI alone or anti-NK mAb plus TBI. (A) Thymus was harvested from untransplanted WF rats on day +1 after conditioning with 900 cGy TBI alone on day 0 or (B) pretreatment with anti-NK mAb on days −3 and −2 followed by 900 cGy TBI on day 0. (C) Thymocytes from untreated WF rats served as controls. Nonviable thymocytes were excluded by gating out propidium iodide (PI) positive cells. Histograms show results from one representative animal of each group (n=4). The percentages of PI negative thymocytes are presented.

Figure 22A:
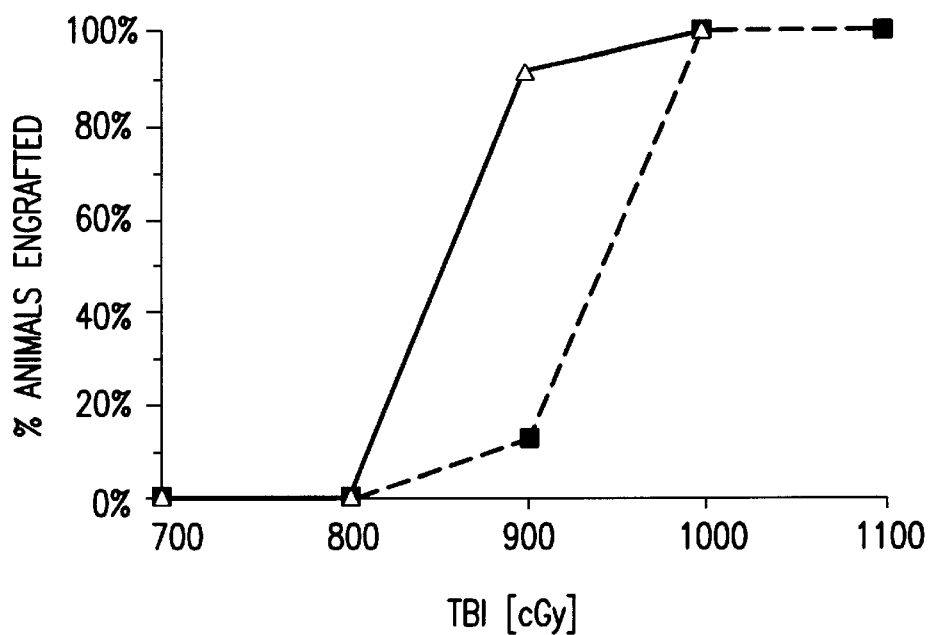
Figure 22B:
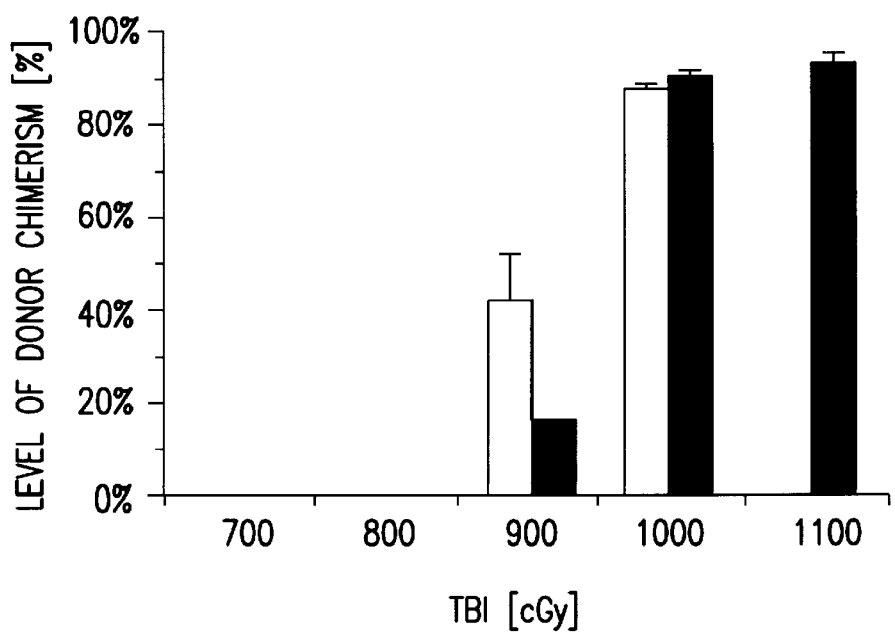
Figure 23A:
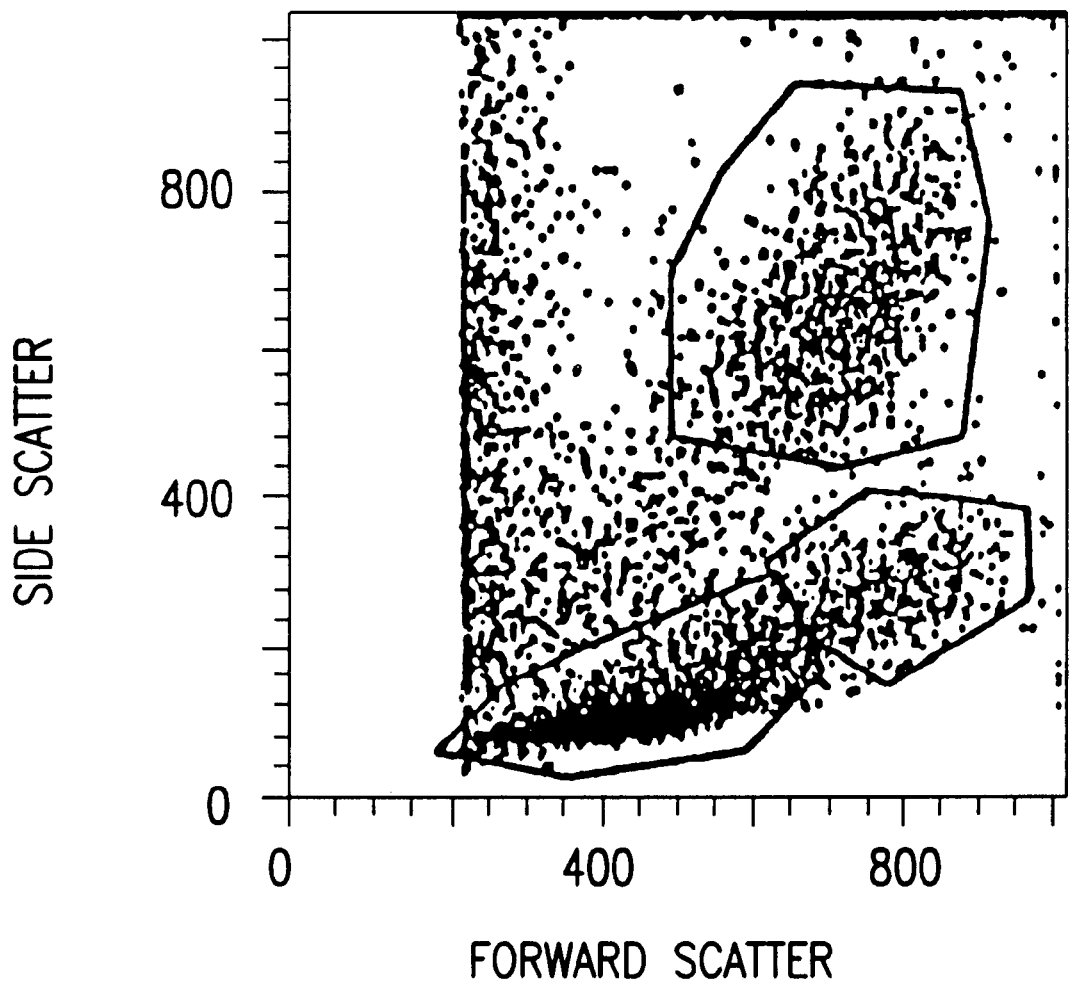
Figure 23B:
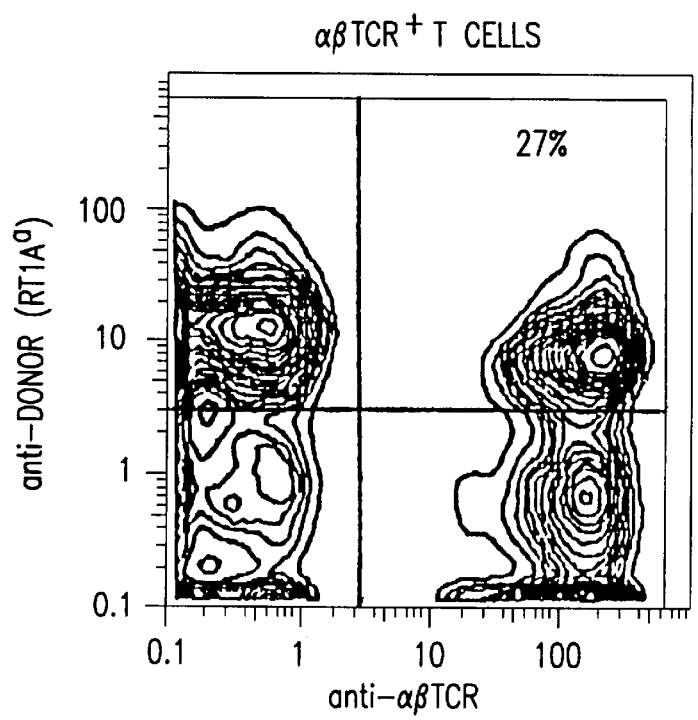
Figure 23C:
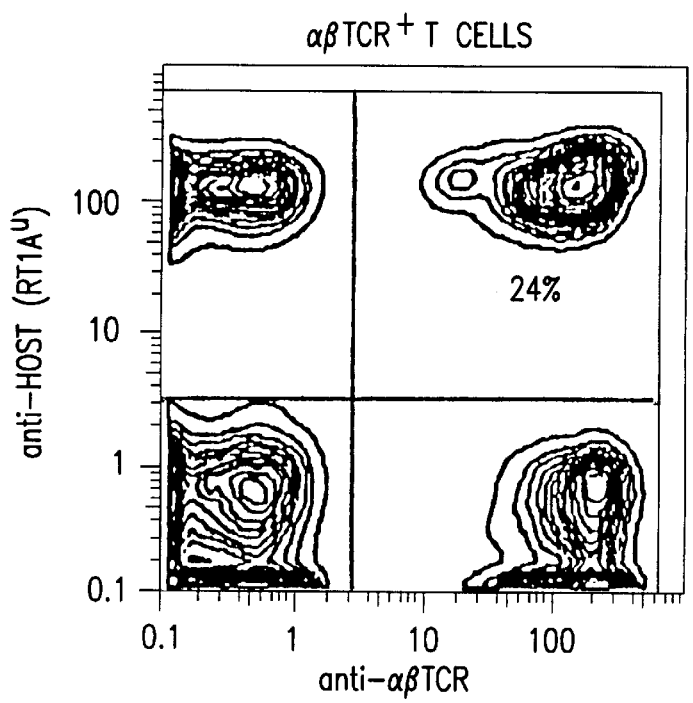
Figure 23D:
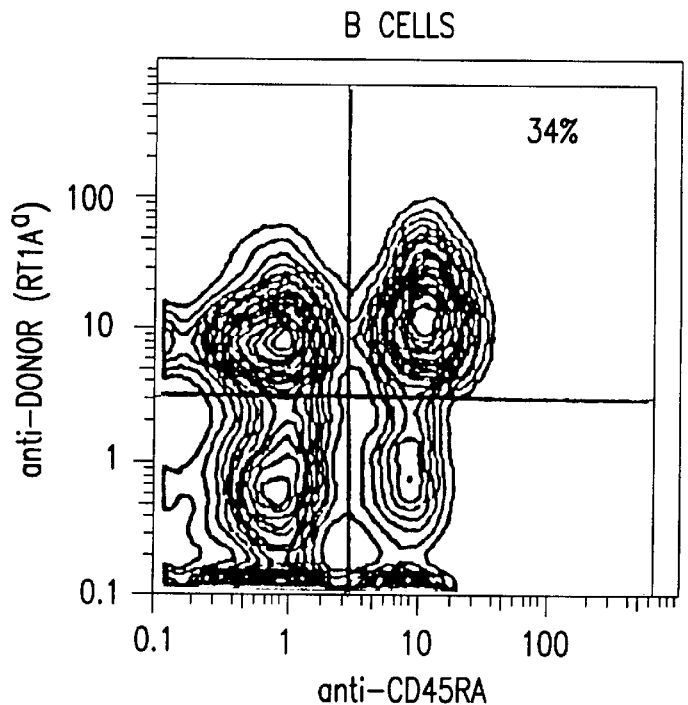
Figure 23E:
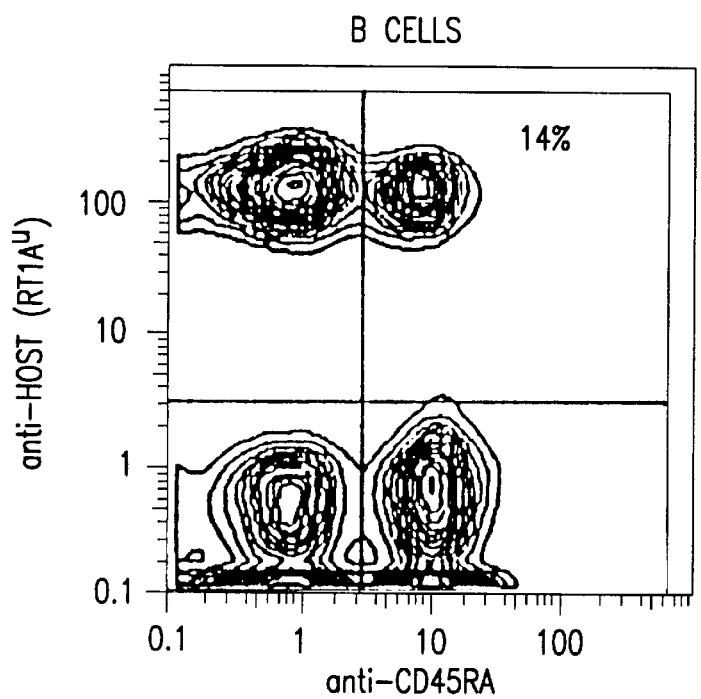
Figure 23F:
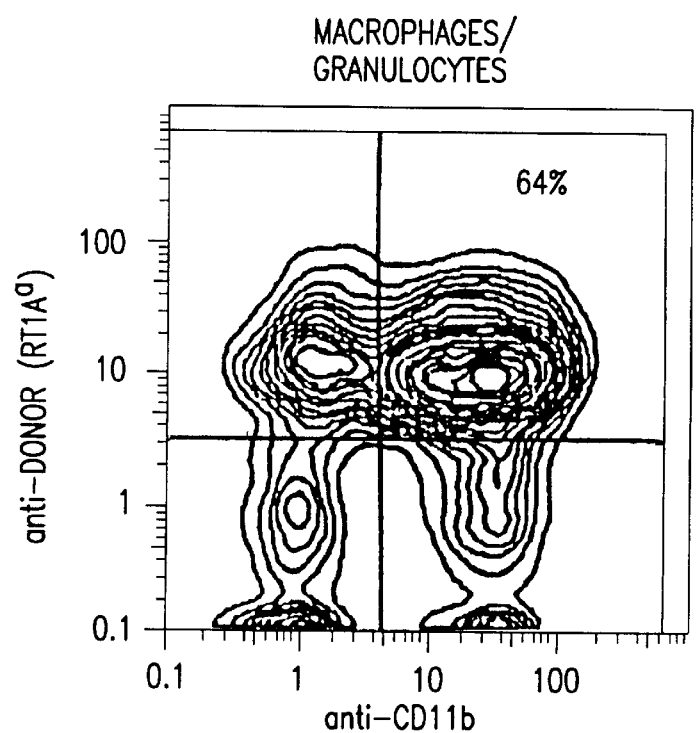
Figure 23G:
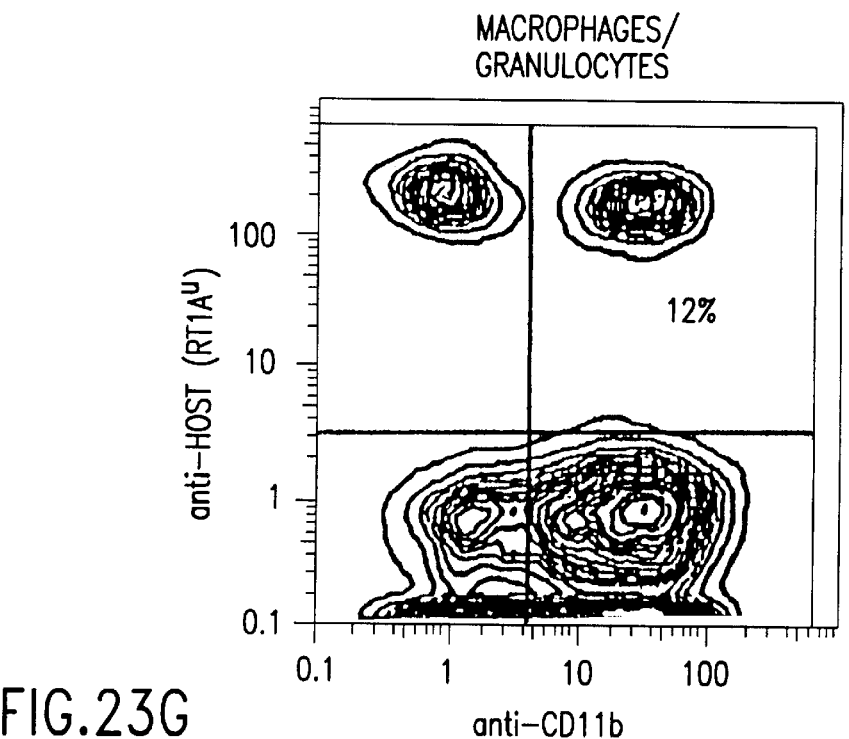

FIG. 22 Incidence (A) and level (B) of allogeneic donor chimerism as a function of recipient conditioning. WF rats were conditioned with TBI alone (dotted line and black bars) or with anti-NK mAb on days −3 and −2 and TBI on day 0 (solid line and open bars). Recipients were reconstituted with $100 \times 10^6$ TCD bone marrow cells from ACI rats. Engraftment was assessed 1 month after transplantation by flow cytometric analysis of PBL bearing recipient (RT1AU) or donor (RT 1A$^a$) MHC class I antigen. Data points represent results from 4 to 12 recipients prepared in at least 2 separate experiments. In B, only animals that engrafted were analyzed. Results are presented as the mean ±SEM (*=p<0.001).

FIG. 23 Detection of donor and host derived cells of lymphoid and myeloid lineages in mixed allogeneic chimeras using two-color-flow cytometry. Recipient WF rats received anti-NK mAb on days −3 and −2 followed by 900 cGy TBI and were transplanted with $100 \times 10^6$ TCD ACI bone marrow cells on day 0. Multilineage typing was performed 10 or 12 months following reconstitution (n=6). Naive WF and ACI rats served as controls (data not shown). Results of one representative chimera are presented. (A) Lymphocytes, monocytes and granulocytes were gated based on forward and side scatter. (B-D) In mixed allogeneic chimeras multiple cell lines of lymphoid as well as cells of myeloid lineage of host and donor origin were present.

Figure 24A:
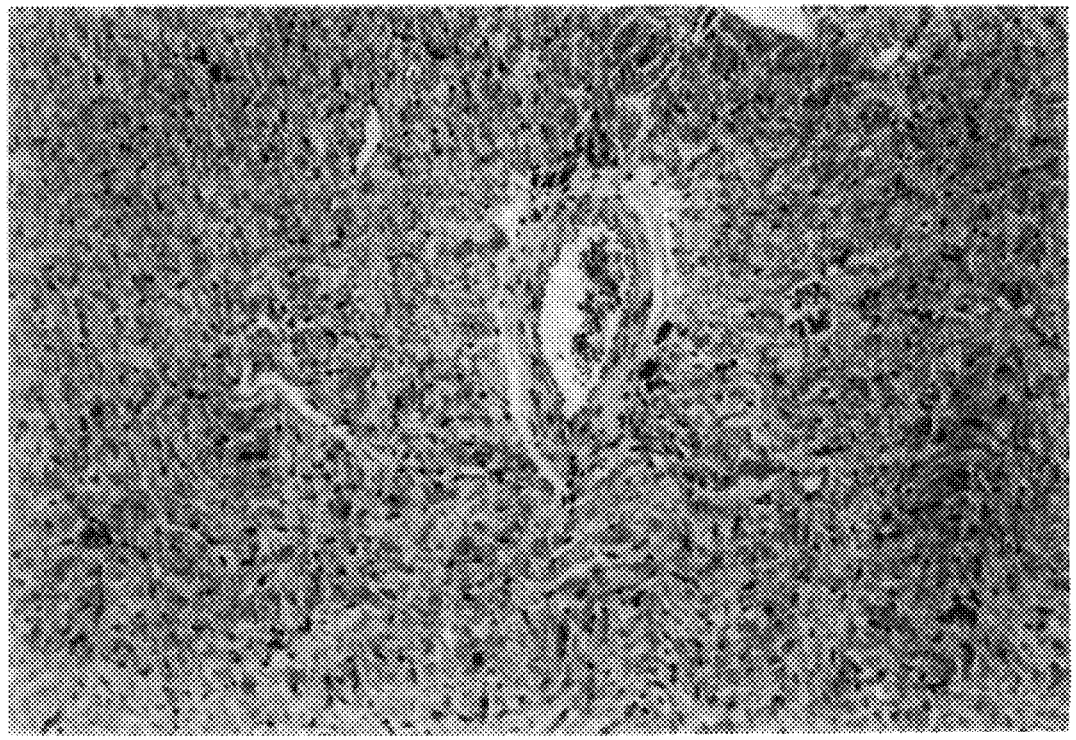
Figure 24B:
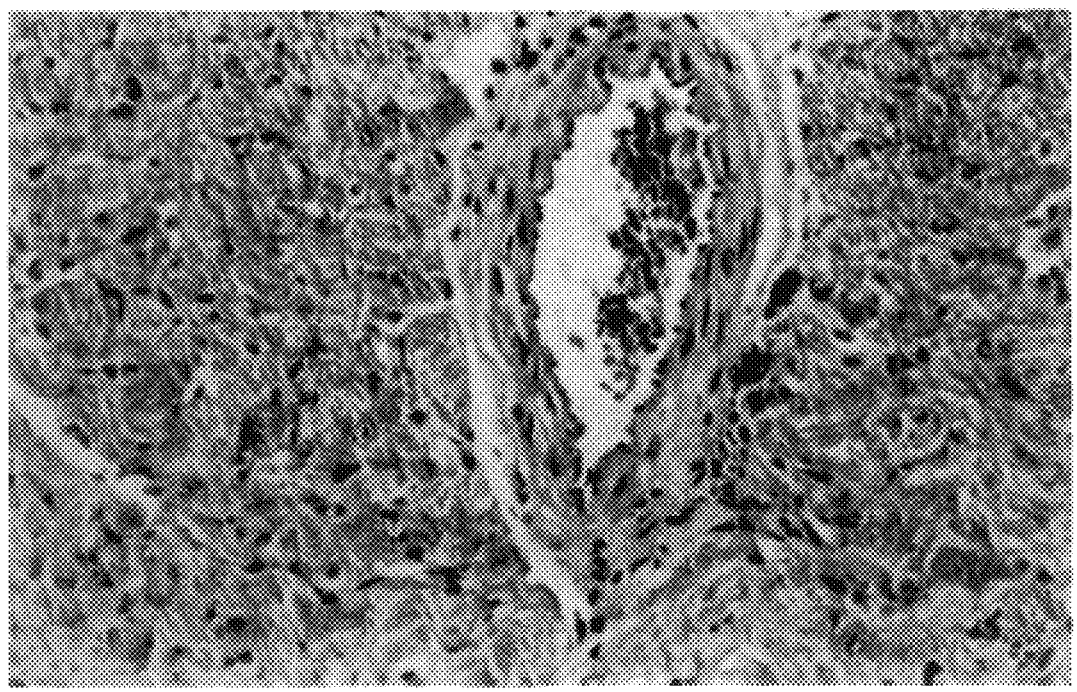

FIG. 24 Representative histological section of a donor-specific heart harvested from an ACI→WF chimera 170 days after transplantation. There was no evidence for acute or chronic allograft rejection. Cardiac allografts revealed a normal architecture that was free of lymphocytic infiltrate and no obliterative arteriopathy was seen (grade 0). (A) 100x. (B) 200x.

5. DETAILED DESCRIPTION OF THE INVENTION

The present invention relates to non-lethal methods of conditioning a recipient for bone marrow transplantation. These methods include the use of non-lethal doses of irradiation, cell type-specific or cell marker-specific antibodies and active fragments thereof, cytotoxic drugs or a combination thereof. In particular, the present invention encompasses an approach to make space in a recipient's bone marrow by targeting critical cell populations in the is hematopoietic microenvironment in the complete absence of radiation treatment.

The invention is discussed in more detail in the subsections below, solely for the purpose of description and not by way of limitation. For clarity of discussion, the specific procedures and methods described herein are exemplified using animal models; they are merely illustrative for the practice of the invention. Analogous procedures and techniques are equally applicable to all mammalian species, including human subjects.

5.1. Non-Lethal Conditioning Regimens for Donor Cell Engraftment

Mixed allogeneic chimerism has been demonstrated to be an effective means to induce donor-specific transplantation tolerance and preserve immunocompetence. Unlike fully allogeneic chimeras, which are relatively immunoincompetent, mixed allogeneic chimeras in which both host and donor-derived bone marrow cells co-exist, exhibit superior immunocompetence because of the presence of both host and donor-derived cells (Singer et al., 1981, *J Exp Med* 1-3:1286; Ildstad et al., 1985, *J Exp Med* 162:231). Mixed chimerism has been achieved using two different approaches, (1) high dose total lymphoid irradiation (TLI) followed by donor bone marrow transplantation (Slavin et al., 1978, *J Exp Med* 147(4):963) or (2) total body irradiation (TBI) followed by the transplantation of a mixture of T-cell depleted syngeneic and allogeneic bone marrow cells (Singer et al., 1981, *J Exp Med* 1-3:1286; Ildstad et al., 1985, *J Exp Med* 162:231). Both approaches result in stable long-term syngeneic and allogeneic chimerism and are associated with donor specific transplantation tolerance to skin and solid organ grafts (Ildstad and Sachs, 1984, *Nature* 307:168). The application of mixed allogeneic chimerism to induce tolerance clinically has been significantly hampered, however, by the excessive morbidity and cytoreduction which is believed to be a prerequisite for allogeneic engraftment across multimajor histocompatibility barriers.

Both host and donor factors are known to influence engraftment. Stable engraftment requires the host to "tolerate" the allogeneic stem cell and provide hematopoietic niches for the allogeneic stem cells to engraft, proliferate, and differentiate. These two conditions, believed to be essential for the engraftment of the stem cell, are referred to as (1) immunosuppression and (2) cytoreduction (Cobbold et al., 1992, *Immunol Rev* 129:165). Radiation-based regimens optimize both of these requirements by removing radiosensitive components within the recipient bone marrow to "make space" and by providing a generalized immunosuppression.

The efficacy and necessity of TBI in the facilitation of bone marrow engraftment have been demonstrated in a number of syngeneic and allogeneic models (Down et al., 1991, *Blood* 77(3):661, Storb et al., 1997, *Blood,* 89(8):3048–3054). In earlier studies by Down et al, even syngeneic engraftment failed to occur in a murine model without some pretreatment of the recipient with TBI (Down et al., 1991, *Blood* 77(3):661). Minimal space and suppression were required for syngeneic reconstitution since partial engraftment occurred with as little as 2Gy. However, significantly greater immunosuppression and/or "hematopoietic space" was required for MHC identical but minor antigen mismatched allogeneic marrow, resulting in failure of engraftment with less than 5.5Gy of TBI (Down et al., 1991, *Blood* 77(3):661). The dose-response curve of engraftment versus radiation dose in these previous MHC-compatible studies was sigmoidal, with a steep increase in the percentage of allogeneic engraftment seen at doses of 6 Gy or greater. The immunologic resistance to MHC-compatible allogeneic engraftment is nearly identical to the sigmoidal dose-response curve seen for MHC-disparate bone marrow engraftment in the present radiation-based conditioning model for both allogeneic and xenogeneic combinations (FIG. 1). The percentage of animals which engraft with a given radiation dosage undergoes an abrupt transition from no alloengraftment to nearly complete allochimerism within a very precise and reproducible range of 5.5Gy to 7Gy of TBI. The curve is shifted slightly to the right for xenoengraftment. These data therefore support the concept that there is a form of "space-making" provided by irradiation treatment, since at 5.5Gy only 10% of animals engrafted while at 6Gy>60% engrafted. A difference of 0.5Gy would be unlikely to represent a differential immunosuppressive effect, since NK cells and lymphocytes have a low threshold of radiosensitivity.

There is a well-characterized relative resistance to engraftment of the bone marrow stem cell across allogeneic disparities (Vallera and Blazer, 1989, *Transplantation* 47:70–1). Three times more allogeneic bone marrow cells are required to achieve reliable engraftment compared with autologous or syngeneic reconstitution (Ildstad and Sachs, 1984, *Nature* 307:168). Resistance to engraftment is further increased in donor-recipient strain combinations in which both MHC and minor antigen disparities exist and even further for xenoengraftment; i.e. Rat-mouse is eight times more, and human→mouse is ten times more (Ildstad et al., 1991, *J. Exp. Med.* 174:467). In the present invention, engraftment of MHC and minor antigen-disparate bone marrow occurred less often than did engraftment of MHC-disparate but minor antigen congenic bone marrow in recipients conditioned with a similar dose of TBI. These data indicate that the radioresistance of the barrier to alloengraftment increases with increasing antigenic disparity.

It has been established in Section 6, infra, that alloengraftment can be maximized yet recipient morbidity and mortality minimized by the addition of ALG or CyP to radiation-based conditioning. When 5Gy of TBI was administered in combination with either ALG or CyP, stable engraftment of allogeneic donor bone marrow cells was achieved. However, immunosuppression alone, without TBI, or TBI alone at a dose of 5Gy, were not sufficient for alloengraftment. Furthermore, CyP was equally effective in enhancing allogeneic engraftment when given before or shortly after bone marrow transplantation, in conjunction with low dose TBI. When ALG and CyP are used in combination with TBI, the dosage of TBI necessary to achieve stable donor cell engraftment is substantially reduced to 2Gy or lower. At 3 Gy, there is significant and stable engraftment in most recipients conditioned by the combination treatment.

It has also been established, in Section lo, infra, that durable engraftment of multilineage hematopoietic cells can be maximized through recipient conditioning with anti-CD8 antibodies, either singly or in combination with anti-CD4 antibodies, prior to low dose radiation-based conditioning. Optimization of anti-CD8 antibody pretreatment and transplantation cell dose may further reduce or eliminate entirely the need for low dose radiation-based conditioning.

While the results presented in Section 10, infra, initially indicated that $CD4^+$ or $CD8^+$ cells, rather than NK cells, are the populations that block allogeneic engraftment, subsequent work, discussed in Section 12, infra, establishes that NK cells do, indeed, play an important role in the rejection of allogeneic grafts. The results reported in Section 12 demonstrate that recipient conditioning with anti-NK mAb, which deplete radio-resistant NK cells, substantially reduces the dose of TBI required to achieve stable, long-term engraftment of MHC-mismatched BM cells. Chimeras prepared by this incomplete myeloablative approach show stable, multilineage donor chimerism and exhibit donor-specific transplantation tolerance to allografts.

TBI may be administered in a modified manner in the form of TLI. TLI is delivered in the same fashion as TBI, except that the entire body of the recipient is not exposed. The irradiation is directed at lymphoid tissues such as the spleen, vertebral column, sternum, ribs, etc. As a result, TLI is, in essence, a partial TBI that is less aggressive and cyto-ablative, and thus higher doses may be administered without lethal effects. TLI conditioning may be supplemented by CyP and/or ALG. These agents may be given before or after TLI. Preferably, they should be administered prior to TLI, and at one or more doses.

Historically, TLI has been utilized in fractionated doses to treat cancer patients. Typically, about 20Gy is administered in approximately 10 divided doses at 2Gy/dose. However, a single and relatively high ($\geq 7.5$ Gy) dose of TLI as a conditioning regimen has not been studied for conditioning recipients. Section 8, infra, shows that a single dose of TLI may lead to low levels of donor cell engraftment in a small percentage of recipients. However, the combined use of TLI with an alkylating agent such as CyP results in up to 30% of donor cell engraftment in baboons, demonstrating in vivo efficacy in non-human primates. Similarly, TLI may also be used with an antibody such as ALG or an antibody that is directed to stromal cells. The combined use of TLI, antibody and alkylating agent may further reduce the necessary dose of TLI.

The importance of the hematopoietic niches or "space" contributed by the low dose of TBI is even more evident when TBI is given one week prior to bone marrow transplantation, since engraftment did not occur in that setting. This failure to engraft is probably not due to loss of the immunosuppressive effect of the radiation, since suppression of T cell function following a single dose of radiation has been demonstrated to persist for months or even years (Haas et al., 1985, Trans Proc 17(l):1294). Rather, it is highly likely that the making of space is a prerequisite for engraftment and the delay between TBI and transplantation allowed the host marrow to undergo radiation repair, occupy the available spaces created by the radiation, and prevent alloengraftment despite adequate immunosuppression by ALG. Repair of sub-lethal damage, resulting in a similar dose-sparing effect, has been documented with fractionated TBI in syngeneic and MHC-compatible models (Down et al., 1991, Blood 77(3):661). This repair results in a greater resistance to alloengraftment with a shift in the radiation dose-response curve requiring an additional 3Gy of initial radiation to induce donor chimerism (Down et al., 1991, Blood 77(3):661).

It is of note that the same failure of alloengraftment did not occur if TBI is given one week prior to allogeneic bone marrow transplantation and followed by CyP treatment. Unlike ALG, which is believed to be immunosuppressive but not cytoreductive, CyP is toxic to rapidly proliferating cells. This toxicity may, therefore, have prevented the repair of sublethal damage to hematopoietic niches and syngeneic repopulation necessary to resist alloengraftment. In addition, CyP has been shown to result in endothelial injury with subsequent loss in the integrity of the sinus endothelial barrier (Shirota and Tavassoli, 1991, Exp. Hematol. 19:369). The augmentation of donor chimerism seen with CyP, as compared to ALG, therefore, may be secondary to increased access to hematopoietic niches rather than to any increase in the amount of unoccupied space.

The induction of tolerance towards MHC-disparate grafts using mAb therapy was recently reported (Cobbold et al., 1990, Eur J Immunol 20:2747). However, tolerance to other tissues of donor organ, i.e. splenocytes or bone marrow, was not reliably induced without the addition of 6Gy TBI. Moreover, engraftment was variable and often transient. This disparity in tolerance for different tissues has been termed "split tolerance". These recipients exhibit "tolerance" towards a local form of donor antigen, i.e. skin graft, but often exhibit proliferative and cytotoxic reactivity to other donor tissues such as lymphoid cells.

Although split tolerance has been a limitation in several nonlethal conditioning regimens, the preparation of allogeneic chimeras using low dose TBI-regimens in the present invention have resulted in systemic donor-specific tolerance towards both skin grafts and lymphoid tissues of donor-type. The prolonged survival of donor-type skin grafts in all animals which exhibit successful engraftment of allogeneic bone marrow is donor-specific, since chimeras are immunocompetent to reject third-party skin grafts with a time course similar to unmanipulated control mice. Similarly, animals which exhibit any degree of donor chimerism also exhibit specific functional tolerance in vitro towards donor antigens on lymphoid tissues as assessed by in vitro assays. No evidence of split tolerance has been found in any of the allogeneic chimeras tested, as animals which fail to exhibit tolerance towards donor lymphoid tissues also reject donor skin grafts and contain no detectable donor chimerism. In the present invention, chimerism is always associated with stable functional donor-specific transplantation tolerance in vivo and in vitro.

The mixed chimeras prepared with the nonlethal approaches characterized in the studies described herein exhibit similar multilineage donor chimerism which is stable for the duration of follow-up ($\geq 8$ months). Significant levels of donor chimerism are detected within each of the various lineages including lymphoid (T and B lymphocytes), NK cell, and myeloid (macrophages, granulocytes, erythrocytes, and platelets) in almost all animals examined (n=10). The level of donor chimerism among each of the lineages is variable within individual animals, an observation which parallels the findings in mixed chimeras prepared with lethal conditioning. These data suggest that tight regulatory control over both syngeneic and allogeneic pluripotent stem cells exists which determines the level of production of each individual lineage. Moreover, lineage production is also influenced by the conditioning used, since non-lethal mixed xenogeneic (Rat-mouse) chimeras produced rat-derived red blood cells, while chimeras prepared by lethal conditioning do not. There is also substantial data to suggest that the hematopoietic microenvironment in which the stem cells reside, may profoundly influence the development of the stem cells into various cell lineages.

The specificity of this regulation is clearly evident on examination of those chimeras which produce erythrocytes of only donor origin, despite an intact host hematopoietic system and production of syngeneic cells within the other hematolymphopoietic lineages. Such regulation may require specific cell-cell interactions found within "hematopoietic niches", thereby explaining the necessity of "space-making" agents, such as radiation, in allogeneic marrow transplantation. Recent studies by Jacobsen (Jacobsen et al., 1992, *J Exp Med* 176:927) have shown the specific cell-cell interactions within murine bone marrow between B cell precursors and a stromal cell. Each lineage may have a limited number of specific stromal cells necessary for developmental maturation or, alternatively, a single cell may be regulated to favor differentiation of a certain lineage at a given time. Prior to the present invention, methods to specifically target the cells which constitute the hematopoietic niches have not been attempted.

Nonlethal conditioning approaches which result in multilineage mixed chimerism may significantly expand the application of bone marrow transplantation for non-malignant diseases. Hematologic abnormalities including thalassemia and sickle cell disease, autoimmune states, and several types of enzyme deficiency states have previously been excluded from bone marrow transplantation strategies because the high morbidity and mortality associated with conditioning to achieve fully allogeneic bone marrow reconstitution could not be justified (Kodish et al., 1991, *N Engl J Med* 325(19):1349). Sickle cell disease is a prime candidate for mixed allogeneic reconstitution since only 40% of normal erythrocytes are required to prevent an acute crisis (Jandl et al., 1961, *Blood* 18(2):133; Cohen et al., 1992, *Blood* 76(7):1657).

In the present invention, multilineage mixed chimerism has been reliably achieved using minimal conditioning of the recipient. Other models of engraftment using sublethal recipient conditioning have failed to establish the presence of stable multilineage mixed allogeneic chimerism and permanent donor-specific tolerance which is crucial for conditions such as sickle cell disease or thalassemia. The nonlethal conditioning approaches described herein, may be useful in the treatment of non-fatal hematologic abnormalities, as well as for the induction of tolerance to simultaneous or subsequent cellular or solid organ allografts, in which the morbidity of conventional full cytoreduction is prohibitive.

Nonlethal conditioning methods which result in multilineage mixed chimerism may also significantly increase the ability to induce tolerance for transplantation across xenogeneic barriers, vastly expanding the availability of donor organs and tissues. The success of human organ transplantation as a clinical treatment is currently hampered by a persistent shortage of human donor organs and problems of chronic immunosuppression therapy post-transplantation. The present invention represents an advance in the ability to induce tolerance without toxic, myeloablative conditioning that opens the door to clinical applications of mixed chimerism and the induction of tolerance to allogeneic and xenogeneic tissue and solid organ transplantation. Methods of xenotransplantation are well known in the art, and described in, e.g., Fung J. et al, *World J. Surg.,* 1997, 21(9):956–961; Wolf P et al., *Vet. Res.,* 1997, 28(3) :217–222. In particular, the present invention contemplates the used of low dose TBI, cell type- or cell marker-specific antibodies, and/or alkylating agents to induce tolerance to xenogeneic transplants including, but not limited to, the transplantation of porcine and non-human primate tissues into humans.

5.2. Antibody for Use in Conditioning

The hematopoietic microenvironment is primarily composed of hematopoietic cells and stromal cells. The stromal cells occupy much of the space of the bone marrow environment and they include endothelial cells that line the sinusoids, fibroblastic cells such as adventitial reticular cells, perisinusoidal adventitial cells, periarterial adventitial cells, intersinusoidal reticular cells and adipocytes, and macrophages (Dorshkind, 1990, Annu. Rev. Immunol. 8:111; Greenberger, 1991, *Crit. Rev. Oncology/Hematology* 11:65). In addition, the Applicant has recently identified, characterized and purified a previously unknown cell type from the bone marrow that facilitates the engraftment of bone marrow stem cells across allogeneic and xenogeneic barriers. This cell referred to as hematopoietic facilitatory cell must be matched with the stem cell at the MHC for it to enhance stem cell engraftment. The facilitatory cells express a unique profile of cell surface markers: $Thy-1^+$, $CD3^+$, $CD8^+$, $CD45^+$ $CD45R^+$, MHC class $II^+$, $CD4^-$, $CD5^-$, $CD14^-$, $CD16^-$, $CD19^-$, $CD20^-$, $CD56^-$, $\gamma\delta$-$TCR^-$ and $\alpha\beta$-$TCR^-$. Although the Applicant's own work supports the CD3+phenotypic characterization of the hematopoietic facilitatory cell population, recent work of other groups raises the possibility that these cells may, in fact, be $CD3^-$. See, e.g., Aguila H et al., *Immunological Rev.,* 1997, 157:13–36. However, the hematopoietic facilitatory cells are readily identifiable by the other cell surface markers listed above. These cells are a newly recognized stromal cell population that is a critical component of the hematopoietic microenvironment. In allogeneic reconstitution experiments in mice, the murine facilitatory cells have been shown to be radiosensitive at about 3Gy.

The various stromal cell types express a number of well-characterized surface markers, including but is not limited to, vascular addressing, mannosyl and galactosyl residues, fasciculin III, villin, tetrapeptide, neural cell adhesion molecule receptor, hemonectin, B1 integrins, B2 integrins and B3 integrins (Greenberger, 1991, *Crit. Rev. Oncology/Hematology* 11:65). All the stromal cell populations including the facilitatory cells are potential targets of the conditioning regimen for recipients that is necessary for successful donor cell engraftment. Therefore, antibodies reactive with or specific for stromal cell surface markers may be used to deplete stromal elements in a cell type-specific non-lethal conditioning approach to make space available for bone marrow transplantation. For example, antibodies directed to Thy-1, MHC Class I and Class II molecules expressed on many stromal cell types may be used for this purpose. In addition, a monoclonal antibody designated STRO-1 has been shown to react with a cell surface antigen expressed by stromal elements in human bone marrow (Simmons and Torok-Storb, 1991, *Blood* 78:55). This antibody may be particularly useful for depleting stromal cells for making space in the bone marrow. In the mouse model, anti-Thy-1 and rabbit-anti-mouse-brain (RAMB) antibodies are effective in removing the facilitatory cell population from the bone marrow. RAMB is a polyclonal serum prepared by immunizing rabbits with homogenized mouse brain (Auchincloss and Sachs, 1983, *Transpl.* 36:436). Human brain also contains a number of epitopes cross-reactive with those expressed by the facilitatory cells. Thus, rabbit-anti-human-brain antibodies have been produced and may be used to remove the facilitatory cells from the hematopoietic microenvironment. However, since murine facilitatory cells have been shown to be radiosensitive at about 3Gy but substantial donor cell engraftment does not occur at radiation doses less than 6Gy as shown herein is in Section 6, infra, it is possible that the elimination of stromal cell types other than facilitatory cells is necessary to create the greatest amount of space for optimal donor cell engraftment.

It is also possible that other cell types contribute to the rejection of MHC-disparate grafts. For example, recipient NK cells are known to play an important role in the resistance to bone marrow engraftment. Bennett et al. first described the role of hybrid resistance in murine bone marrow graft rejection (Bennett, M., et al., 1987, *Adv Immunol.*, 41:333). The ability of F1 hosts to resist parental bone marrow cells has been shown to be mediated by NK cells. NK cell-induced bone marrow rejection occurs within 48 hours after transplantation without prior sensitization. The common hypothesis is that host NK cells kill targets that lack host-type MHC antigens (missing-self theory) (Bennett et al., 1987). Further, it was presented more recently that T-cell depleted bone marrow grafts are much more susceptible to NK cell-mediated rejection by the host (Murphy, W. J. et al., 1990, *J Immunol.*, 144:3305). Rolstad and others have intensively studied the role of NK cells in the rejection of allogeneic bone marrow cells in the rat (Rolstad, B., and H. B. Benestad, 1984, *Eur. J. Immunol.*, 14:793; Vaage, J. T., et al., 1991, *Eur. J. Immunol.* 21:2167). NK cells as the predominant effector cells in athymic rats mediated an immediate (within 24 hours) killing of allogeneic bone marrow cells in vivo and in vitro (Rolstad, 1984; Vaage, 1991). Collectively, these data suggest that NK cells play an important role in the rejection of allogeneic bone marrow grafts. As shown in Section 12, infra, specific targeting of NK cells in the recipient hematopoietic microenvironment results in a reduction of the minimum dose of TBI.

Also within the scope of the invention is the production of polyclonal and monoclonal antibodies which recognize novel antigens expressed by NK cells or by stromal cells, including the facilitatory cells of the hematopoietic microenvironment for use as specific agents to deplete these cells.

Various procedures known in the art may be used for the production of polyclonal antibodies to antigens of NK cells or stromal cells, including facilitatory cells. For the production of antibodies, various host animals can be immunized by injection with purified or partially purified NK cells or stromal cells, including but not limited to rabbits, hamsters, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

A monoclonal antibody to antigens of NK cells or stromal cells may be prepared by using any technique which provides for the production of antibody molecules by continuous cell lines in culture. These include but are not limited to the hybridoma technique originally described by Kohler and Milstein (1975, *Nature* 256: 495–497), and the more recent human B-cell hybridoma technique (Kosbor et al., 1983, *Immunology Today* 4:72; Cote et al., 1983, *Proc. Natl. Acad. Sci., USA* 80:2026–2030) and the EBV-hybridoma technique (Cole et al., 1985, *Monoclonal Antibodies and Cancer Therapy*, Alan R. Liss, Inc., pp. 77–96). Techniques developed for the production of "chimeric antibodies" by splicing the genes from a mouse antibody molecule of appropriate antigen specificity together with genes is from a human antibody molecule can be used (e.g., Morrison et al., 1984, *Proc. Natl. Acad. Sci. USA*, 81:6851–6855; Neuberger et al., 1984, *Nature,* 312:604–608; Takeda et al., 1985, *Nature* 314:452–454). Such chimeric antibodies are particularly useful for in vivo administration into human patients to reduce the development of host anti-mouse response. In addition, techniques described for the production of single chain antibodies (U.S. Pat. No. 4,946,778) can also be adapted.

Antibody fragments which contain the binding site of the molecule may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments (*Antibody: A Laboratory Manual,* 1988, Harlow and Lane, Cold Spring Harbor).

Also within the scope of the present invention are the production and use of polyclonal or monoclonal antibodies, or active fragments thereof, which recognize NK cell surface markers or the CD4 or CD8 cell surface markers, using methods such as those described in Sections 5.2 and 5.3.

5.3. Uses of Antibodies to Stromal Cells

The specific embodiments described in Section 6, infra, demonstrate that non-lethal conditioning of a recipient may be achieved by a reduced dose of TBI. Further, similar results can be obtained by an even lower dose of irradiation when applied in combination with ALG or an alkylating agent. Section 10, infra, demonstrates that similar results can be obtained by the use of anti-CD8 antibodies, either singly or in combination with anti-CD4 antibodies. Likewise, Section 12, infra, demonstrates that similar results can be obtained by the use of anti-NK antibodies. Thus, it is possible to develop a non-lethal conditioning method by totally eliminating the use of radiation or chemotherapeutic agents to and by using antibodies to deplete the critical targets of TBI. Likely targets of such an approach are the NK cells and the various stromal cell populations that form the hematopoietic microenvironment. Antibodies directed to cell surface markers of NK cells or stromal cells may be used to specifically deplete these cells without other adverse side effects in preparing a recipient for bone marrow transplantation in the absence of lethal doses of irradiation. Alternatively, such antibodies may be used in conjunction with low doses of irradiation and/or cytotoxic drugs.

According to this embodiment, the antibodies of the present invention can be modified by the attachment of an antiproliferative or toxic agent so that the resulting molecule can be used to kill cells which express the corresponding antigen (Vitetta and Uhr, 1985, *Annu. Rev. Immunol.* 3:197–212). The modified antibodies may be used in the preparation of a recipient prior to bone marrow transplantation in order to deplete stromal cells to make space for donor cells to engraft.

Accordingly, the antiproliferative agents which can be coupled to the antibodies of the present invention include but are not limited to agents listed in Table 1, infra, which is derived from Goodman and Gilman, 1990, *The Pharmacological Basis of Therapeutics*, Eighth Edition, Pergamon Press, New York, pp. 1205–1207, which is incorporated by reference herein.

Such antibody conjugates may be administered to a human patient prior to or simultaneously with donor cell engraftment. It is preferred that these conjugates are administered intravenously. Although the effective dosage for each antibody must be titrated individually, most antibodies may be used in the dose range of 0.1 mg/kg–20 mg/kg body weight. In cases where sub-lethal doses of irradiation are used, TLI of a human recipient may be administered at 5 to 10 Gy as a single dose or a combined total of 22Gy administered in fractionated doses. Preferably, TLI may be used between 7.5–9.5 Gy. Alternatively, TBI may be administered between 50 cGy and 700 cGy. When used in conjunction with anti-NK mAb, TBI is preferably administered between 850 cGy and 950 cGy, and most preferably administered at 900 cGy.

TABLE 1

ANTI-PROLIFERATIVE AGENTS WHICH CAN BE COUPLED TO ANTIBODIES

| Class | Type | Agent |
|---|---|---|
| Alkylating Agents | Nitrogen Mustards | Mechlorethamine |
| | | Cyclophosphamide |
| | | Ifosfamide |
| | | Melphalan |
| | | Chlorambucil |
| | Ethylenimine Derivatives | Hexamethyl-melamine |
| | | Thiotepa |
| | Alkyl Sulfonates | Busulfan |
| | Nitrosoureas | Carmustine |
| | | Lomustine |
| | | Semustine |
| | | Streptozocin |
| | Triazenes | Dacarbazine |
| Anti-metabolites | Folic Acid Analogs | Methotrexate |
| | Pyrimidine Analogs | Fluorouracil |
| | | Floxuridine |
| | | Cytarabine |
| | Purine Analogs | Mercaptopurine |
| | | Thioguanine |
| | | Pentostatin |
| Natural Products | Vinca Alkaloids | Vinblastine |
| | | Vincristine |
| | Epipodophyllotoxins | Etoposide |
| | | Teniposide |
| | Antibiotics | Dactinomycin |
| | | Daunorubicin |
| | | Doxorubicin |
| | | Bleomycin |
| | | Plicamycin |
| | | Mitomycin |
| | Enzymes | L-Asparaginase |
| Miscellaneous Agents | Platinum Coordinated Complexes | Cisplatin |
| | | Carboplatin |
| | Anthracenedione | Mitoxantrone |
| | Substituted Urea | Hydroxyurea |
| | Methyl Hydrazine Derivative | Procarbazine |
| | Adrenocortical Suppressant | Mitotane |
| | | Aminoglutethimide |
| Hormones and Antagonists | Adrenocorticosteroids | Prednisone |
| | Progestins | Hydroxyprogesterone caproate |
| | | Medroprogesterone acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |

TABLE 1-continued

ANTI-PROLIFERATIVE AGENTS WHICH CAN BE COUPLED TO ANTIBODIES

| Class | Type | Agent |
|---|---|---|
| Radioactive Isotopes | Phosphorous Iodine | Sodium phosphate $^{32}$P Sodium idoine $^{131}$I |
| Toxins | | Ricin A chain |
| | | Diphtheria toxin |
| | | Pseudomonas exotoxin A |

Any method known in the art can be used to couple the antibodies to an antiproliferative agent, including the generation of fusion proteins by recombinant DNA technology (Williams et al., 1987, *Protein Engineering* 1:493).

6. EXAMPLE

Allogeneic Bone Marrow Cells Engraft in Recipients Conditioned by Non-Lethal Methods

6.1. Materials and Methods

6.1.1. Animals

Male C57BL/10SnJ (B10), B10.BR, and BALB/c mice 6–8 weeks old were purchased from the Jackson Laboratory, Bar Harbor, Me. Animals were housed in a specific pathogen-free facility at the Biomedical Science Tower at the University of Pittsburgh.

6.1.2. Flow Cytometry

Recipients were characterized for donor cell engraftment using flow cytometry (FACS II, Becton Dickinson; Mountain View, Calif.) to determine the percentage of peripheral blood lymphocytes bearing H-$2^b$, H-$2^k$, and H-$2^d$ encoded antigens as described (Jeffries et al., 1985, *J Exp Med* 117:127). Briefly, peripheral blood was collected into heparinized plastic serum vials. 200 µl of Medium 199 (Gibco Laboratories; Grand Island, N.Y.) were added to each vial. After thorough mixing, the suspension was layered over 1.5 ml of room temperature Lymphocyte Separation Medium (LSM) (Organon Teknika; Durham, N.C.) and centrifuged at 37° C. (400 g×20 minutes). The buffy coat layer was aspirated from the Medium 199-LSM interface and washed with medium. Lymphocytes were stained for class I antigens with anti-H-$2^b$-FITC (Pharmingen; San Diego, Calif.), anti-H-$2^k$-FITC (Pharmingen), and anti-H-$2^d$-FITC (Pharmingen) monoclonal antibodies (Mab) for 45 minutes at 4° C. Lineage typing was performed by two color flow cytometry using anti-B-cell (B220-FITC, Pharmingen), anti-T cell (αβ-TCR-PE, CD4-FITC, CD8-PE, Pharmingen), anti-natural killer cell (NK1.1-PE, Pharmingen), anti-granulocyte (GR-1-FITC, Pharmingen), and nti-monocyte/macrophage (MAC-1-FITC, Boehringer Mannheim; Indianapolis, Ind.) Mab. These lineage-specific Mab were displayed versus anti-host (H-$2^b$, Pharmingen) and anti-donor (H-$2^d$ or H$2^k$, Pharmingen) Mab conjugated to FITC or were biotinylated and detected with a second streptavidin antibody conjugated to (phycoerythrin PE) (Pharmingen). Analyses were performed using forward and side scatter characteristics for the lymphoid and myeloid gates.

6.1.3. Platelet Isolation

Peripheral blood (0.9 ml) was collected into heparinized microcentrifuge vials. The blood was spun for four seconds at the maximal setting (14,000 rpm) of an Eppendorf microcentrifuge (Beckman #5415). This setting was chosen through an optimization strategy in which force and times were varied as a function of retrieved platelet number. This duration included the acceleration phase, which is incomplete when power is curtailed at the four second mark. After this, the samples were allowed to slow to a halt without braking. Platelet-rich plasma was then carefully aspirated with a disposable polyethylene pipette, avoiding any disturbance of the buffy coat. Triplicate platelet counts were obtained using a Coulter Model ZBl counter (Hialeah, Fla.), and the average (variation 5%) calculated. Platelets were then processed as described for the glucose phosphate isomerase-1 assay, infra.

6.1.4. Glucose Phosphate Isomerase-1 (GPI-1) Assay

Typing of red blood cell (RBC) and platelet phenotypes was performed using the GPI-1 assay (Ildstad, et al., 1991, *J Exp Med* 174:467). The precipitation pattern for BALB/c mouse and B10 mouse were performed as controls and determined to be totally disparate. Briefly, 8 $\mu$l of RBC were lysed in 400 $\mu$l of distilled water, and electrophoresis was performed on a Titan III cellular acetate strips with tris Hcl, 20 mM glycerin, 200 mM buffer (pH 8.7) (200 V for 1 hr.). Application was 2 cm from the anode.

After the run, the strips were covered with a 1% agarose gel containing Tris-Hcl 100 Mm (pH 8.0), NADP 300 $\mu$M, glucose-6-phosphate dehydrogenase 0.5 U/ml, fructose-6-phosphate 50 Mm, MMT 500 $\mu$M and phenozine methosulphate 200 $\mu$M. As precipitation occurred with the formation of formazan salt, the bands became visible (blue). The gel was removed, the reaction was arrested by immersing the strips in 5% acetic acid, and the bands were scanned with a Quick-Scan scanner.

Percentages were determined by comparison with the positive control. Values for each animal were normalized to 100%. In titrations performed to determine the sensitivity of this assay, as low as 2% of BALB/c RBC titrated into normal B10 RBC could be reliably detected (Ildstad, et al., 1991, *J Exp Med* 174:467). After isolation, platelets were typed in a similar fashion.

6.1.5. Skin Grafting

Skin grafting was performed by a modification of the method of Billingham and Medawar as previously described (Rappaport, 1977, *Trans Proc* 9:894; Kunst et al., 1989, *Immunogenetics* 30:187). Full thickness skin grafts were harvested from the tails of C57BL/10SnJ (H-2$^b$), B10.BR (H-2$^k$), BALB/C (H-2$^d$), and DBA (H-2$^d$) mice. Mice were anesthetized with 0.1% Nembutal (Abbott Laboratories; North Chicago, Ill.) intraperitoneally and full thickness graft beds were prepared surgically in the lateral thoracic wall. Care was taken to preserve the panniculus carnosum. The grafts were covered by a double layer of vaseline gauze and a plaster cast to prevent shearing. Three skin grafts from syngeneic, allogeneic donor, and third-party animals were placed on each animal with separation of each defect for graft placement by a 3 mm skin bridge. Casts were removed on the eighth day. Grafts were scored daily for percent rejection, and rejection was considered complete when no residual viable graft could be seen. Chronic rejection was the time point at which erythema and induration appeared in the grafts. Graft survivals were calculated by the life-table method (Gehan, 1969, *J Chronic Dis* 21:629) and the median survival time (MST) was derived from the time point at which 50% of grafts were surviving.

6.1.6. Mixed Lymphocyte Reactions (MLR)

Mixed lymphocyte reactions were performed as described (Schwartz et al., 1976, *J Immunol* 116:929; Hoffman et al., 1990, *J Immunol* 145:2220). Briefly, murine splenocytes were ACK-lysed (ammonium chloride potassium carbonate lysing buffer), washed, and reconstituted in DMEM (Gibco Laboratories) supplemented with 0.75% normal mouse serum, 0.55 mM L-arginine HCl+13.6 $\mu$M folic acid +0.3 mM L-asparagine+10 mM HEPES buffer, 1 mM sodium pyruvate, 2 mM glutamine, 100 U/ml penicillin, 100 $\mu$g/ml streptomycin, 0.05 mM 2-mercaptoethanol and lmM $N^G$ mono-methyl L-arginine (Hoffman et al., 1990, *J Immunol* 145:2220). $4\times10^5$ responders were stimulated with $4\times10^5$ irradiated stimulators (20Gy) in a total of 200 $\mu$l of media. Cultures were incubated at 37° C. in 5% $CO_2$ for 4 days, pulsed on the third day with 1 $\mu$Ci [$^3$H]thymidine (New England Nuclear; Boston, Mass.) and harvested on the fourth day with an automated harvester (MASH II; Microbiological Associated, Bethesda, Md.).

6.1.7. Cell-Mediated Lympholysis (CML)

CML assays were performed using a modification of techniques as described (Schwartz et al., 1976, *J Immunol* 116:929; Epstein et al., 1980, *J Immunol* 125:129; Lang et al., 1981, *Trans Proc* 13:1444). RPMI 1640 medium (Gibco Laboratories) was supplemented as above, except that 10% fetal calf serum (Gibco Laboratories) was used in place of normal mouse serum. $4\times10^6$ responders were co-cultured with $4\times10^6$ irradiated splenocyte stimulators (2oGy) in 2 ml of medium at 37° C. for 5 days. Mouse target blasts were stimulated with concanavalin A (Con A) (Miles Yeda Research Products, Rehovot, Israel) for 2–3 days. After 5 days responders were harvested, counted, and resuspended at appropriate effector-to-target ratios with $1\times10^4$ $^{51}$Cr-labeled, 2-3-d Con A mouse splenocyte blasts. After 4.5 hours, supernatants were harvested with the Titertek supernatant harvesting system and specific lysis was calculated as follows: specific lysis=(experimental release−spontaneous release)/(maximal Hcl release−machine background)×100. Spontaneous release was <25% of maximum release unless otherwise indicated.

6.2. Results 6.2.1. Allogeneic Engraftment with Nonlethal Total Body Irradiation Alone: Dose-Titration of Radiation-Based Conditioning In other studies of mixed chimerism, lethal irradiation was utilized as a conditioning approach and reconstitution consisted of a mixture of T cell depleted (TCD) syngeneic plus TCD allogeneic bone marrow cells (Ildstad and Sachs, 1984, *Nature* 307:168). In the present invention, a nonlethal radiation-based approach was used to achieve stable engraftment of allogeneic hematopoietic stem cells. In this model, the recipient was not fully cytoablated prior to allogeneic bone marrow transplantation, allowing the re-emergence of autologous stem cells ithin an environment of newly engrafted allogeneic bone marrow cells. Therefore, mixed allogeneic chimerism resulted even though only allogeneic bone marrow was infused as donor.

Titrations were performed to determine the minimum dose of TBI required to permit reliable engraftment of complete MHC-mismatched but minor antigen matched allogeneic bone marrow (B10.BR-B10). The dose of TBI administered directly correlated with the ability of allogeneic bone marrow cells to engraft (FIG. 1). Although allogeneic engraftment did not occur in all animals at doses of TBI below 6Gy, a significant increase in the number of animals which engrafted as allogeneic chimeras occurred at 6Gy. At this dose 50% of recipient animals that received 15×10⁶ allogeneic bone marrow cells exhibited donor chimerism (FIG. 1). Allogeneic engraftment was reliably achieved in 100% of all animals conditioned with 7Gy. It is of note that most of the animals which engrafted exhibited a high level of allogeneic donor chimerism≧95% (Table 2). Evidently, in this model, allogeneic stem cells either engraft and result in nearly total allogeneic chimerism or they completely fail to engraft. The abrupt transition between failure of allogeneic engraftment to nearly complete allochimerism occurred near 6Gy, indicating that the "barrier(s)" to allogeneic chimerism is very specific, but once overcome, allogeneic engraftment occurs unimpeded.

TABLE 2

LEVEL OF DONOR CHIMERISM IN ANIMALS WITH ALLOGENEIC ENGRAFTMENT[a]

| Reconstitution | TBI Dose | Chimera # | % Donor Chimerism |
|---|---|---|---|
| 15 × 10⁶ B10.BR→B10 | 5.5 Gy | 1 | 99 |
|  | 6 Gy | 1 | 99 |
|  |  | 2 | 99 |
|  |  | 3 | 68 |
|  |  | 4 | 98 |
|  |  | 5 | 98 |
|  |  | 6 | 97 |
|  | 7 Gy | 1 | 97 |
|  |  | 2 | 99 |
|  |  | 3 | 99 |
|  |  | 4 | 100 |

[a]PBL typing was performed by flow cytometry 2 months post-reconstitution (B10.BR→B10) using anti-H2$^k$-FITC (B10.BR) and anti-H-2$^b$-FITC (B10) mAb. Animals are taken from those represented in FIG. 1. The percent donor chimerism (% B10.BR) is shown only for those animals which engrafted at each of the representative TBI doses. Results are pooled from 2 representative experiments out of a total of 5, and are normalized to 100%.

Similar studies were performed to examine whether engraftment of bone marrow from a donor strain (BALB/c; H-2$^d$) which was mismatched for MHC plus multiminor histocompatibility antigens could reliably occur at similar non-lethal doses of TBI. Resistance to alloengraftment was greater for BALB/c bone marrow than for MHC-disparate B10.BR bone marrow. Although comparable levels of engraftment with BALB/c and B10.BR allogeneic marrow occurred after lethal (9.5Gy) conditioning, less than 20% of recipients pretreated with 6Gy TBI prior to transplantation with BALB/c bone marrow cells [BALB/c→B10] exhibited any degree of allogeneic chimerism.

6.2.2. Engraftment of Allogeneic Bone Marrow is Enhanced by Anti-Lymphocyte Globulin Anti-lymphocyte globulin (ALG) is a polyclonal serum directed to multiple antigens expressed on lymphocytes which has often been used as an immunosuppressive agent (Monaco, 1991, Trans Proc 23(4):2061). It produces a transient ablation of lymphocytes from blood and tissue. Early studies documented the induction of donor-specific tolerance in thymectomized mice given ALG plus donor bone marrow cells, leading to extensive study of its uses in transplantation (Wood et al., 1971, Trans Proc 3(l):676). Donor cell engraftment in these studies was transient, if present at all. Although further attempts at generating permanent tolerance against fully allogeneic donor antigens with ALG alone have been less successful, survival of allografts has been prolonged in several species using ALG in combination with donor bone marrow cells or other immunosuppressive agents (Wood et al., 1971, Trans Proc 3(l):676; Monaco, 1991, Trans Proc 23(4):2061). Therefore, it is possible that this serum preparation was able to deplete cells, although inefficiently, in the hematopoietic microenvironment to create space in a recipient.

To examine whether ALG would enhance the engraftment of allogeneic bone marrow in the established radiation-based model, recipient B10 mice received one of three conditioning approaches prior to transplantation with 40×10⁶ or 15×10⁶ BALB/c bone marrow cells: 70 mg/kg i.v. ALG given three days prior to bone marrow transplantation (Group 1); 5Gy of TBI on the day of transplantation (Group 2); or both ALG and TBI as administered in groups 1 and 2 (Group 3). The timing of ALG was chosen to assure maximum immunosuppression at the time of allogeneic bone marrow infusion (Wood et al., 1971, Trans Proc 3(l):676). As in previous analysis, recipients were peripheral blood leukocyte (PBL)-typed for evidence of allogeneic engraftment 2 months following bone marrow transplantation. Allogeneic chimerism occurred in 85% of recipients conditioned with ALG and TBI (Group 3), while no evidence of alloengraftment was seen in animals receiving either ALG or TBI alone (Groups 1 and 2) (FIG. 2).

6.2.3. Influence of Cell Dose in the Allogeneic Inoculum on Engraftment with ALG and TBI Conditioning It has been demonstrated that a greater number of allogeneic donor cells are required to achieve reliable engraftment when compared with syngeneic reconstitution (Ildstad and Sachs, 1984, Nature 307:168; Ildstad et al., 1986, J Exp Med 163:1343). This has been termed alloresistance to engraftment. To examine the influence of donor cell number on the ability of ALG and TBI to enhance alloengraftment, dose-titration studies were performed in which the above established radiation plus ALG conditioning were utilized. Recipients were conditioned as above prior to receiving 40×10⁶, 15×10⁶, or 5×10⁶ BALB/c bone marrow cells. The percentage of allogeneic donor-derived cells detected in the peripheral blood of the recipient (i.e. donor chimerism) increased in relation to the initial number of donor cells transplanted (Table 3). All animals appeared healthy and had no stigmata of GVHD although they had received untreated bone marrow cells.

TABLE 3

INFLUENCE OF CELL DOSE OF ALLOGENEIC BONE MARROW INOCULUM ON THE LEVEL OF DONOR CHIMERISM[a]

| GROUP | RECONSTITUTION | ANIMAL | % BALB/c PBL |
|---|---|---|---|
| 1 | 40 × 10⁶ BALB/c→B10 | 1 | 87 |
|  |  | 2 | 86 |
|  |  | 3 | 87 |
| 2 | 15 × 10⁶ BALB/c→B10 | 1 | 30 |
|  |  | 2 | 71 |
|  |  | 3 | 75 |
|  |  | 4 | 0 |
| 3 | 5 × 10⁶ BALB/c→B10 | 1 | 1 |
|  |  | 2 | 0 |

[a]PBL typing was performed by flow cytometry 2 months post-reconstitution using anti-H-2$^d$-FITC and anti-H-2$^b$-FITC mAb. Results are from one of three representative experiments and are normalized to 100%.

6.2.4. Influence of Cell Dose and Minimal Conditioning on Level of Engraftment in Syngeneic Bone Marrow Transplantation The morbidity and mortality associated with fully ablative conditioning have limited the use of bone marrow transplantation (BMT) in non-malignant diseases. Autoimmune diseases, sickle cell anemia and enzyme deficiencies could be treated with BMT, if conditioning protocols with only partial ablation and minimal toxicity could be developed. conditioning of the recipient has two components: immunosuppression to abolish alloreactivity and prevent rejection of the donor bone marrow (BM) by host cells and cytoreduction to provide "space" or vacant niches. In order to dissociate "space" from alloreactivity, we examined the role of cell dose and minimal conditioning in a syngeneic model for BMT. It has been established that syngeneic recipients of physiological numbers of BM require low dose irradiation for engraftment to occur. To overcome the requirement for space, its' underlying mechanisms have to be understood. In this study we focussed on the influence of cell dose and irradiation in engraftment characteristics of syngeneic recipients. Five, 10, or $15 \times 10^6$ untreated BM cells from B6.SJL-Ptprc$^a$Pep3b/Boy (Ly5$^a$) donors (Ptprc$^a$) were transplanted to syngeneic C57BL/6J recipients (B6), conditioned with 0, 50, 100 or 150 cGy total body irradiation (TBI) (n=4 per group). The mice differ in the expression of the Ly5 antigen, a non-immunogenic difference that can be detected by flow cytometry. While the Ptprc$^a$ donor mice express Ly5.1, B6 mice express Ly5.2. The level of chimerism was determined 28 days after BMT. As expected, no engraftment occurred without irradiation. With 50 cGy irradiation 2 of 4 animals transplanted with 5 or $10 \times 10^6$ cells, respectively, engrafted at levels just at the threshold of sensitivity of flow cytometric analyses (0.4%, see FIG. 14). 100% of the animals conditioned with 50 cGy engrafted, when transplanted with $15 \times 10^6$ cells. At irradiation doses >50 cGy 100% of the animals engrafted, regardless of the cell dose, but the level of engraftment appeared to correlate with the donor cell dose. In contrast to allogeneic engraftment, where a steep sigmoid transition between no engraftment and engraftment is observed, our results in a syngeneic model showed a slow, stepwise enhancement of engraftment when cell dose and/or irradiation are increased. These findings suggest that space is not mediated by a defined cell population, which when removed allows engraftment. It rather points to a competitive re-population in which the syngeneic donor cells compete with host stem cells.

6.2.5. Allogeneic Engraftment is Enhanced by the Addition of Cyclophosphamide to the Established Radiation-Based Conditioning CyP is an alkylating agent used widely in treatment of lymphohematopoietic malignancies, such as leukemia (Gershwin et al., 1974, *Annals Int Med* 80:531; Copelan and Deeg, 1992, *Blood* 80(7):1648). It has been demonstrated to increase leukemic cell killing and reduce tumor relapse (Copelan and Deeg, 1992, *Blood* 80(7):1648). CyP also exhibits immunosuppressive effects, by killing rapidly proliferating cells and resting lymphoid cells, with an impairment of both humoral and cellular responses (Mayumi et al., 1987, *Transplantation* 44(2):286). Although conditioning with CyP alone does not result in allogeneic engraftment, combination therapies have proven useful in permitting engraftment of bone marrow From HLA-identical siblings (Graw et al., 1972, *Transplantation* 14:79).

In order to assess the ability of CyP to enhance alloengraftment in the established radiation-based model, B10 mice were treated with one of three conditioning approaches prior to transplantation with $40 \times 10^6$ B10.BR or BALB/c bone marrow cells. Mice received 200 mg/kg i.p. of CyP alone (Group 1); 5Gy of TBI on the day of transplantation (Group 2); or 5 Gy TBI followed by CyP 2 days later (Group 3). Animals were PBL typed 2 months following reconstitution. Engraftment of allogeneic bone marrow occurred in nearly all recipients receiving 5Gy TBI plus CyP (FIG. 3). The degree of donor chimerism achieved was >90% in all chimeras conditioned with this approach. In contrast, all animals treated with TBI or CyP alone failed to engraft (Groups 1 and 2).

6.2.6. Influence of Timing OF TBI on Alloengraftment in Recipients Conditioned with Anti-Lymphocyte Globulin or Cyclophosphamide To examine the influence of timing of radiation on the engraftment of allogeneic bone marrow, recipient B10 mice were irradiated with 5Gy TBI one week prior to transplantation with $40 \times 10^6$ BALB/c allogeneic bone marrow cells. Additional animals, prepared in an identical fashion, received 70 mg/kg i.v. of ALG three days prior to transplantation or received 50 mg/kg i.p. CyP six, five, four, and three days prior to transplantation.

Animals conditioned with 5Gy of radiation alone failed to engraft even if the radiation was administered one week prior to transplantation (FIG. 4). Although 75% of the recipients exhibited allogeneic chimerism when treated with ALG plus TBI administered on the day of bone marrow transplantation, this enhancement of alloengraftment did not occur when TBI was given one week prior to transplantation. In contrast, the timing of TBI had little effect on the enhancement of alloengraftment seen with CyP. Nearly 75% of all recipient mice treated with TBI and CyP engrafted regardless of donor-strain or whether the CyP was administered before or shortly after the TBI (n=15) (FIG. 4). All of these chimeras exhibited ≧90% allogeneic donor chimerism.

All of the above approaches indicate that the hematopoietic microenvironment plays a major role in bone marrow engraftment.

6.2.7. Characterization of a Nonlethal Radiation-Based Approach for Cytoreduction To assure that the conditioning described herein was "nonlethal" with respect to overall morbidity and hematopoietic viability, control mice were conditioned but did not receive an allogeneic bone marrow transplant. Survival of the animals was excellent (FIG. 5), and none of the regimens used in this study resulted in any observable morbidity, i.e. diarrhea, cachexia, lassitude, hunched gate, dermatitis, alopecia, or anorexia. Moreover, these conditioning regimens were not lethal to the host hematopoietic stem cell since autologous repopulation resulted.

6.2.8. Nonlethal Mixed Chimeras: Evidence for Multilineage Mixed Chimerism

Mixed allogeneic chimeras conditioned with lethal TBI (9.5Gy) exhibit stable mixed chimerism of lymphoid and myeloid lineages, including T cells, B cells, NK cells, erythrocytes, platelets, and macrophages. To determine whether mixed allogeneic chimeras prepared with nonlethal conditioning exhibited selective syngeneic, allogeneic or mixed chimerism of individual hematolymphopoietic lineages, studies were undertaken to determine the proportion of cells within each lineage which were host (B10) or donor (BALB/c)-derived.

Figure 6A:
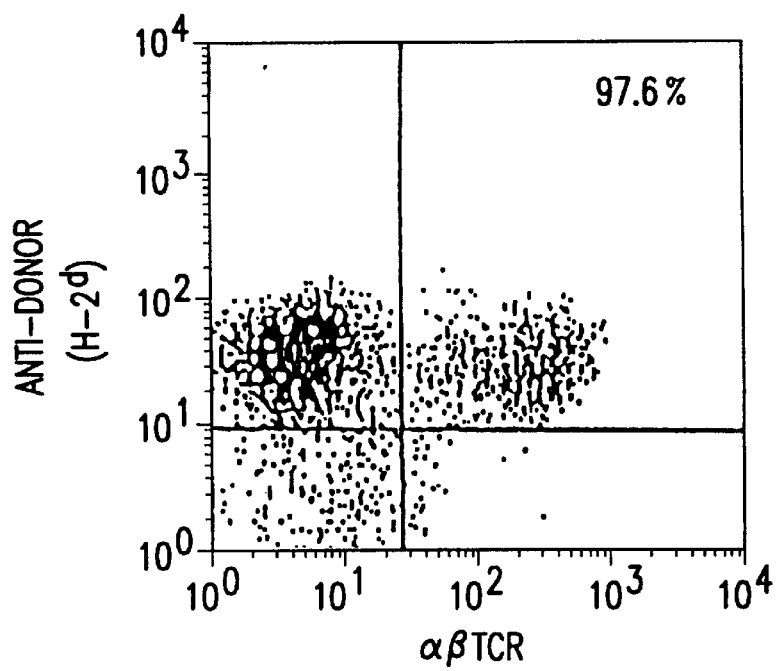
Figure 6B:
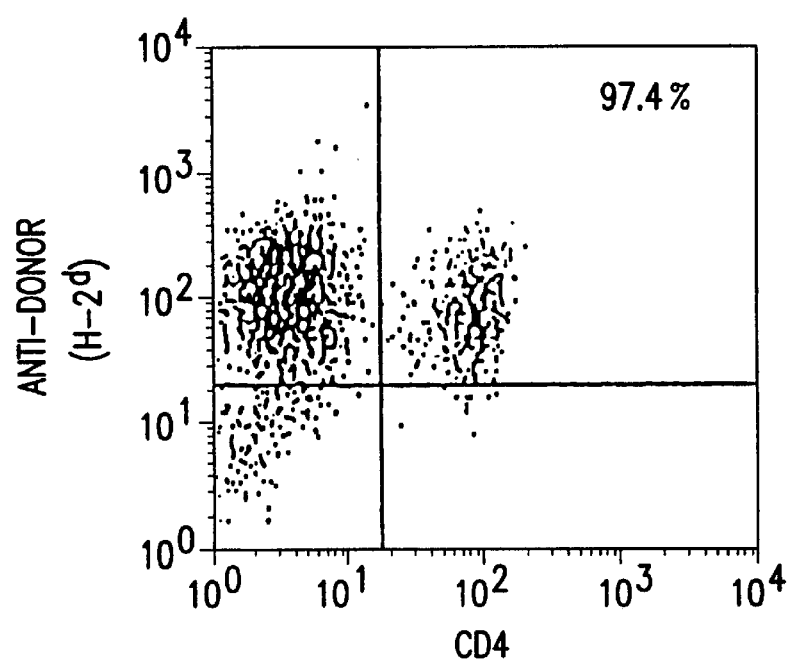
Figure 6C:
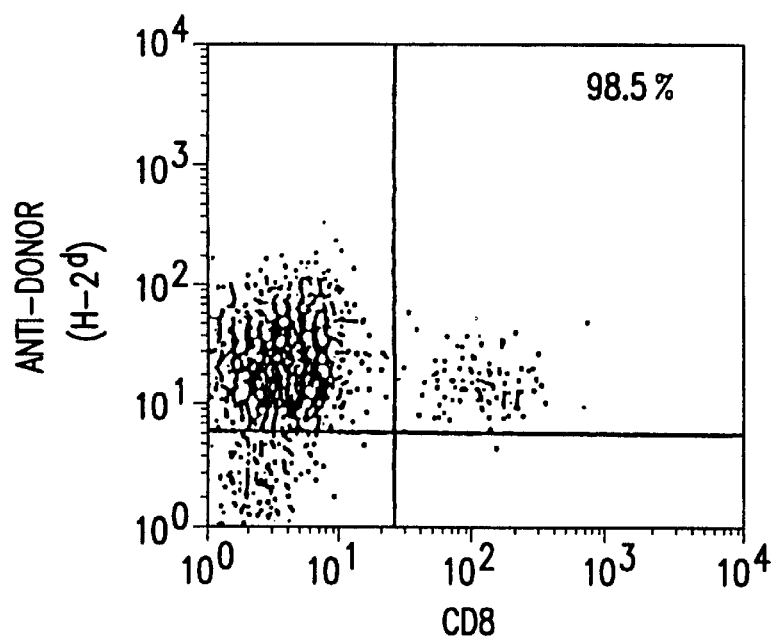
Figure 6D:
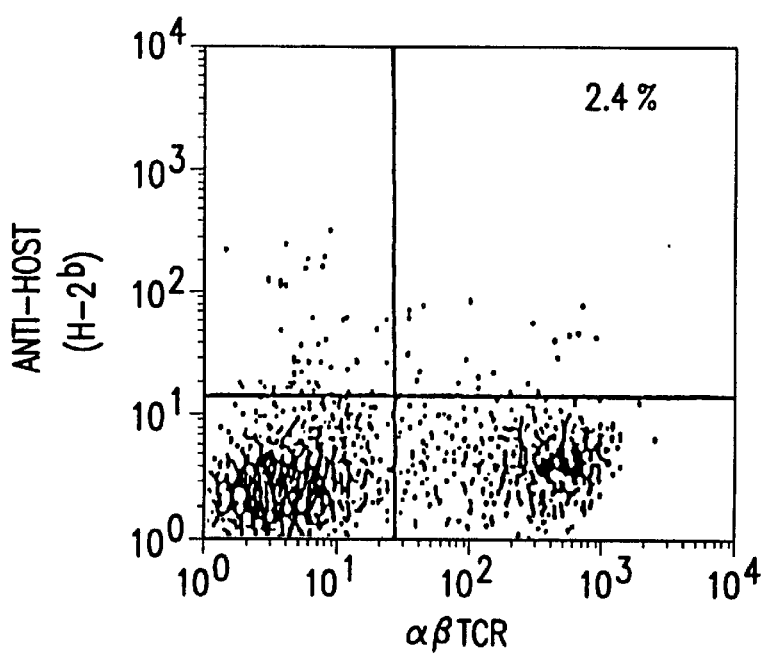
Figure 6E:
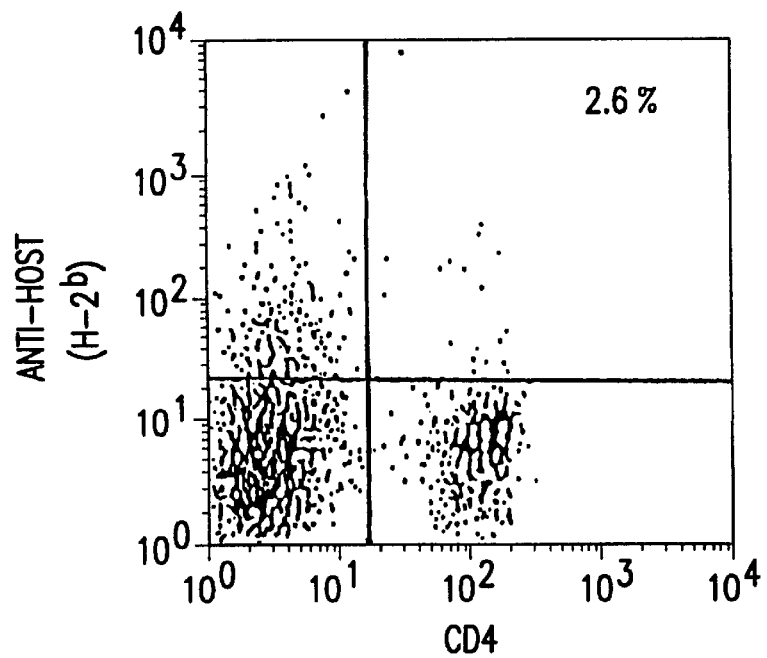
Figure 6F:
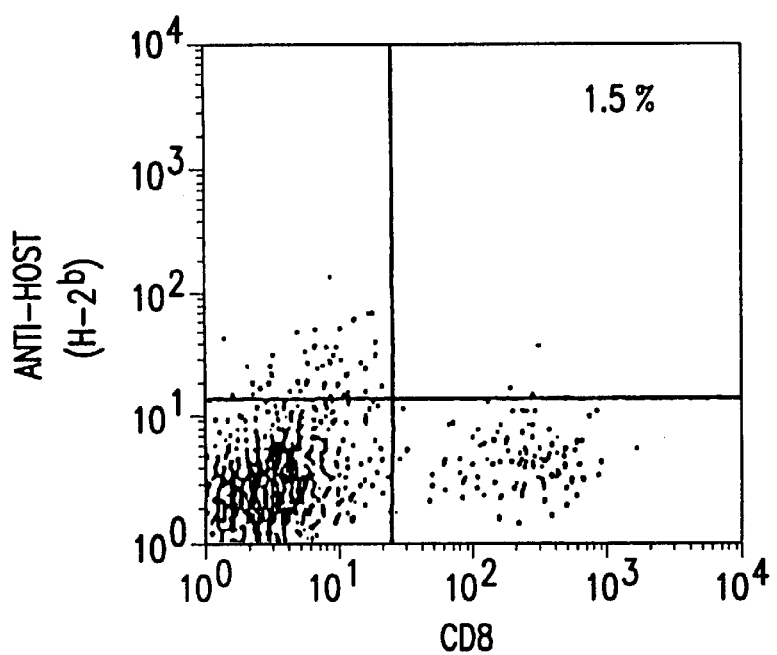
Figure 6G:
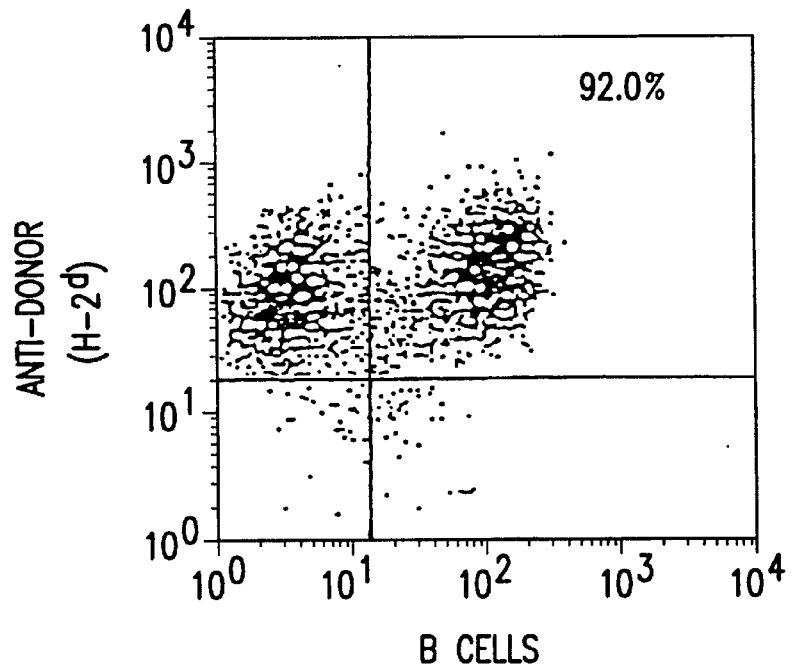
Figure 6H:
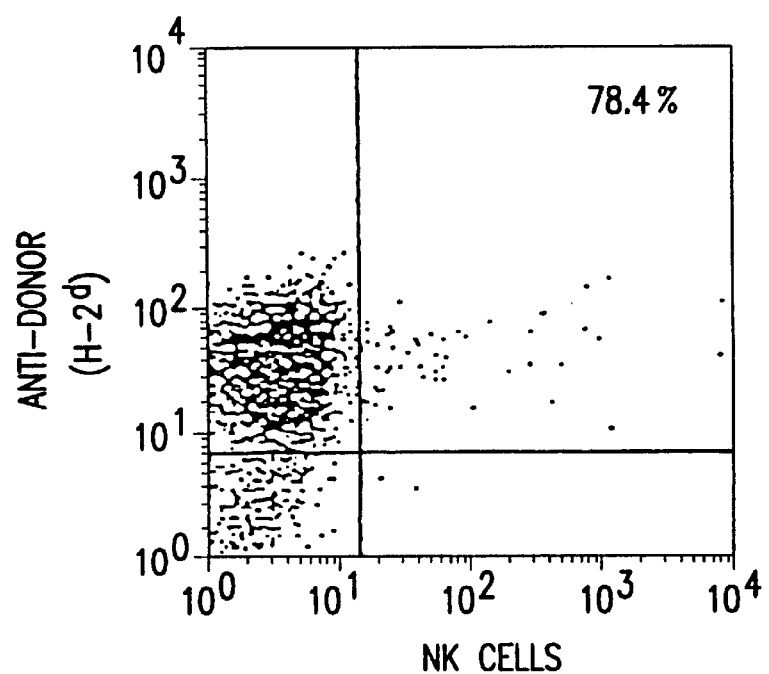
Figure 6I:
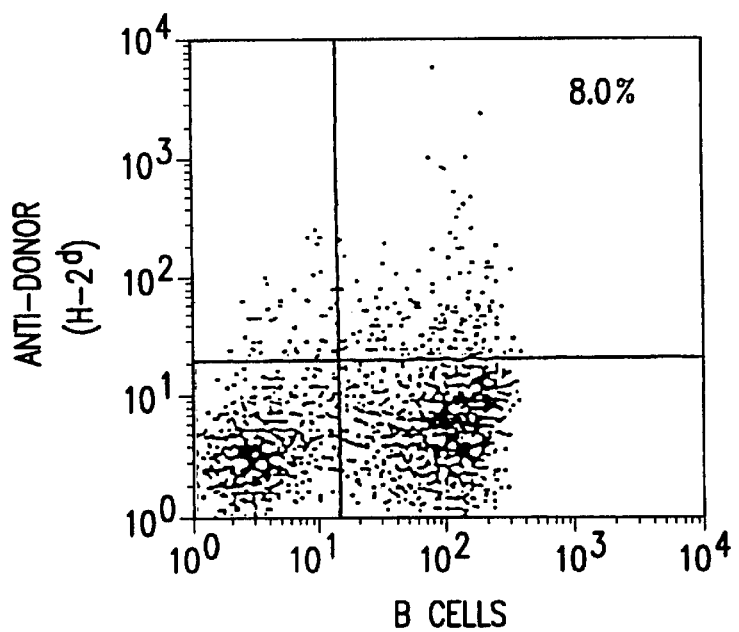
Figure 6J:
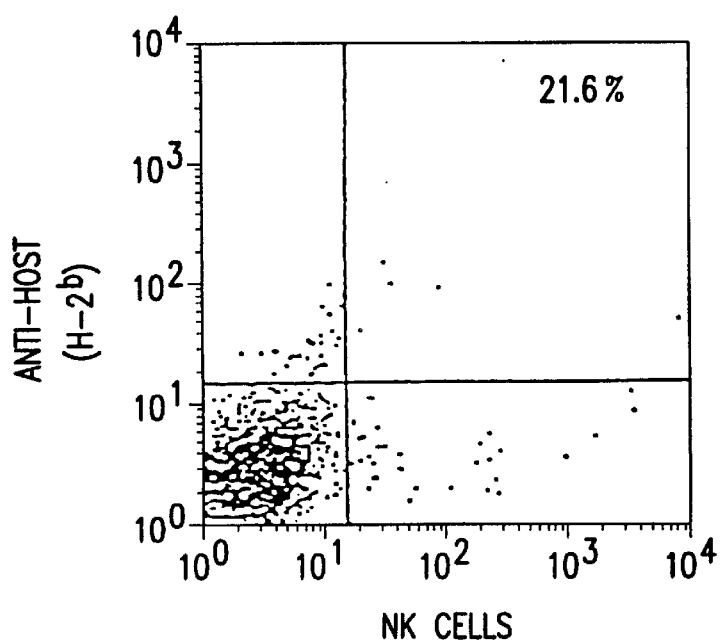
Figure 6K:
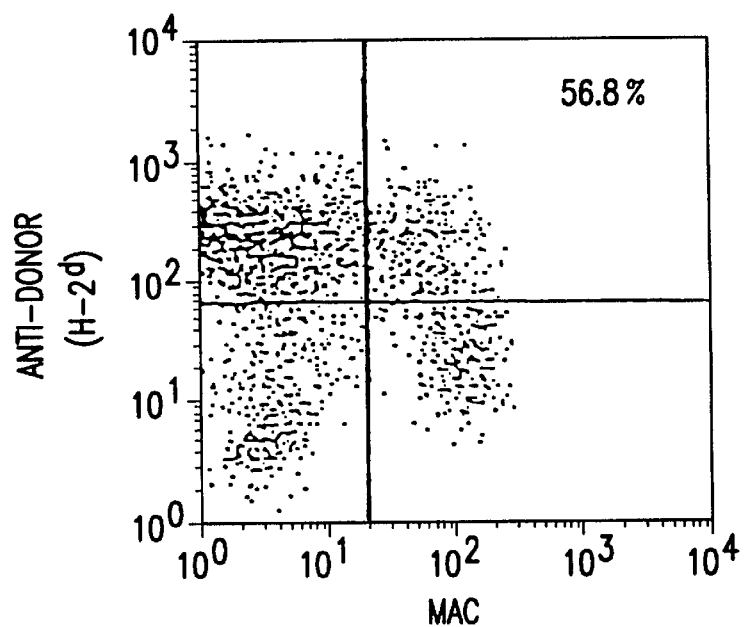
Figure 6L:
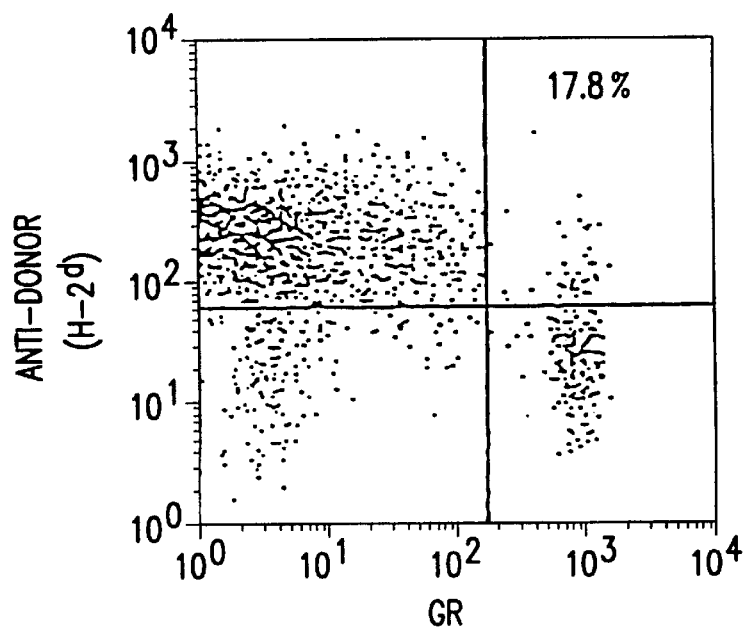
Figure 6M:
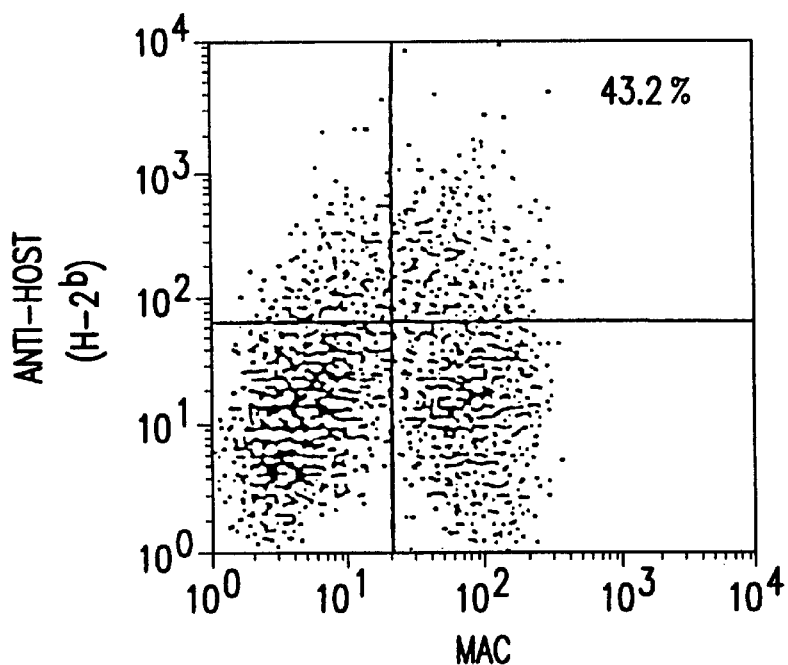
Figure 6N:
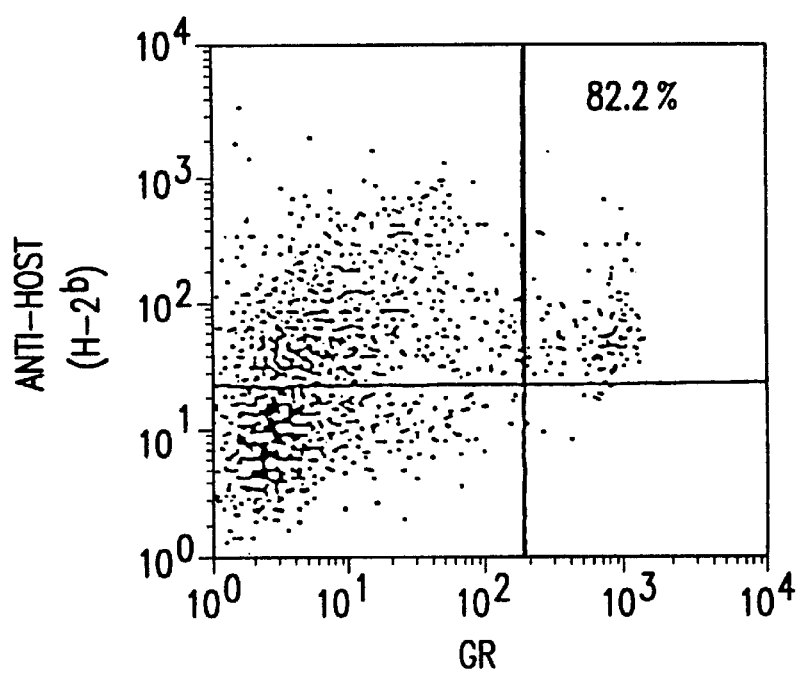

Animals which exhibited evidence for engraftment by PBL typing also had allogeneic cells of donor origin detected for each of the individual hematolymphopoietic lineages produced by the stem cell (FIGS. 6A, 6B and 6C). The contribution of donor-derived cells varied among each of the lineages in the ten animals tested, with T lymphocytes ranging from 3.6 to 100%; B lymphocytes from 3.8 to 99%; NK cells from 9.8 to 96%; and macrophages from 21 to 76%. It was also influenced by the conditioning approach utilized.

6.2.9. Evidence that Erythrocytes and Platelets in Allogeneic Chimeras are of Both Syngeneic and Allogeneic Origin In order to analyze the proportion of donor and host erythrocytes (RBC) and platelets, allogeneic chimeras were prepared using BALB/c ($H-2^d$) and B10 ($H-2^b$) donor/recipient strain combinations which differ at the Glucose Phosphate Isomerase-1 (GPI-1) isoenzyme. All except one of the chimeras with known allogeneic PBL chimerism also exhibited RBC and platelets of allogeneic origin (Table 4). The proportion of allogeneic chimerism differed between each of the various lineages in individual animals, suggesting that the degree of allogeneic chimerism may be independently regulated for each hematopoietic lineage.

TABLE 4

PHENOTYPE OF PLATELETS AND ERYTHROCYTES IN MIXED ALLOGENEIC CHIMERAS[a]

| Reconstitution | TBI-based regimen | % BALB/c platelets | % BALB/c RBC | % BALB/c lymphoid cells |
|---|---|---|---|---|
| BALB/c→B10 | 5 Gy + ALG | 55 | 64 | 86 |
| | | 0 | 0 | 30 |
| | | 14 | 30 | 71 |
| | 5 Gy + CyP | 71 | 100 | 99 |
| | | 78 | 100 | 98 |
| | | 69 | 100 | 91 |
| | | 31 | 100 | 92 |
| Normal B10 | — | 0 | 0 | 0 |
| Normal BALB/c | — | 100 | 100 | 99 |

[a]One representative experiment for phenotyping of platelets and erythrocytes by GPI-isomerase assay, and enzyme for which B10 and BALB/c mice differ. Lymphoid typing was performed by flow cytometry using anti-Class I $H-2^b$ and $H-2^d$ Mab. Analyses were performed using the forward and side scatter characteristic for the lymphoid gate. Results were normalized to 100% Animals were typed 2 months post reconstitution.

The single animal which exhibited lymphoid chimerism without evidence of allogeneic platelets or erythrocytes demonstrated stable lymphoid chimerism for ≧75 days post reconstitution. The lack of multilineage chimerism may be secondary to selective lineage regulation or may indicate engraftment of a lymphoid progenitor rather than engraftment of the pluripotent stem cell itself. All recipients which failed to exhibit PBL chimerism also had no evidence for allogeneic chimerism of erythroid or platelet lineages.

6.2.10. Evidence for Specific Tolerance in Vivo to Donor-Type Skin Grafts

Mixed allogeneic chimeras prepared with nonlethal conditioning were tested for evidence of donor-specific tolerance in vivo by skin-grafting. B10 recipient mice received full thickness tail skin grafts of recipient, donor (B10.BR or BALB/c), or third-party origin (BALB/c, DBA, or B10.BR) 1 to 7 months following nonlethal conditioning and reconstitution (BALB/c-B10; B10.BR-B10). Grafts were read blindly and assessed on a daily basis for signs of rejection. In all recipients there was an absolute correlation between engraftment and tolerance, since mice with documented chimerism accepted donor-type skin grafts yet rejected MHC-disparate third-party skin grafts with a time course similar to identically-conditioned but unreconstituted controls (FIG. 7). All recipients which failed to exhibit allogeneic chimerism (<0.5%) promptly rejected both donor and third-party skin grafts.

6.2.11. Functional Donor-Specific Tolerance in Vitro

Nonlethally conditioned chimeras were assessed for donor-specific tolerance and immunocompetence in vitro using MLR and CML assays directed against donor and third-party antigens. Lymphocytes from chimeras which had evidence for allogeneic engraftment were functionally tolerant to both host (B10), and donor-strain (B10.BR or BALB/c) alloantigens but were reactive to third-party alloantigens in an MLR assay (BALB/c or BR10.BR, respectively) (Table 5). All similarly treated recipients without detectable allogeneic chimerism were reactive to both donor and third-party alloantigens.

Similarly, lymphocytes from recipient animals with allogeneic chimerism failed to lyse targets with host (B10) or donor (B10.BR) alloantigens, but were fully capable of third-party (BALB/c) target lysis in CML (FIG. 8). Lymphocytes from control animals without chimerism exhibited reactivity directed against all MHC-disparate targets.

TABLE 5

REACTIVITY OF NONLETHALLY CONDITIONED MIXED ALLOGENEIC CHIMERAS IN ONE-WAY MLR[a]

| | [$^3$H]-Thymidine Incorporation (cpm ± SEM) | | | |
|---|---|---|---|---|
| Animal | Anti-B10 | Anti-BR | Anti-BALB/c | Self anti-self |
| Normal B10 | 3057 ± 133 | 43,233 ± 3,838 | 58,135 ± 3,887 | — |
| Normal B10.BR | 40,900 ± 241 | 3,608 ± 446 | 59,537 ± 2,510 | — |
| Chimera 1 | 7,173 ± 883 | 3,507 ± 208 | 86,892 ± 3,763 | 2,001 ± 127 |
| Chimera 2 | 5,264 ± 886 | 4,077 ± 527 | 67,019 ± 777 | 3,175 ± 105 |

| | Stimulation Index[b] | | |
|---|---|---|---|
| Animal | B10 | B10.BR | BABL/c |
| Normal B10 | 1.0 | 14.1 | 19.0 |
| Normal B10.BR | 11.3 | 1.0 | 16.5 |
| Chimera 1 | 3.6 | 1.7 | 43.4 |
| Chimera 2 | 1.7 | 1.3 | 21.1 |

[a]Mean ± SEM of triplicate cultures in 1:1 responder-to-stimulator ratio. Animals were tested 2–6 months following reconstitution. This is one of five representative experiments. B10.BR bone marrow was infused into B10 recipients for each of the chimeras shown.
[b]Stimulation index is a ratio of the cpm generated in response to a given stimulator over the baseline cpm generated in response to the host. (Chimera anti-stimulator/Chimera anti-self)

6.2.12. Nonlethal Preparative Regimens Result in Stable Allogeneic Chimerism and Excellent Long-Term Recipient Survival and no Evidence for GVHD All allogeneic chimeras which engrafted with allogeneic donor bone marrow (n=51) exhibited excellent survival and early evidence of donor chimerism by 3.5 to 4 weeks following bone marrow transplantation. Chimerism remained stable throughout a minimum follow-up of 3 to 4 months post reconstitution. None of the animals had evidence of GVHD for up to 8 months in follow-up. The overall mortality was less than 1%.

6.2.13. Allogeneic Engraftment After Conditioning with Nonlethal Total Body Irradiation, Anti-Lymphocyte Globulin and Cyclophosphamide The following study was carried out to examine whether the conditioning of a recipient with the combined treatment of ALG and CyP would reduce the dosage of TBI necessary to result in stable engraftment of allogeneic donor cells. B10 mice were treated with ALG at 2 mg/mouse i.v. at day −3 before bone marrow transplantation. Then on day 0, the same animals were treated with various doses of TBI and 15×10$^6$ B10.BR or BALB/c bone marrow cells, followed by CyP (200 mg/kg) injection two days later. Mixed allogeneic chimerism was achieved in >90% of the animals conditioned with 3Gy TBI, ALG and CyP. At 2 Gy TBI, a lower but significant percentage of recipients were also engrafted with donor cells (FIG. 9). FIG. 10 shows that even at 2 Gy, the combined treatment of these regimens allowed a definite percentage of donor cell engraftment. This TBI dosage could even be reduced to 1Gy if higher numbers of donor cells were transferred. As the dosage of TBI increased, there was also a proportional increase of the percentage of donor cell engraftment in the recipients. FIG. 11 illustrates that when the conditioning was performed at 3Gy of TBI, the combined use of TBI, ALG and CyP was the only method capable of producing a substantial percentage of donor cell engraftment.

Although 200 mg/kg of CyP was used as the dose of choice, it was shown that the entire range of 50–200 mg/kg of CyP was able to condition a recipient in combination with TBI and ALG. Similarly, ALG yielded positive conditioning results when administered at 0.5–2 mg/animal. Additionally, a higher number of donor cells always produced higher levels of engraftment. This was demonstrated when BALB/c donor cells were used in place of B10.BR. Since BALB/c cells were incompatible with B10 recipients at both the MHC and minor antigens, it generally required a stronger conditioning treatment to achieve BALB/c cell engraftment than that necessary for B10.BR. This could be accomplished by increasing the dosage of any one of the three regimens, or alternatively, by a higher number of donor cells.

The engraftment of donor cells was stable and in diverse blood cell lineages, including T cells, B cells, NK cells, RBC, granulocytes, platelets and macrophages. When the animals were transplanted with skin grafts from the donor, donor-specific transplantation tolerance was observed, but third party grafts were rejected. Similar pattern of reactivity was confirmed in MLR and CML. The combined use of three regimens was non-lethal, since all treated animals survived for more than 100 days, while all mice treated with TBI at 9.5Gy died by day 10.

7. EXAMPLE

Xenogeneic Bone Marrow Cells Engraft in Recipients Conditioned by Non-Lethal Methods

7.1. Results

A similar non-lethal radiation-based model has been established in which rat bone marrow stem cells engrafted stably (≧8 months) in mouse recipients. A sigmoidal curve was also observed when the percentage of animals with donor cell engraftment was compared with varying doses of irradiation (FIG. 1). This curve was shifted slightly to greater radiation doses as compared to the conditions sufficient for allogeneic engraftment, since only 28.6% of the animals engrafted at 6.5 Gy. A higher proportion of rat donor cell engraftment occurred with increasing sub-lethal doses of radiation. At 7.5 Gy, all mice demonstrated evidence of rat stem cell engraftment. Again, the animals exhibited multilineage chimerism, including the presence of rat αβ-TCR$^+$ T cells, B cells, NK cells, monocytes, platelets and red blood cells.

In addition, the xenogeneic chimeras also displayed functional donor-specific tolerance to both host and donor cells, while their responses to MHC-disparate third-party rat or mouse stimulator cells remained intact. In vivo, the chimeras accepted xenogeneic pancreatic islet grafts from the same donors, whereas they readily rejected third-party rat islets. Thus, the data obtained from xenogeneic bone marrow transplantation studies confirmed the successful use of a non-lethal conditioning regimen, indicating the importance of the hematopoietic microenvrionment in xenogeneic donor cell engraftment.

8. EXAMPLE

Allogeneic and Xenogeneic Engraftment After Conditioning with Total Lymphoid Irradiation In addition to TBI, TLI was also tested in conditioning recipients for bone marrow transplantation. As a single dose, TLI was simply a modified form of TBI in that the method of delivery was the same way, except that only certain parts of the recipient's body was exposed to the irradiation Since TLI was a less aggressive and ablative approach, its dosage could be increased up to 10 Gy without lethal consequences. In the following study, baboons were treated with a single dose of 7.5 Gy of TLI at day 0 followed by transfer of allogeneic baboon bone marrow cells with at least one MHC disparity. In addition, certain animals were further treated with a single dose of CyP (50 mg/kg) at day +2, or two doses of CyP at day −3 and −2. The results demonstrate that the majority of baboons conditioned with 7.5Gy TLI and two doses of CyP produced stable (≧36 weeks) engraftment of up 30% donor cells. TLI with a single dose of CyP produced stable donor cell engraftment in about 50% of the treated animals. Several of the engrafted animals exhibited donor-specific tolerance in MLR assays after three months. TLI alone gave rise to donor cell engraftment in about 25% of the recipients. However, the engraftment occurred at very low levels, which was detectable only by molecular typing techniques.

Xenogeneic transplantation with human cells was also performed in baboons conditioned with TLI. Since xenogeneic barriers were usually more difficult to overcome, a baboon was treated with CyP at day −3, −2 and −1, and 9.5 Gy TLI on day 0, followed by 22×10$^8$/kg human vertebral body bone marrow cells that had been antibody-depleted to remove GVHD-producing cells such as T cells, B cells and NK cells. The animal produced chimerism with 15% human cells two months after transplantation, with no GVHD or significant morbidity.

9. EXAMPLE

Titration of Minimum Cyclophosphamide Dosage

In the initial studies 200 mg/kg of cyclophosphamide was administered in conditioning of the recipient, on the basis of the observation originally reported by Mayumi and Good (Mayumi H, Good RA. *Immunobiology* 1989; 178:287–304) that engraftment of MHC-congeneic marrow could be achieved if the recipients were treated with 100×10$^6$ spleen cells and 30×10$^6$ bone marrow cells plus 200 mg/kg of cytoxan on day 2. In this study we performed dose titrations of cyclophosphamide to determine the minimum dose sufficient to permit engraftment of highly mismatched marrow in recipients conditioned with ALG (1 mg or 2 mg on day −3) plus 300 cGy of total body irradiation. When the animals received 50, mg/kg cyclophosphamide or more on day 2 in combination with ALG plus TBI, more than 85% of the recipients engrafted (Table 6). Moreover, the chimerism was durable for at least 4 to 6 months after transplantation.

TABLE 6

INFLUENCE OF DOSE OF CYCLOPHOSPHAMIDE ON ENGRAFTMENT (B10.BR → B10)

| CYCLOPHOSPHAMIDE DOSE | NO. OF ANIMALS ENGRAFTED | | |
|---|---|---|---|
| (MG/KG) | 1 MG ALG | 2 MG ALG | TOTAL |
| 0 | 1/4 | 1/5 | 2/9 |
| 50 | 2/2 | 1/1 | 3/3 |
| 100 | 2/2 | 2/2 | 4/4 |
| 150 | 3/4 | 2/2 | 5/6 |
| 200 | 5/6 | 7/8 | 12/14 |

Animals conditioned with 1 or 2 mg ALG (injected intravenously) 3 days before irradiation with 300 cGy and transplantation of 15 × 10⁶ allogeneic bone marrow cells received various doses of cyclophosphamide on day 2. A dose of 50 mg/kg was sufficient to allow donor bone marrow engraftment in 100% of recipient mice.

10. EXAMPLE

In Vivo Depletion of Host CD4⁺ and CD8⁺ Cells Permits Engraftment of Bone Marrow Stem Cells and Tolerance Induction with Minimal Conditioning In the present study we extended our established model for incomplete recipient conditioning to determine which cells in the host must be removed to permit engraftment of MHC-disparate marrow. In vivo depletion of CD4⁺ and CD8⁺ in the recipient was sufficient to substitute the ALG pretreatment with the established 300 cGy plus 200 mg/kg cyclophosphamide (day 2) model. Recipient pretreatment with anti-CD4 antibodies alone did not permit engraftment in four animals, whereas all CD8-depleted animals engrafted. These data suggest that host CD8⁺ T lymphocytes play a critical role in alloresistance to engraftment. Specific targeting of host cells in the hematopoietic environment may allow a focused approach to achieve chimerism and tolerance with minimum recipient morbidity.

10.1. Materials and Methods

10.1.1. Animals

Male 3- to 5-week-old C57BL/10SnJ (B10), B10.BR-H2$^k$ Tla$^a$/SgSnJ (B10.BR), or BALB/cByJ (BALB/c) mice were purchased from the Jackson Laboratory (Bar Harbor, Me.) and housed in a pathogen-free facility at the Institute for Cellular Therapeutics, Allegheny University of the Health Sciences, Philadelpia, Pa.

10.1.2. Dose Titration

For the dose titration, experimental animals were treated with 1 or 2 mg ALG on day −3, 300 cGy irradiation at day 0, and with reconstitution with 15×10⁶ untreated allogeneic bone marrow cells at day 0, followed by the administration of the test dose of cyclophosphamide at day 2.

10.1.3. Antibody Conditioning

For the in vivo depletion studies, 100 μg of the appropriate antibody was injected intravenously at days −3 and −1 before bone marrow transplantation. Cyclophosphamide (200 mg/kg; Sigma Chemical Co., St. Louis, Mo.) was administrated by intraperitoneal injection on day 2. The antibodies anti-CD4 (TIB207) and anti-CD8 (TIB105); (American Type Culture Collection, Rockville, Md.) were diluted in phosphate-buffered saline solution (Biowhittaker, Walkersville, Md.) to 1 ml and injected intravenously through the lateral tail vein. Complete depletion was documented by flow cytometric analysis of peripheral blood lymphocytes (PBLs) obtained by tail bleeding.

Phycoerythrin-conjugated anti-CD4 (L3T4) and anti-CD8 (Ly2) antibodies (Pharmingen, San Diego, Calif.) were used to document depletion; fluorescein-conjugated mouse-anti-rat immunoglobin G (IgG, MCA159F; Serotec, Kidlington, Oxford, U.K.) was used to detect cells that were coated with antibody. Control animals were treated with 1 mg ALG at day −3 and 200 mg/kg cyclophosphamide at day 2.

10.1.4. Flow Cytometry

Recipients were characterized for donor cell engraftment using flow cytometry (FACS II, Becton Dickinson; Mountain View, CA) to determine the presence of peripheral blood lymphocytes bearing H-2$^b$, H-2$^k$, and H-2$^d$ encoded antigens as described (Jeffries et al., 1985, *J Exp Med* 117:127).

Briefly, peripheral blood was collected through tail bleeding into heparinized plastic serum vials. 200 μl of Medium 199 (Gibco Laboratories; Grand Island, N.Y.) were added to each vial. After thorough mixing, the suspension was layered over 1.5 ml of room temperature Lymphocyte Separation Medium (LSM) (Organon Teknika; Durham, N.C.) and centrifuged at 37° C. (400 g×20 minutes). The buffy coat layer was aspirated from the Medium 199-LSM interface and washed with medium. Lymphocytes were stained with fluorescein-conjugated monoclonal antibodies for donor- and host-specific class I antibodies H2K$^b$ (AF6-88.5), H2K$^d$ (SF1-1.1), and H2K$^k$ (AF3-12.1) (Pharmingen) conjugated with fluorescein and lineage markers conjugated with PE αβ-TCR (H57-597), CD4 (L3T4), CD8 (Ly2), NK1.1 (PK136), and CD45R/B220 (RA3-603) (Pharmingen) and MAC-1 (Ml/70) (Boehringer Mannheim, Indianapolis, Ind.) for 45 minutes at 4° C.

10.1.5. Induction of Chimerism

Chimeras were prepared as previously described. McCarthy SA, et al., *Transplantation* 1987; 44:97–105. Cobbold SP, et al., *Nature* 1986; 323:164–6. The bone marrow stem cell produces at least 11 different cell types, including αβ and δτ T cells, B cells, macrophages, and NK cells. To evaluate whether the donor pluripotent hematopoietic stem cell had engrafted, chimeras were evaluated at 6 months by two-color (antidonor versus lineage) flow cytometric analysis. Donor-derived αβ-TCR⁺ T cells, CD4⁺ and CD8⁺ cells, B cells, NK cells, and macrophages were present (FIG. 12).

10.2. Results

10.2.1. Chimerism with Partial Recipient Conditioning: Targeting ff CD4+and CD8⁺ Cells in the Recipient Marrow Space Permits Chimerism with Reduced Conditioning It has been demonstrated in rodent models as well as in primates, including humans, that tolerance for solid organ transplantation can be achieved by bone marrow chimerism. Even chronic rejection appears to be prevented. The clinical application of this technique has been limited by the toxicity of lethal conditioning, which is believed to be necessary to achieve bone marrow stem cell engraftment in MHC-disparate donor/recipient combinations. We previously reported that transplantation of MHC-disparate bone marrow into recipients conditioned with a single dose of Anti-Lymphocyte-Globulin (ALG) on day −3 followed by 300 cGy TBI day 0 and 200 mg/kg Cyclo-phosphamide (CyP) on day +2 results in stable mixed chimerism and donor-specific tolerance for solid organ grafts. ALG is a polyclonal serum that binds to NK cells as well as to CD4$^+$ and CD8$^+$ cells. The focus of the present study has been to define by substitution with mAb, which of the cell populations that are targeted by ALG pretreatment (pretreat) block engraftment. C57BL/10SnJ (H2$^b$) mice were pretreated i.v. with 50 μl anti-CD4 (TIB207) and 100 μl anti-CD8 (TIB 105) day −3 and −1. Successful depletion was documented by flow cytometry analysis of PBI. The animals were irradiated with 300cGy and transplanted with 15×10$^6$ B10.BR/SgSnJ (H2$^k$, n=4) or BALB/c (H2$^d$, n=3) bone marrow cells followed by 200 mg/kg CyP i.p. day +2. Without ALG-pretreatment historically only 20% of animals engrafted compared to 71% of anti-CD4 and CD8 pretreated animals. This is similar to the increased engraftment (engr.) seen with ALG pretreatment. In addition the level of chimerism was highest in animals with mAb (Table 7).

TABLE 7

CHIMERISM WITH PARTIAL RECIPIENT CONDITIONING: TARGETING OF CD4$^+$ AND CD8$^+$ CELLS IN THE RECIPIENT MARROW SPACE PERMITS CHIMERISM WITH REDUCED CONDITIONING

| CONDITIONING | | ENGR. ANIMALS | LEVEL OF ENGR. |
|---|---|---|---|
| no pretreat. | (n = 5) | 20% | 22 ± 0% |
| ALG-pretreat. | (n = 12) | 83% | 30 ± 7.4% |
| CD4/CD8 pretreat. | (n = 7) | 71% | 53 ± 0.1% |

We conclude that CD4$^+$ and/or CD8$^+$ cells in the recipients hematopoietic environment play an important role in resistance to engraftment of allogeneic bone marrow. It appears from these data, that CD4$^+$ and/or CD8$^+$ cells rather than NK cells are the population(s), that block allogeneic engraftment and are removed by ALG. As we better understand mechanisms of engraftment, specific targeting of recipient cell populations will be possible.

10.2.2. Host Pretreatment with Anti-CD4 and Anti-CD8 Antibodies Replaces the Reqiurment for ALG To evaluate whether the CD4$^+$ or the CD8$^+$ cell population in the host hematopoietic microenvironment was the target of the ALG pretreatment, we administered monoclonal antibodies specific for T-cell markers (CD4 and CD8) instead of ALG. Animals were conditioned with 100 μg of CD8, CD$^4$, or CD4 plus CD8 mAbs on days −3 and −1 and then received 300 cGy of TBI followed by transplantation of 15×10$^6$ untreated allogeneic bone marrow cells and intraperitoneal injection of 200 mg/kg cyclophosphamide on day 2. To confirm the effectiveness of in vivo depletion of the targeted cell populations after mAb pretreatment, we obtained and evaluated PBL by flow cytometric analysis on day 0 (FIG. 13). The combination of anti-CD4 plus anti-CD8 recipient pretreatment resulted in donor engraftment at a frequency and level similar to that seen after ALG pretreatment (Table 8). Animals were monitored for at least 5 months. In striking contrast, when only CD4$^+$ cells were targeted, none of the recipients engrafted. However, targeting of CD$^8$+cells in the host was sufficient to substitute for the ALG effect. The levels of donor chimerism were substantial and ranged from 63.2% to 82.0% of the lymphoid gate.

TABLE 8

ANTI-CD4 PLUS ANTI-CD8 BUT NOT ANTI-CD4 ALONE IS SUFFICIENT TO REPLACE ALG PRETREATMENT

| GROUP | PRETREATMENT | NO. OF ANIMALS ENGRAFTED (%) | LEVEL OF ENGRAFTMENT (%) |
|---|---|---|---|
| 1 | 0 | 4/14 (18.8) | 14.7 ± 6.8 |
| 2 | 1 mg ALG | 5/6 (83.3) | 56.6 ± 9.7 |
| 3 | 100 μg anti-CD4 100 μg anti-CD8 | 13/17 (76.5) | 53.0 ± 8.8 |
| 4 | 100 μg anti-CD4 | 0/4 (0.0) | — |
| 5 | 100 μg anti-CD8 | 3/3 (100.0) | 73.7 ± 9.6 |

Animals pretreated with in vivo depletion of CD4$^+$ and CD8$^+$ cells or CD8$^+$ cells alone before irradiation with 300 cGy and transplantation of 15 × 10$^6$ untreated bone marrow cells and administration of 200 mg/kg cyclophosphamide engraft in the same frequency and at approximately the same level as animals treated with 1 mg ALG (injected intravenously) 3 days before transplantation (groups 3 and 5). Frequency and level of engraftment are much higher than in animals that were not pretreated (group 1). Depletion of CD4$^+$ cells alone had no effect (group 4).

10.2.3. Host CD8$^+$ Cells Play a Major Role in Resistance to Engraftment of Bone Marrow for Tolerance Induction To further characterize which cell populations in the recipient hinder engraftment, we focused in this study on the different roles of CD4$^+$ and CD8$^+$ cells using knock-out (KO) mice deficient in production of CD8$^+$ or CD4$^+$ cells. C57BL/6-Cd4$^{Tm/mak}$ (CD4-KO) and C57BL/6-Cd8$^{Tm/mak}$ (CD8-KO) mice were conditioned with 300 cGy TBI, transplanted with 15×10$^6$ B10.BR/SnJ bone marrow cells, and received 200 mg/kg CyP 2 days after bone marrow transplantation (BMT). Chimerism was assessed by flow cytometry 28 days and 4 months after BMT with mAb against donor (H2Kk) and host (H2K$^b$) MHC class I antigens. All CD8-KO mice engrafted at this low level of irradiation (n=16). The average level of chimerism was 48.7%±18.1% (range 12.9%–69.1%) at 28 days. The engraftment was durable in a follow up ≧4 months, when the average level of chimerism was 18.7%±11.3% (range 9.5%–33.5%). The engraftment was also multilineage, evidenced by the presence, at 4 months post-BMT, of B-cells, TCR$^+$ T-cells, macrophages, and natural killer cells of donor as well as host origin. At 4 months post-BMT, CD8$^+$ cells were present and exclusively of donor origin, demonstrating that positive selection mediated by Class I molecules had taken place in the recipient. In striking contrast, none of the CD4-KO mice engrafted (n=15). We conclude that CD8$^+$ rather than CD4$^+$ lymphocytes in the recipient mediate rejection of donor bone marrow (Table 9). The concept of HSC chimerism could provide an additional advantage for patients with genetic deficiencies as the cause of organ failure, allowing for the cure of certain deficiencies of soluble enzymes or cell populations along with the induction of tolerance, as with the lack of CD8$^+$ cells in CD8-KO mice.

TABLE 9

HOST CD8+ CELLS PLAY A MAJOR ROLE IN RESISTANCE
TO ENGRAFTMENT OF BONE MARROW FOR TOLERANCE
INDUCTION

| MOUSE STRAIN | N. | % ANIMALS THAT ENGRAFTED | DONOR CHIMERISM (day 28) |
|---|---|---|---|
| CD4-KO | 15 | 0 | none |
| CD8-KO | 16 | 100 | 48.7% ± 18.1% |

10.3. Discussion

A number of nonmalignant diseases are potentially treatable by bone marrow transplantation. It is important to identify strategies to achieve engraftment with minimum recipient morbidity. To develop such strategies we must understand the mechanisms of engraftment. Two categories are necessary for engraftment to occur in allogeneic bone marrow transplantation: (1) the requirement for space or niches and (2) control of host-anti-donor alloreactivity.

It is still debated whether hematopoietic space is physical or conceptual. In syngeneic recipients, conditioning of the recipient is necessary to achieve engraftment if physiologic doses of bone marrow cells are used. Down J D, et al., *Blood* 1991; 7:661–9. Tomita Y, et al., *Blood* 1994; 83:939–48. Down et al. showed that approximately 200 cGy TBI is required to achieve engraftment of $10 \times 10^6$ syngeneic bone marrow cells. Tomita et al. achieved engraftment with $15 \times 10^6$ cells and 150 cGy irradiation, and we recently reported durable engraftment with $20 \times 10^6$ bone marrow cells and 100 cGy irradiation. The requirement for conditioning in syngeneic recipients can only be overcome with very high cell doses. Brecher G., et al., *Proc. Natl. Acad. Sci. USA* 1982; 79:5085–7. Stewart F M, et al., *Blood* 1993; 81-2566–71. Moreover, even in minor antigen disparities, engraftment cannot be achieved without conditioning. Together these observations show that apart from alloresistance, a need for space exists, and that this requirement for engraftment must be understood to allow a more focused approach for conditioning.

A second requisite to engraftment is to overcome radioresistant alloreactive cells in the host that can reject donor marrow. Historically, nonspecific immunosuppressive agents have been used to control host-anti-donor alloreactivity in bone marrow transplantation. These agents function in a nonspecific fashion, and many cell types are the target of their reactivity. In this study we identified that a partial dose of cyclophosphamide (50 mg/kg) was sufficient to permit engraftment in the mouse.

A precise understanding of which cell types mediate alloresistance to engraftment would allow a more focused approach to conditioning. When mice were conditioned with ALG, cyclophosphamide on day 2, and TBI we determined that ALG more effectively removed the CD4+ and CD8+ cells than it did the NK cells. This finding suggests that these cell types may play a critical role in alloresistance to engraftment. Colson Y L, et al., *J. Immunol.* 1996; 157:2820–9. We have now extended that observation to an in vivo model and have confirmed that CD8+ T cells in the host do indeed mediate alloresistance to engraftment because in vivo removal of those cells from the host was sufficient to permit engraftment of MHC-disparate bone marrow. It is noteworthy that CD8+ cells were more important in the engraftment because removal of host CD4+ cells alone did not permit engraftment.

The model for mixed chimerism provided another approach to study which cellular components in the host hematopoietic environment must be removed to allow engraftment of donor bone marrow. When a mixture of T-cell depleted (TCD) syngeneic plus TCD allogeneic bone marrow is administered to completely ablated (950 cGy) mouse recipients, mixed chimerism results. In one of our former studies T-cell depletion was performed by using rabbit anti-mouse brain, polyclonal serum with a broad specificity for a number of cell types. When the syngeneic component is not TCD, recipients repopulate as 100% syngeneic, regardless of the treatment of the allogeneic component. Ildstad S T, et al., *J. Immunol.* 1986; 136:28–33. When monoclonal antibodies were used to deplete specific cellular subsets in the syngeneic marrow, it was determined that the cell subpopulation responsible for the effect was a CD8+ cell. Ildstad S T, et al., *J. Exp. Med.* 1986; 163:1343–8. As an extension of these observations, our data support the role of a CD8+ host T cell as the primary effector for alloresistance. In our study the depletion of CD4+ cells alone did not result in durable multilineage engraftment, whereas depletion of CD8+ cells alone permitted engraftment at a frequency comparable to the combination of CD4+ and CD8+.

In summary, these data suggest that host CD8+ T cells play a critical role in resisting engraftment of MHC-disparate bone marrow in the mouse. In recipients depleted of CD4+ and CD8+ cells durable multilineage chimerism can be achieved with $15 \times 10^6$ bone marrow cells, 300 cGy irradiation, and the administration of 200 mg/kg cyclophosphamide 2 days after transplantation. Specific targeting of host cell populations that resist engraftment may provide a focused approach to achieving engraftment with minimum recipient morbidity. As less toxic strategies for BMT emerge, a number of diseases that were originally precluded from this therapy because of morbidity and mortality could potentially be treated. These include (1) autoimmune diseases including diabetes, (2) hemoglobinopathies including sickle cell disease, (3) enzyme deficiency states including chronic granulomatous disease, and (4) transplantation rejection of primarily vascularized allografts and xenografts.

10.3.1. A Partial Conditioning Approach to Mixed Allogeneic Chimerism in Non-Obese Diabetic (NOD) Mice Pancreas or islet transplantation is the preferred approach to restore glucose homeostasis in patients with Type I diabetes. However, life-long immunosuppression is required to prevent rejection of the graft. Immunosuppressive drugs are associated with side effects including end organ toxicity, infectious complications, and development of malignancies. Moreover, although immunosuppressive drugs control acute rejection, they do not adequately prevent chronic rejection. Finally, the systemic autoimmune process that results in β-cell destruction is not halted. Mixed allogeneic chimerism induced with bone marrow transplantation (BMT) halts the autoimmune disease and induces donor-specific tolerance with preserved anti-third-party reactivity. The morbidity and mortality associated with lethal conditioning cannot be justified in the application of mixed chimerism to induce tolerance. We report here a partial ablative conditioning strategy for induction of mixed chimerism in non-obese diabetic (NOD) mice. NOD/MrKTacBr (NOD) mice were conditioned with: A) 600 cGy total body irradiation (TBI) alone; B) 100 μg monoclonal antibody against CD4, CD8, Thy1.2 or H2D$^b$ administered intravenously on day 5, 3 and 1 prior to transplantation and 600 cGy TBI or; C) 600 cGy TBI followed by intraperitoneal injection of 200 mg/kg Cyclophosphamide (CyP) two days after transplantation. The animals were transplanted with $55\times10^6$ or $60\times10^6$ B10.BR/SgnSnJ bone marrow cells, respectively.

TABLE 10

| CONDITIONING | ANIMALS WITH ENGRAFTMENT | PERCENTAGE DONOR CHIMERISM |
|---|---|---|
| 600 cGy | 0/10 | — |
| 600 cGy + anti-H2D$^b$ | 0/3 | — |
| 600 cGy + anti-Thy1.2 | 0/2 | — |
| 600 cGy + anti-CD4 | 0/2 | — |
| 600 cGy + anti-CD8 | 1/3 | 98.9% |
| 600 cGy + CyP | 4/4 | 91.2 ± 5.1% |

100% of animals engrafted when a single dose of CyP was added to the 600 cGy TBI (Table 10). The development of partial conditioning strategies with minimal recipient toxicity may allow application of BMT to induce tolerance to pancreatic and islets allografts as well as to reverse the autoimmune process by inducing tolerance to self antigens.

11. EXAMPLE

A Partial Conditioning Model to Achieve Hematopoietic Stem Cell Chimerism in Mice with Type 1 Diabetes Type 1 diabetes is a systemic autoimmune disease in which the insulin-producing islets are destroyed. The complications of diabetes are minimized with tight glucose control. The preferred approach for glucose homeostasis in patients with Type 1 diabetes is whole pancreatic or islet allograft transplantation. Graft survival is currently dependent upon the daily use of chronic nonspecific immunosuppression. The use of these agents is associated with an increased risk of malignancy and infection. Moreover, chronic rejection remains the primary cause of late graft loss in spite of the use of the agents. The induction of tolerance to donor antigens through chimerism may eliminate the requirement for nonspecific immunosuppression. Mixed donor/host hematopoietic stem cell (HSC) chimerism is associated with donor-specific tolerance for solid organ and cellular transplants in animal models. However, the morbidity and mortality associated with fully ablative conditioning could not be justified in attempts to induce tolerance. The development of partial conditioning strategies to make space for the donor HSC to take may allow the application of bone marrow transplantation (BMT) for the induction of tolerance to whole pancreas as well as islet allografts in patients with Type 1 diabetes.

We previously reported that chimerism and tolerance could be achieved in normal disease-resistant mice with partial conditioning using total body irradiation (TBI) plus cyclophosphamide. We have now extended this model to the nonobese diabetic (NOD) mouse, a model for Type 1 diabetes. NOD mice demonstrate a relative resistance to engraftment compared to disease resistant strains. While 600 cGy TBI is sufficient conditioning to make space to achieve HSC chimerism in normal mice, as high as 750 cGy TBI is required to condition NOD recipients to make space for HSC chimerism. The goal of the present studies was to identify a strategy to overcome the alloresistance to chimerism in NOD mice by further reducing the irradiation dose for conditioning. NOD mice were treated with two different conditioning approaches and then transplanted with $60\times10^6$ unmodified B10.BR bone marrow cells: A) 600 cGy total body irradiation (TBI) alone; B) 600 cGy TBI followed by a single intraperitoneal injection of 50 mg/kg of Cyclophosphamide (CyP) two days after bone marrow transplantation. There was no engraftment with radiation alone (Group A n=10), while in group B there was 100% engraftment with a 91.5% donor chimerism (FIG. 15). These data suggest that although NOD mice exhibit a relative alloresistance to conditioning and HSC chimerism, this barrier can be overcome with space-making agents, such as cyclophosphamide. Studies are in progress to identify which specific cells in the recipient bone marrow must be removed co make space for the donor HSC tc engraft. Partial conditioning strategies such as these may allow HSC chimerism to be applied clinically for the induction of tolerance to islet or pancreas transplants in patients with Type 1 diabetes.

12. EXAMPLE

A Partial Conditioning Approach to Achieve Mixed Chimerism in the Rat: Depletion of Host Natural Killer Cells Significantly Reduces the Amount of Total Body Irradiation Required for Engraftment

12.1. Materials and Methods

12.1.1. Animals

Five- to 8-week-old male ACI (RT1A$^a$) and Wistar Furth (WF; RT1A$^U$) rats were purchased from Harlan Sprague Dawley (Indianapolis, Tenn.) (Gill, T J et al., 1987, *Transplantation*, 43:773). Animals were housed in a barrier animal facility and cared for according to National Institutes of Health animal care guidelines at the Institute for Cellular Therapeutics, Allegheny University of the Health Sciences.

12.1.2. T Cell Depletion of Bone Marrow Using Immunomagnetic Beads

Bone marrow was harvested as described previously (Ildstad, S. T., and D. H. Sachs, 1984, *Nature*, 307:168) from femurs and tibias of ACI rats by flushing with media 199 (MEM; Life Technologies, Rockville, Md.) containing 10 μg/mL gentamycin (Life Technologies) using a 22½ gauge needle. Cells were gently resuspended using an 18½ gauge needle and filtered through a sterile nylon mesh. Bone marrow cells were washed, resuspended in MEM and counted. Cells were incubated with purified anti-αβTCR mAb (R73; mouse IgG, Pharmingen, San Diego, Calif.) for 30 mm at 4° C. in the dark. Bone marrow cells were washed twice in 1× Hanks' balanced salt solution (HBSS; Life Technologies) containing 10% fetal bovine serum (Life Technologies) and incubated for 60 min. with immunomagnetic beads (Dynabeads M-450; goat anti-mouse IgG; Dynal, Lake Success, N.Y.). For the negative selection of T cells, tubes with the bone marrow cell suspension were placed in magnetic cell separator (BioMag Separator; Advanced Magnetics, Cambridge, Mass.) for 5 min. and unbound cells were carefully aspirated. Cell separation was repeated. Bone marrow cells were washed, counted and resuspended in MEM at a concentration of $100\times10^6$ bone marrow cells per 1 ml. To confirm adequacy of depletion of αβTCR+ T cells, bone marrow cells were analyzed by flow cytometry prior to bead depletion, following incubation with primary mAb and after final depletion. Cells were incubated with either anti-αβTCR-FITC (R73; mouse IgG$_1$ Pharmingen) or goat anti-mouse Ig-FITC (Pharmingen) for 30 min., washed twice in FACS medium (prepared in laboratory) and fixed in 2% paraformaldehyde (Tousimis Research Corporation, Rockville, Md.). Flow cytometric analysis was performed on a FACSCalibur (Becton & Dickinson, Mountain View, Calif.).

12.1.3. Host Conditioning and Reconstitution

WF rats were conditioned with an unfractionated TBI dose from a Cesium source (Nordion, Ontario, Canada) at a dose rate of 115 cGy/min. Certain recipient rats were pretreated with anti-NK mAb (NK3.2.3; mouse IgG$_1$) that selectively depletes NK cells in vivo (Van den Brink, et al., 1990, *J.Exp.Med.*, 171:197). Animals were injected intraperitoneally (IP) with 100 μl anti-NK ascites (containing a total protein concentration of 10 mg/ml of which 3 mg/ml was monoclonal IgG$_1$) diluted in 1 ml HBSS on days −3 and −2 prior to transplantation. Another group of recipients was pretreated with either 1 ml (10 mg) of rabbit-anti-rat lymphocyte serum (ALS; Accurate Chemical Co., Westbury, N.Y.) IP on day −5 alone or ALS in combination with anti-NK3.2.3 mAb. Recipients were reconstituted with 100× 10$^6$ TCD bone marrow cells from ACI rats diluted in 1 ml MEM via penile vein injection within 6 hours after TBI.

12.1.4. Assessment of in Vivo NK Cell Depletion

Peripheral blood (PB) was obtained on day 0 from rats treated with anti-NK mAb on days −3 and −2 and stained with anti-NK3.2.3-FITC and anti-αβTCR-PE mAb for two-color-flow cytometric analysis. Staining was also performed with goat anti-mouse Ig-FITC to assure hat cells were depleted and not simply coated with nti-NK mAb.

12.1.5. Assessment of NK Cells and T Cells After Conditioning

Animals conditioned with TBI alone or TBI plus in vivo depletion with anti-NK mAb but not reconstituted with rat bone marrow were euthanized on day +1. Spleen, thymus and PB were obtained and single cell suspensions were prepared. Cells were stained for flow cytometric analysis using anti-αβTCR-FITC, anti-NK3.2.3-FITC and goat anti-mouse Ig-FITC to determine the percentage of T cells and NK cells remaining after conditioning. Dead cells were excluded by staining with propidium iodide (PI; Sigma, St. Louis, Mo.).

12.1.6. Characterization of Chimeras by Flow Cytometry

Engraftment of allogeneic bone marrow was assessed 4 weeks following bone marrow transplantation (BMT) using flow cytometry to determine the percentage of peripheral blood lymphocytes (PBL) bearing ACI or WF MHC class I antigen. Whole blood was collected in heparinized plastic vials and aliquots of 100 μl were stained with purified anti-rat RT1A$^a$ mAb (NR3/31; rat IgG$_{2a}$; Serotec) and biotinylated anti-rat RT1A$^{a,b}$ mAb (C3; LOU/cN IgG$_{2b}$; Pharmingen). After two washes in FACS medium cells were counterstained with anti-rat IgG$_{2b}$-FITC (RG7/1.30; mouse IgG$_{2b}$; Pharmingen) or streptavidin conjugated APC (Becton & Dickinson). Red blood cells were lysed using ammonium chloride lysing buffer (ACK; prepared in laboratory). Cells were washed again and fixed in 2% paraformaldehyde.

Multilineage analysis was performed on PB obtained from chimeras by two-color-flow cytometry 10 or 12 months after reconstitution. Multiple lineages including αβTCR+ T cells (anti-αβTCR-FITC), B cells (anti-CD45RA-FITC; OX-33; mouse IgG$_1$Pharmingen) and macrophages/granulocytes (anti-CD11b-FITC; WT.5; mouse IgA; Pharmingen) were detected using directly labeled mAbs. Percentages of donor and recipient derived cells of each lineage were determined using anti-donor and anti-recipient MHC class I mAbs.

12.1.7. Heterotopic Cardiac Transplantation

Mixed allogeneic chimeras underwent intra-abdominal cardiac transplantation 4 to 8 weeks after reconstitution by the method of Ono and Lindsey (Ono, K., and E. S. Lindsey, 1969, J. Thorac. Cardiovasc. Surg., S 7:225). Allograft survival was assessed every 48 hours using a semiquantitative scale (0+=no palpable heart beat, 4+=visual pulsation). Rejection was defined as cessation of visible or palpable contractions and was confirmed histologically. Cardiac allografts were explanted and fixed in 10% buffered formalin for routine hematoxylin and eosin staining. The grade of inflammation and chronic rejection was quantified as described previously (Demetris, A. J. et al., 1997, Am. J. Pathol., 150:563). Briefly, the degree of inflammation was graded semi-quantitatively from 0 (none) to 4 (severe).

12.1.8. Statistical Analyses

Continuous variables are expressed as mean ±standard error of the mean, and compared using Student t-test. Inflammation scores and graft survival between groups were compared using the Mann-Whitney U-Test. For the comparison of two proportions, Fisher exact test was used. A p-value of less than 0.05 was considered to be statistically significant.

12.2. Results

12.2.1. Efficacy of T Cell Depletion of Donor Bone Marrow

To prevent GVHD donor bone marrow was T cell depleted using anti-αβTCR mAb and immunomagnetic beads. Efficacy of T cell depletion was confirmed by flow cytometry. Prior to T cell depletion the percentage of αβTCR+ T cells in total bone marrow cells ranged from 1.22% to 2.29% (average 1.8%) (FIG. 17 A). After incubation of bone marrow cells with anti-αβTCR mAb sufficient labeling was confirmed by staining with secondary mAb (FIG. 17 B). Following immunomagnetic bead depletion the percentage of αβTCR+ T cells was reduced to an average of 0.12% (range 0.05% to 0.18%) (FIG. 17 C). The mean depletion of αβTCR+cells from bone marrow was 97% (range 90% to 99%). The presence of T cells coated with anti-αβTCR mAb was excluded by staining cells with secondary mAb after depletion procedure. The average T cell dose per kg recipient bodyweightwas $1.45 \times 10^5 \pm 1.4 \times 10^4$.

12.2.2. Efficacy of in Vivo Depletion Using Anti-NK mAB

To confirm that pretreatment of recipients with anti-NK mAb on days −3 and −2 prior to TBI and BMT effectively depleted host NK cells, PB was examined by two-color-flow cytometry on day 0 for the presence of NK cells as well as T cells (FIG. 18). The percentage of PBL showing positive staining with anti-NK3.2.3 mAb in untreated WF rats averaged 11%. The NK3.2.3+ population could be divided into cells with bright staining with anti-NK mAb (NK3.2.3$^{bright}$) and cells with a dim expression of NK3.2.3(NK3.2.3$^{dim}$). NK3.2.3$^{dim}$ cells coexpressed αβTCR and are characterized as T/NK cells (FIG. 18 B). In WF rats treated with anti-NK mAb on days −3 and −2 complete depletion of cells expressing NK3.2.3 (including both NK$_{3.2.3}^{bright}$ and NK3.2.3$^{dim}$) was observed (FIG. 18 E). Coating of the target cell population was excluded using secondary FITC-labeled anti-mouse Ig mAb (FIG. 18 F). In vivo depletion was specific for NK cells since the fraction of αβTCR+ T cells in PB was not affected.

12.2.3. Depletion of Radio-Resistant Host NK Cells by Pretreatment with Anti-NK mAB Enhances Allogeneic Bone Marrow Engraftiment To study the mechanisms responsible for the superior engraftment of allogeneic rat bone marrow in recipients pretreated with anti-NK mAb over animals conditioned with 900 cGy TBI alone, WF rats received either anti-NK mAb on days −3 and −1 followed by 900 cGy TBI on day 0 or 900 cGy TBI alone. No bone marrow was injected and rats were euthanized on day +1. PB, spleen and thymus were analyzed using flow cytometry.

In PB of animals that received 900 cGy TBI alone the median percentage of NK cells in PI negative PBL was increased from 9% (untreated controls) to over 50%, while the percentage of T cells was reduced from 40% to 2% (FIG. 19 A and C). In contrast, pretreatment with anti-NK mAb on days −3 and −2 followed by 900 cGy TBI resulted in a complete depletion of NK cells in PB. Coating was excluded using secondary anti-mouse Ig mAb (FIG. 19 B).

An increase in radio-resistant host NK cells was also observed in the spleen of animals treated with 900 cGy alone. The median percentage of NK cells on gated PI negative splenic lymphocytes was elevated from 25% (control) to 44% (FIG. 20 A and C). When animals were pretreated with anti-NK mAb, positive staining with primary anti-NK3.2.3 mAb was detectable only in 1% of gated lymphocytes. However, more than 20% of gated lymphocytes showed positive staining with secondary anti-mouse Ig mAb indicating a high proportion of coated NK cells in the spleen of those animals (FIG. 20 B).

In thymus three different populations of thymocytes could be differentiated by their $\alpha\beta$TCR expression. Thymocytes expressing $\alpha\beta$TCR$^{bright}$ represent a relatively mature phenotype while immature thymocytes show a dim to negative expression. There was a shift towards the more immature stage of T cells in thymus of animals in both treatment groups when compared with T cells from untreated WF rats. The median percentage of mature thymocytes with a $\alpha\beta$TCR$^{bright}$ expression was reduced from 11% in naive WF rats to 3% after TBI alone and 5% after anti-NK mAb treatment plus TBI. The percentage of $\alpha\beta$TCR$^-$ thymocytes increased from 19% in untreated controls to 26% in irradiated and 30% in mAb-treated and irradiated WF rats (FIG. 21).

12.2.4. Establishment of an Irradiation-Based Model for Conditioning: Titration of the TBI Dose Sufficient for Bone Marrow Engraftment To define the minimum amount of TBI required for engraftment of 100×10$^6$ TCD donor bone marrow cells, MHC-plus minor-disparate rat recipients were conditioned with varying amounts of TBI. The incidence of engraftment and level of donor chimerism were assessed 28 days after reconstitution by flow cytometry. After TBI with 1100 cGy (n=6) and 1000 cGy (n=12), 100% of recipients engrafted and the average level of donor chimerism was 92% and 89%, respectively (FIG. 22). When the TBI dose was reduced to 900 cGy, engraftment occurred in only 1 of 8 recipients (12.5%). The level of donor chimerism in this engrafted recipient was 15%. No engraftment was detectable in animals conditioned with 800 cGy TBI (n=4).

12.2.5. Effect of in Vivo Depletion of Host NK Cells on the Level of TBI Sufficient for Engrafiment of Allogeneic Bone Marrow In order to assess the role of host NK cells in allogeneic bone marrow engraftment, we constructed TBI dose-titration curves for allogeneic recipients, which had been NK cell depleted. In vivo NK cell depletion of the recipient shifted the TBI curve to the left, permitting reliable bone marrow engraftment with significantly lower TBI doses than in recipients receiving TBI alone (p<0.001) (FIG. 22). A TBI dose of 900 cGy was sufficient to achieve engraftment in 92% (11/12) of recipients depleted of NK cells. The mean level of donor chimerism among those engrafted animals was 41%. In contrast, only 1 out of 8 (12.5%) animals conditioned with 900 cGy TBI alone showed engraftment of donor bone marrow. When recipients were conditioned with ≧800 cGy TBI alone or TBI plus pretreatment with anti-NK mAb, donor bone marrow engraftment was not detectable in any of these animals.

12.2.6. Effect of ALS Alone or in Combination with Anti-NK mAb on the Requirement of TBI We hypothesized that residual alloreactive host T cells are important for rejection of the bone marrow graft. In order to abrogate the effect of this cellular population, we treated recipients with either ALS on day −5 alone or ALS in combination with anti-NK mAb on days −3 and −2 followed by TBI on day 0. Pretreatment with ALS alone or the combination of ALS and anti-NK mAb did not result in enhanced bone marrow engraftment over anti-NK mAb treatment alone (Table 11). One hundred percent and 86% of recipients pretreated with ALS alone (n=4) or ALS plus anti-NK mAb (n=6) showed engraftment of donor bone marrow at 900 cGy TBI, respectively. The mean level of donor chimerism was 45% and 52% after pretreatment with ALS alone or ALS plus NK3.2.3 mAb, respectively. At 800 cGy TBI, none of the animals pretreated with ALS alone (n=4), anti-NK mAb alone (n=4) or a combination of the two (n=4) engrafted.

TABLE 11

ENGRAFTMENT AND LEVEL OF DONOR CHIMERISM IN WF RATS TRANSPLANTED WITH 100 × 10$^6$ TCD BONE MARROW CELLS FROM ACI RATS: INFLUENCE OF RECIPIENT PRETREATMENT ON THE REQUIREMENT FOR TBI DOSE

| TBI dose [cGy] | Pretreatment | Percentage of engrafted animals | Level of donor chimerism* (Mean ± SEM) |
|---|---|---|---|
| 900 | none | 13% (1/8) | 15% |
|  | anti-NK mAb (day −3,−2) | 92% (11/12) | 41% ± 10% |
|  | ALS (day-5) | 100% (4/4) | 45% ± 13% |
|  | ALS + anti-NK mAb | 86% (6/7) | 52% ± 11% |
| 800 | none | 0% (0/4) | — |
|  | anti-NK mAb (day −3,−2) | 0% (0/4) | — |
|  | ALS (day-5) | 0% (0/4) | — |
|  | ALS + anti-NK mAb | 0% (0/4) | — |

*Only animals that engrafted were considered

12.2.7. Kinetics and Characteristics of Achieved Chimerism

Representative ACI→WF chimeras (n=7) treated with anti-NK mAb plus 900 cGy TBI and transplanted with 100×10$^6$ TCD bone marrow cells were followed for ≧10 months after reconstitution. All transplanted animals appeared healthy and no signs of GVHD were present. In fact, ACI→WF chimeras reached their pretransplantation body weight within 2 to 3 weeks after BMT and gained weight comparable to untreated littermates. Stable donor chimerism was achieved in 6 of 7 mixed chimeras (Table 12). Only in one animal that presented with an initial level of donor chimerism as low as 7%, no donor-derived cells were detectable when typing was performed >10 months after BMT. In mixed allogeneic bone marrow chimeras multiple cell lineages ($\alpha\beta$TCR+ T cells, B cells, granulocytes/macrophages) of donor and host origin were present ≧10 months after BMT (Table 12 and FIG. 23). The presence of mixed multilineage bone marrow chimerism supports the engraftment of both host and donor HSC.

TABLE 12

LEVEL OF DONOR CHIMERISM AND PRESENCE OF MULTILINEAGE ENGRAFTMENT IN ACI -> WF CHIMERAS*

| | Level of donor chimerism [%] after BMT | | | | Multilineage typing (10–12 months after BMT) | | |
|---|---|---|---|---|---|---|---|
| Chimera# | 28 days | 7 Months | 10 Months | 12 Months | % Donor B Cells† | % Donor T Cells † | % Donor macrophages/ granulocytes ‡ |
| 1 | 7 | NT$ | 0 | 0 | NT | NT | NT |
| 2 | 23 | NT | 43 | 34 | 36 | 20 | 50 |
| 3 | 52 | NT | 91 | 95 | 56 | 57 | 78 |
| 4 | 30 | NT | 51 | 49 | 34 | 27 | 64 |
| 5 | 93 | 93 | 93 | NT | 45 | 38 | 51 |
| 6 | 25 | 94 | 94 | NT | 41 | 54 | 43 |
| 7 | 70 | 82 | 81 | NT | 53 | 61 | 70 |

*ACI -> WF chimeras were prepared by conditioning with anti-NK mAb plus 900 cGy TBI and transplantation with 100 × 10$^6$ TCD bone marrow cells.
†Percent of gated lymphocytes
‡Percent of gated macrophages/granulocytes.
$NT = not tested 12.2.8. Evidence for Donor-Specific Tolerance in vivo: Permanent Acceptance of Cardiac Allografts To determine whether mixed allogeneic chimeras exhibit donor-specific tolerance in vivo after partial conditioning with in vivo NK cell depletion and TBI, transplantation of heterotopic cardiac allografts was performed. One hundred percent of chimeras conditioned with anti-NK mAb and TBI (n=4) or ALS, anti-NK mAb and TBI (n=5) accepted cardiac allografts permanently (Table 13). Explantation and histological examination of grafts was performed 16 to 27 weeks after transplantation. All grafts showed palpable contractions ranging from 3+ to 4+ at the time of harvesting and none of the grafts showed signs of inflammation indicating donorspecific tolerance (FIG. 24). In contrast, when cardiac allografts were transplanted in bone marrow recipients that did not present detectable donor chimerism at the time point of cardiac transplantation (n=2), graft loss due to severe rejection occurred after 22 and 28 days, respectively.

TABLE 13

SURVIVAL OF HETEROTOPIC CARDIAC ALLOGRAFTS IN ACI -> WF CHIMERAS*

| Group | n | Pretreatment | Heart donor | Recipient | Level of donor chimerism † | Survival (MST) [days] | Inflammation score ‡ |
|---|---|---|---|---|---|---|---|
| A | 4 | anti-NK | ACI | WF | 60% (30–95) | >114 (2x), >1 52, >191 (>33)$ | 0(0–0.5)$ |
| B | 5 | anti-NK + ALS | ACI | WF | 93% (31–95) | >170 (3x), >1 91 (2x) (>170)$ | 0(0–0.25)$ |
| C | 2 | anti-NK + ALS | ACI | WF | 0% | 22, 28 (25) | 4 |

*WF rats were pretreated with anti-NK mAb alone or ALS plus anti-NK mAb followed by 900 cGy TBI. Cardiac transplants were performed 4 to 8 weeks after reconstitution with 100 × 10$^6$ TCD bone marrow cells from ACI rats.
† Median (range)
‡ Median inflammation score (range): 0 = none to 4 = severe
$<0.05, compared to group C

12.3. Discussion

We and others have previously shown that mixed multi-lineage bone marrow chimerism can be routinely achieved in mice following partial ablative conditioning (Cobbold, S. P., et al., 1986, *Nature*, 323:164; Sarabi, Y., and D. H. Sachs, 1989, *J. Exp. Med.*, 169:493; Colson, Y. L., et al., 1996, *J. Immunol.*, 157:2820; Exner, B. G., et al., 1997, surgery, 122:221; Sykes, M. et al., 1997, *Nat. Med.*, 3:783). In contrast, engraftment of allogeneic bone marrow does not occur as readily in the rat. In fact, even after conditioning with lethal TBI (1000 cGy) engraftment of $75 \times 10^6$ and $150 \times 10^6$ CD5-depleted allogeneic bone marrow cells was observed only in 50% and 57% of recipients, respectively (Markus, P.M., et al., 1993, *Cell Transplant*, 2:345). In other studies engraftment of CD5- and CD3-depleted bone marrow cells was achieved more readily. However, the level of donor chimerism in lethally conditioned recipients was unexpectedly low and ranged from 20% to 80% (Hoffman, A. L., et al., 1989, *Surgery*, 106:354; Blom, D., et al., 1996, *Surgery*, 120:213; Orlott, M. S., et al., 1995, *Transplantation*, 59:282).

The requirement of TBI for allogeneic bone marrow engraftment could be significantly reduced from 1000 to 900 cGy when recipients were pretreated with anti-NK mAb on days −3 and −2 prior to transplantation. Initial engraftment of donor bone marrow was achieved in 92% of NK cell depleted recipients at 900 cGy TBI and the average level of donor chimerism was 41%. In contrast, only 1 of 8 (13%) of animals conditioned with 900 cGy TBI alone engrafted. Interestingly, pretreatment of the recipient on day −5 with ALS alone or in combination with anti-NK mAb did not allow for a further reduction of the TBI dose when compared with recipients treated with anti-NK mAb plus TBI alone. Moreover, the level of donor chimerism in engrafted animals was comparable for all three groups. Because selective NK cell depletion using anti-NK mAb was as effective as pretreatment with ALS, which nonspecifically targets a variety of alloreactive cells including T cells, B cells and NK cells (Forsythe, J. L., 1994, *Transpl. Immunol.*, 2:148), we hypothesize that allogeneic bone marrow rejection after partially ablative TBI with 900 cGy is at least partially mediated by radio resistant NK cells.

To identify the residual cellular populations after 900 cGy TBI that might be responsible for the observed rejection of allogeneic bone marrow cells in our model, we analyzed spleen and PB from conditioned but not transplanted animals on day +1 after TBI using flow cytometry. Propidium iodide staining was utilized to discriminate live cells from dead cells. It has been previously reported that splenocytes and PBL of athymic nude rats, in which NK cells are the predominant alloreactive effector cells, had the highest cytotoxic activity against allogeneic bone marrow cells (Rolstad, B., and H.B. Benestad, 1994, *Eur. J. Immunol.*, 14:793). The frequency of NK cells in PB was significantly increased to more than 50% of PI negative PBL after 900 cGy TBI alone. In contrast, pretreatment with anti-NK mAb completely eliminated NK cells from PB. In the spleen of animals that received TBI alone a similar enrichment for NK cells was observed, while the percentage of cells showing a positive expression of NKRPl was reduced to $\leq 1\%$ in anti-NK mAb-treated animals. After staining splenocytes with secondary mAb, approximately one forth of cells showed coating with anti-NK cell mAb. These splenocytes were exclusively of $NK3.2.3^{dim}$ phenotype while $NK3.2.3^{bright}$ cells were completely eliminated by pretreatment with anti-NK mAb. These results are in accordance with data from Engh et al. who observed an enrichment of NK cells capable of lysing allogeneic lymphocytes and NK-sensitive tumor cells in spleens of rats on day +1 after 500 cGy TBI (Engh, E., et al., 1996; *Transp. Proc.*, 28:3265). In contrast to PB, T cells were not as readily depleted from spleen after TBI alone or TBI plus mAb. We hypothesize that these residual $\alpha\beta TCR+$ T cells might migrate into the spleen from the periphery and reside in an early stage of apoptosis that was not detected by P1 staining. Rejection of allogeneic bone marrow, however, seemed not to be mediated by the above described splenocytes since additional targeting of T cells with ALS did not improve bone marrow engraftment.

While Rolstad and colleagues mainly focused on natural resistance against allogeneic bone marrow cells, long-term engraftment was not assessed in these studies (Rolstad and Benestad, 1984; Engh et al., 1996). We present here that long term engraftment of allogeneic bone marrow occurred in NK-depleted recipients and stable donor chimerism was detectable in 6 of 7 animals for up to 12 months following BM transplantation. Furthermore, multiple cell lineages of donor and host origin were present in mixed allogeneic chimeras $\geq 10$ months after reconstitution, indicating donor as well as host HSC engraftment. Mixed allogeneic chimeras accepted donor-specific cardiac allografts indefinitely and explanted grafts showed no signs of acute or chronic rejection.

In summary, the foregoing data demonstrate that rejection of completely MHC-disparate bone marrow in partially ablated rats receiving 800–1000 cGy TBI is primarily mediated by radio-resistant host NK cells. Bone marrow rejection could be prevented by selective in vivo depletion of host NK cells using anti-NK3.2.3 mAb. Additional targeting of T cells in the recipient by treatment with ALS did not allow for a further reduction of the TBI dose.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for conditioning a recipient for bone marrow transplantation comprising subjecting the recipient to treatment with a total dose of total body irradiation from 850 cGy to 950 cGy, and treating the recipient with monoclonal antibodies or active fragments thereof directed to NK cells, followed by transplantation with a T-cell depleted donor cell preparation containing hematopoietic stem cells which are not compatible with the recipient at the major histocompatibility complex, to achieve stable engraftmlienlt of donor hematopoictic stem cells, without the development of lethal graft-versus-host disease.

2. The method of claim 1 in which the recipient is further treated with an alkylating agent before, during, or after total body irradiation.

3. The method of claim 2 in which the alkylating agent is cyclophosphamide.

4. The method of claim 1 in which the total dose of total body irradiation is 900 cGy.

5. The method of claim 1 in which the recipient is further treated with anti-lymphocyte serum.

6. The method of claim 1 in which the donor cell preparation is obtained from a human.

7. The method of claim 1 in which the donor cell preparation is obtained from a non-human primate.

8. The method of claim 1 in which the donor cell preparation is obtained from a pig.

9. The method of claim 1 in which the donor cell preparation further comprises hematopoietic facilitatory cells having a phenotype of $CD8^+$, $\alpha\beta TCR^-$, and $\delta\gamma TCR^-$.

* * * * *